US007488832B2

(12) United States Patent
Cole et al.

(10) Patent No.: US 7,488,832 B2
(45) Date of Patent: Feb. 10, 2009

(54) AZOLYLACYLGUANIDINES AS β-SECRETASE INHIBITORS

(75) Inventors: Derek Cecil Cole, New City, NY (US); Eric Steven Manas, Lafayette Hill, PA (US); Lee Dalton Jennings, Chestnut Ridge, NY (US); Frank Eldridge Lovering, Acton, MA (US); Joseph Raymond Stock, Monroe, NY (US); William Jay Moore, Collegeville, PA (US); John Watson Ellingboe, Ridgewood, NJ (US); Jeffrey Scott Condon, Cambridge, MA (US); Mohani Nirmala Sukhdeo, Richmond Hill, NY (US); Ping Zhou, Plainsboro, NJ (US); Junjun Wu, Arlington, MA (US); Koi Michele Morris, Plainsboro, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/352,820

(22) Filed: Feb. 13, 2006

(65) Prior Publication Data
US 2006/0183790 A1 Aug. 17, 2006

Related U.S. Application Data

(60) Provisional application No. 60/652,696, filed on Feb. 14, 2005.

(51) Int. Cl.
C07D 207/325 (2006.01)
A61K 31/4025 (2006.01)
(52) U.S. Cl. ..................... 548/560; 514/427
(58) Field of Classification Search .............. None
See application file for complete search history.

(56) References Cited

U.S. PATENT DOCUMENTS

| 4,140,793 | A | 2/1979 | Ward |
| 4,225,613 | A | 9/1980 | Ward |
| 6,054,457 | A | 4/2000 | Setoi et al. |
| 6,399,824 | B1 | 6/2002 | Hofmeister et al. |
| 6,656,957 | B1 | 12/2003 | Allgeier et al. |
| 6,689,804 | B2 | 2/2004 | Wu et al. |
| 6,974,829 | B2 | 12/2005 | Tung et al. |
| 7,285,682 | B2 | 10/2007 | Hu |
| 2005/0282825 | A1 | 12/2005 | Malamas et al. |
| 2005/0282826 | A1 | 12/2005 | Malamas et al. |
| 2006/0111370 | A1 | 5/2006 | Zhu et al. |
| 2006/0160828 | A1 | 7/2006 | Malamas et al. |
| 2006/0173049 | A1 | 8/2006 | Malamas et al. |
| 2006/0183792 | A1 | 8/2006 | Fobare et al. |
| 2007/0004730 | A1 | 1/2007 | Zhou |
| 2007/0004786 | A1 | 1/2007 | Malamas et al. |
| 2007/0027199 | A1 | 2/2007 | Malamas et al. |
| 2007/0072925 | A1 | 3/2007 | Malamas et al. |
| 2007/0191431 | A1 | 8/2007 | Zhou |
| 2007/0203116 | A1 | 8/2007 | Quagliato et al. |
| 2008/0051390 | A1 | 2/2008 | Malamas et al. |

FOREIGN PATENT DOCUMENTS

| EP | 0861831 A1 | 9/1998 |
| GB | 2013192 A | 8/1979 |
| GB | 2181347 A * | 4/1987 |
| WO | WO 97/45417 A1 | 12/1997 |
| WO | WO 98/45267 | 10/1998 |
| WO | WO 01/87829 A1 | 11/2001 |
| WO | WO 03/053938 A1 | 7/2003 |
| WO | WO 03/064396 A1 | 8/2003 |
| WO | WO 03/094854 A2 | 11/2003 |
| WO | WO 2005/005412 A1 | 1/2005 |
| WO | WO 2005/058311 A1 | 6/2005 |
| WO | WO 2006/009653 A1 | 1/2006 |
| WO | WO 2006/065277 A2 | 6/2006 |
| WO | WO 2007/005404 A1 | 1/2007 |
| WO | WO 2007/016012 A2 | 2/2007 |

OTHER PUBLICATIONS

MayoClinic.com, Alzheimer's disease: Cause.*
Su et al.; Expert opinion on drug delivery (May 2006) vol. 3, abstract.*
Lefrance-Jullien et al., British Journal of Pharmacology (2005), 145, 228-235.*
Lyketsos et al., The American Journal of Geriatric Psychiatry (2006), 14, 561-573.*
Fact Sheet, Alzheimer's Association, 2006.*
Vandana et al., Journal of drug targeting (2005), vol. 13, abstract.*
Abbott et al., Molecular Medicine Today (1996), vol. 2, p. 106-113.*
Allimony et al., "Synthesis and antimicrobial activity of some nitrogen heterobicyclic systems: Part I", Indian Journal of Chemistry, 1999, vol. 38B, pp. 445-451.

(Continued)

Primary Examiner—Rebecca Anderson
Assistant Examiner—Sun Jae Y Loewe
(74) Attorney, Agent, or Firm—Joel Silver; Scott Larsen; Andrea Dorigo

(57) ABSTRACT

The present invention provides an azolylacylquanidine compound of formula I (I)

[chemical structure showing formula I with substituents $NR_3R_4$, $NH_2$, R, $R_1$, $R_2$, X, Y, Z, O]

The present invention also provides methods for the use thereof to inhibit β-secretase (BACE) and treat β-amyloid deposits and neurofibrillary tangles.

8 Claims, No Drawings

OTHER PUBLICATIONS

National Institute of Neurological Discorders and Stroke, "Alzheimer's Disease Information Page", retrieved from internet on Jun. 27, 2007, http://www.ninds.nih.gov/disorders/alzheimersdisease/alzheimersdisease.htm.

PCT Preliminary Report on Patentability, Written Opinion of the ISR, International Patent Application PCT/US2006/024793, International filing date Jun. 26, 2006.

PCT Preliminary Report on Patentability, Written Opinion of the ISR, International Patent Application PCT/US2006/024912, International filing date Jun. 26, 2006.

Selkoe, "Alzheimer'Disease: Genes, Proteins, and Therapy", Physiological Reviews, 2001, vol. 81(2), pp. 741-766.

Tao et al., "Synthesis of Conformationally constrained spirohydantoins with a Dibenzo[a,d]heptadiene ring", Synthesis 2000, No. 10, pp. 1449-1453.

Varghese et al., "Human beta-secretase (BACE) and BACE Inhibitors", J. Med. Chem. 2003, vol. 46(22), pp. 4625-4630.

Xiao et al., "An improved procedure for the synthesis of 4,4-disubstituted-3-oxo-1,2,5-thiadiazolidine 1,1-dioxides", J. Heterocyclic Chem., 2000, vol. 37, pp. 773-777.

Yamada et al., "Hydantoin derivatives, I. Actions on central nervous system of 5,5-diarylhydantoins and 5,5-diarylhydantion-2-imines", Abstract, Oyo Yakuri, 1975, vol. 9(6), pp. 841-847.

* cited by examiner

AZOLYLACYLGUANIDINES AS β-SECRETASE INHIBITORS

This application claims the benefit under 35 U.S.C. §119 (e) to co-pending U.S. Provisional Application No. 60/652,696, filed Feb. 14, 2005, which is hereby incorporated by reference in its entirety.

BACKGROUND OF THE INVENTION

β-Amyloid deposits and neurofibrillary tangles are two major pathologic characterizations associated with Alzheimer's disease (AD). Clinically, AD is characterized by the of loss of memory, cognition, reasoning, judgment, and orientation. Also affected, as the disease progresses, are motor, sensory, and linguistic abilities until global impairment of multiple cognitive functions occurs. These cognitive losses take place gradually, but typically lead to severe impairment and eventual death in 4-12 years.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders. (Varghese, J., et al, Journal of Medicinal Chemistry, 2003, 46, 4625-4630).

β-amyloid deposits are predominately an aggregate of Aβ peptide, which in turn is a product of the proteolysis of amyloid precursor protein (APP). More specifically, Aβ peptide results from the cleavage of APP at the C-terminus by one or more β-secretases, and at the N-terminus by β-secretase enzyme (BACE), also known as aspartyl protease, as part of the β-amyloidogenic pathway.

BACE activity is correlated directly to the generation of Aβ peptide from APP (Sinha, et al, Nature, 1999, 402, 537-540), and studies increasingly indicate that the inhibition of BACE inhibits the production of Aβ peptide. (Roberds, S. L., et al, Human Molecular Genetics, 2001, 10, 1317-1324).

Therefore, it is an object of this invention to provide compounds which are inhibitors of β-secretase and are useful as therapeutic agents in the treatment, prevention or amelioration of a disease or disorder characterized by elevated β-amyloid deposits or β-amyloid levels in a patient.

It is another object of this invention to provide therapeutic methods and pharmaceutical compositions useful for the treatment, prevention or amelioration of a disease or disorder characterized by elevated β-amyloid deposits or β-amyloid levels in a patient.

It is a feature of this invention that the compounds provided may also be useful to further study and elucidate the β-secretase enzyme.

These and other objects and features of the invention will become more apparent by the detailed description set forth hereinbelow.

SUMMARY OF THE INVENTION

The present invention provides a compound of I

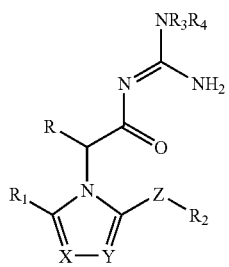

(I)

wherein
X is N or $CR_5$;
Y is N or $CR_6$;
Z is CO or $(CH_2)_n$;
n is 0, 1, 2 or 3;
R is H, alkyl or aryl;
$R_1$ and $R_2$ are each independently cycloalkyl, cycloheteroalkyl, aryl or heteroaryl;
$R_3$ and $R_4$ are each independently H, alkyl, alkanoyl, alkoxy, alkenyl, cycloalkyl, cycloheteroalkyl, aryl or heteroaryl or $R_3$ and $R_4$ may be taken together with the atom to which they are attached to form a 5- to 7-membered ring optionally containing an additional heteroatom selected from O, N or S; and
$R_5$ and $R_6$ are each independently halogen, alkyl, haloalkyl, alkoxy or haloalkoxy; or a tautomer thereof, a stereoisomer thereof or a pharmaceutically acceptable salt thereof.

The present invention also provides compositions and methods for the treatment of β-amyloid deposits and neurofibrillary tangles.

DETAILED DESCRIPTION OF THE INVENTION

Alzheimer's disease (AD), a progressive degenerative disease of the brain primarily associated with aging, has become a more serious healthcare problem since its initial description almost a century ago (Alzheimer, A. *Centralblatt fur Nervenheikunde und Psychiatrie,* 1907, 30, 117-179). For example, the number of prevalent cases of AD continues to grow at an alarming rate of more than 5% annually in Japan (Citron, M. *J. Neuroscience Research,* 2002, 70, 373-379). Clinically, AD is presented by characterization of loss of memory, cognition, reasoning, judgment, and orientation. Motor, sensory, and linguistic abilities are also affected as the disease progresses until global impairment of multiple cognitive functions occurs. These cognitive losses take place gradually, but typically lead to severe impairment and eventual death in 4-12 years. Consequently, there is an urgent need for pharmaceutical agents capable of halting, preventing or reversing the progression of Alzheimer's disease.

β-Amyloid plaques (predominately an aggregate of a peptide fragment known as A-β) and neurofibrillary tangles are two major pathologic characterizations associated with Alzheimer's disease. Patients with AD display characteristic β-amyloid deposits (β-amyloid plaques) in the brain and in cerebral blood vessels (β-amyloid angiopathy) as well as neurofibrillary tangles. Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other dementia-inducing disorders.

A-β peptide is a product of the proteolysis of amyloid precursor protein (APP) by several proteasese called secretases. It results from the cleavage of APP at the N-terminus by β-secretase and at the C-terminus by one or more β-secretase, i.e., the β-amyloidogenic pathway. An aspartyl protease, designated as BACE, Asp, Memapsin, has been identified as the enzyme responsible for the processing of APP at the β-secretase cleavage site (Sinha, et al, *Nature,* 1999, 402, 537-554). Thus, inhibition of this enzyme's activity, i.e. BACE activity, is desirable for the treatment of AD, Down's Syndrome, HCHWA-D and other neurodegenerative and dementia-inducing disorders.

Surprisingly it has now been found that azolylacylguanidine compounds of formula I effectively inhibit β-secretase and selectively inhibit BACE1. Advantageously, said acylguanidine compounds may be used as effective therapeutic agents for the treatment, prevention or amelioration of a disease or disorder characterized by elevated β-amyloid deposits or β-amyloid levels in a patient. Accordingly, the present invention provides a compound of formula I

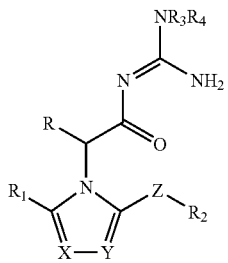

wherein
X is N or $CR_5$;
Y is N or $CR_6$;
Z is CO or $(CH_2)_n$;
n is 0, 1, 2 or 3;
R is H, alkyl or aryl;
$R_1$ and $R_2$ are each independently cycloalkyl, cycloheteroalkyl, aryl or heteroaryl;
$R_3$ and $R_4$ are each independently H, alkyl, alkanoyl, alkoxy, alkanoyl, alkenyl, cycloalkyl, cycloheteroalkyl, aryl or heteroaryl or $R_3$ and $R_4$ may be taken together with the atom to which they are attached to form a 5- to 7-membered ring optionally containing an additional heteroatom selected from O, N or S; and
$R_5$ and $R_6$ are each independently halogen, alkyl, haloalkyl, alkoxy or haloalkoxy; or a tautomer thereof, a stereoisomer thereof or a pharmaceutically acceptable salt thereof.

Preferred compounds of formula I are those compounds having the structure of formula Ia

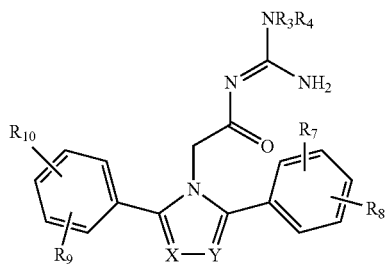

wherein
X, Y, $R_3$ and $R_4$ are as defined for formula I hereinabove;
$R_7$, $R_8$, $R_9$ and $R_{10}$ are each independently H, halogen, alkyl, haloalkyl, cycloalkyl, cycloheteroalkyl, aryl, heteroaryl, $OR_{11}$, $COR_{11}$, $CONR_{12}R_{13}$, $NR_{12}R_{13}$, $NR_{14}COR_{15}$, $NR_{14}SO_2R_{15}$ or $NR_{14}CONR_{16}R_{17}$;
$R_{11}$ is H, alkyl, haloalkyl, alkenyl, alkynyl, cycloalkyl, cycloheteroalkyl, aryl or heteroaryl;
$R_{12}$, $R_{13}$, $R_{16}$ and $R_{17}$ are each independently H, alkyl, alkoxy, alkenyl, cycloalkyl, cycloheteroalkyl, aryl or heteroaryl or $R_{12}$ and $R_{13}$ or $R_{16}$ and $R_{17}$ may be taken together with the atom to which they are attached to form a 5- to 7-membered ring optionally containing an additional heteroatom selected from O, N or S;
$R_{14}$ is H, alkyl or cycloalkyl; and
$R_{15}$ is alkyl, haloalkyl, alkenyl, alkynyl, cycloalkyl, cycloheteroalkyl, aryl or heteroaryl.

It is understood that the claims encompass all possible stereoisomers and prodrugs. Moreover, unless stated otherwise, each alkyl, alkenyl, alkynyl, cycloalkyl cycloheteroalkyl, aryl or heteroaryl group is contemplated as being optionally substituted.

An optionally substituted moiety may be substituted with one or more substituents. The substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Unless otherwise specified, typically, 0-4 substituents may be present. When any of the foregoing substituents represents or contains an alkyl substituent group, this may be linear or branched and may contain up to 12 carbon atoms, preferably up to 6 carbon atoms, more preferably up to 4 carbon atoms.

As used herein, the term "alkyl" includes both ($C_1$-$C_{10}$) straight chain and ($C_3$-$C_{12}$) branched-chain (unless defined otherwise) monovalent saturated hydrocarbon moiety. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, and the like. Specifically included within the definition of "alkyl" are those alkyl groups that are optionally substituted. Suitable alkyl substitutions include, but are not limited to, CN, OH, halogen, phenyl, carbamoyl, carbonyl, alkoxy or aryloxy.

As used herein the term "haloalkyl" designates a $C_nH_{2n+1}$ group having from one to 2n+1 halogen atoms which may be the same or different. Examples of haloalkyl groups include $CF_3$, $CH_2Cl$, $C_2H_3BrCl$, $C_3H_5F_2$, or the like.

The term "alkenyl", as used herein, refers to either a ($C_2$-$C_{10}$) straight chain or ($C_3$-$C_{10}$) branched-chain monovalent hydrocarbon moiety containing at least one double bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, or the like.

The term "cycloalkyl", as used herein, refers to a monocyclic, bicyclic, tricyclic, fused, bridged, or spiro monovalent saturated hydrocarbon moiety of 3-10 carbon atoms. Examples of cycloalkyl moieties include, but are not limited to, chemical groups such as cyclopropyl, cyclopropyl, cyclobutyl, cyclopentyl, cyclohexyl, cyclohexyl, cyclohexyl, cycloheptyl, norbornyl, adamantyl, spiro[4.5]decanyl, or the like.

The term "cycloheteroalkyl" as used herein designates a five- to seven-membered cycloalkyl ring system containing 1, 2 or 3 heteroatoms, which may be the same or different, selected from N, O or S and optionally containing one double bond. Exemplary of the cycloheteroalkyl ring systems included in the term as designated herein are the following rings wherein $X_1$ is NR', O or S and R' is H or an optional substituent as defined hereinbelow.

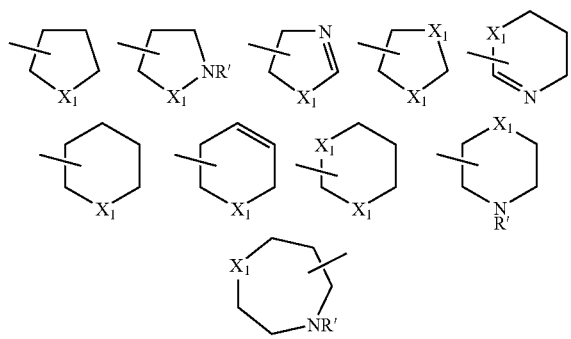

The term "aryl", as used herein, refers to an aromatic carbocyclic moiety of up to 20 carbon atoms, which may be a single ring (monocyclic) or multiple rings (bicyclic or tricyclic) fused together or linked covalently. Examples of aryl moieties include, but are not limited to, chemical groups such as phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, or the like.

The term "heteroaryl" as used herein means an aromatic heterocyclic ring system, which may be a single ring (monocyclic) or multiple rings (bicyclic or tricyclic) fused together or linked covalently. Preferably, heteroaryl is a 5- to 6-membered ring. The rings may contain from one to four hetero atoms selected from nitrogen, oxygen, or sulfur, wherein the nitrogen or sulfur atom(s) are optionally oxidized, or the nitrogen atom(s) are optionally quarternized. Any suitable ring position of the heteroaryl moiety may be covalently linked to the defined chemical structure. Examples of heteroaryl moieties include, but are not limited to, heterocycles such as furan, thiophene, pyrrole, pyrazole, imidazole, oxazole, isoxazole, thiazole, isothiazole, 1H-tetrazole, 1,3,4-oxadiazole, 1H-1,2,4-triazole, pyridine, pyrimidine, pyrazine, pyridazine, benzoxazole, benzisoxazole, benzothiazole, benzofuran, benzothiophene, thianthrene, dibenzo[b,d]furan, dibenzo[b,d]thiophene, benzimidazole, indole, indazole, quinoline, isoquinoline, quinazoline, quinoxaline, purine, pteridine, 9H-carbazole, α-carboline, or the like.

The term "halogen", as used herein, designates fluorine, chlorine, bromine, and iodine.

The compounds of the present invention may be converted to salts, in particular pharmaceutically acceptable salts using art recognized procedures. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethyl-propylamine, or a mono-, di-, or trihydroxy lower alkylamine, for example mono-, di- or triethanolamine. Internal salts may furthermore be formed. Salts which are unsuitable for pharmaceutical uses but which can be employed, for example, for the isolation or purification of free compounds or their pharmaceutically acceptable salts, are also included. The term "pharmaceutically acceptable salt", as used herein, refers to salts derived form organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one steriosomer, preferably less than about 50%, more preferably less than about 75%, and even more preferably less than about 90%.

Preferred compounds of formula I are those compounds wherein X is $CR_5$; Y is $CR_6$; and R is H. Another group of preferred compounds are those compounds of formula I wherein R is H; $R_1$ is phenyl and $R_2$ is cycloalkyl. Also preferred are those compounds of formula I having the structure of formula Ia

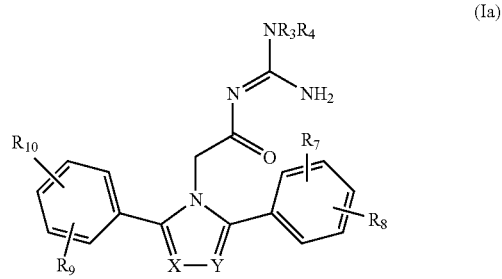

(Ia)

wherein

X, Y, $R_3$ and $R_4$ are as defined for formula I hereinabove;

$R_7$, $R_8$, $R_9$ and $R_{10}$ are each independently H, halogen, alkyl, haloalkyl, cycloalkyl, cycloheteroalkyl, aryl, heteroaryl, $OR_{11}$, $COR_{11}$, $CONR_{12}R_{13}$, $NR_{12}R_{13}$, $NR_{14}COR_{15}$, $NR_{14}SO_2R_{15}$ or $NR_{14}CONR_{16}R_{17}$;

$R_{11}$ is H, alkyl, haloalkyl, alkenyl, alkynyl, cycloalkyl, cycloheteroalkyl, aryl or heteroaryl;

$R_{12}$, $R_{13}$, $R_{16}$ and $R_{17}$ are each independently H, alkyl, alkoxy, alkenyl, cycloalkyl, cycloheteroalkyl, aryl or heteroaryl or $R_{12}$ and $R_{13}$ or $R_{16}$ and $R_{17}$ may be taken together with the atom to which they are attached to form a 5- to 7-membered ring optionally containing an additional heteroatom selected from O, N or S;

$R_{14}$ is H, alkyl or cycloalkyl; and
$R_{15}$ is alkyl, haloalkyl, alkenyl, alkynyl, cycloalkyl, cycloheteroalkyl, aryl or heteroaryl.

More preferred compounds of the invention are those compounds of formula I wherein X and Y are CH; R is H; Z is $(CH_2)_n$; n is 0; and $R_2$ is adamantyl. Another group of more preferred compounds of the invention are those compounds of formula Ia wherein X and Y are CH; and R, $R_7$ and $R_9$ are H. A further group of more preferred compounds of the invention are those compounds of formula Ia wherein X and Y are CH; R, $R_7$ and $R_9$ are H; $R_8$ and $R_{10}$ are each independently H, halogen or $OR_{11}$.

Preferred compounds of the invention include:
N-[amino(imino)methyl]-2-[2-(4-phenoxyphenyl)-5-phenyl-1H-pyrrol-1-yl]acetamide;
2-{2-[4-(4-acetylphenoxy)phenyl]-5-phenyl-1H-pyrrol-1-yl}-N-[amino(imino)methyl]acetamide;
N-[amino(imino)methyl]-2-[2-(2-chlorophenyl)-5-(4-phenoxyphenyl)-1H-pyrrol-1-yl]acetamide;
2-[2-[4-(4-acetylphenoxy)phenyl]-5-(2-chlorophenyl)-1H-pyrrol-1-yl]-N-[amino(imino)methyl]acetamide;
N-[amino(imino)methyl]-2-[2-(3-chlorophenyl)-5-(4-phenoxyphenyl)-1H-pyrrol-1-yl]acetamide;
N-[amino(imino)methyl]-2-[2-(3-fluorophenyl)-5-(4-phenoxyphenyl)-1H-pyrrol-1-yl]acetamide;
2-[2-[4-(4-acetylphenoxy)phenyl]-5-(3-fluorophenyl)-1H-pyrrol-1-yl]-N-[amino(imino)methyl]acetamide;
N-[amino(imino)methyl]-2-[2-(2-methoxyphenyl)-5-(4-phenoxyphenyl)-1H-pyrrol-1-yl]acetamide;
2-[2-[4-(4-acetylphenoxy)phenyl]-5-(2-methoxyphenyl)-1H-pyrrol-1-yl]-N-[amino(imino)methyl]acetamide;
N-[amino(imino)methyl]-2-[2-(3-methoxyphenyl)-5-(4-phenoxyphenyl)-1H-pyrrol-1-yl]acetamide;
2-[2-[4-(4-acetylphenoxy)phenyl]-5-(3-methoxyphenyl)-1H-pyrrol-1-yl]-N-[amino(imino)methyl]acetamide;
N-[amino(imino)methyl]-2-[2-(4-fluorophenyl)-5-(4-phenoxyphenyl)-1H-pyrrol-1-yl]acetamide;
2-[2-[4-(4-acetylphenoxy)phenyl]-5-(4-fluorophenyl)-1H-pyrrol-1-yl]-N-[amino(imino)methyl]acetamide;
N-[amino(imino)methyl]-2-[2-(2,5-dimethoxyphenyl)-5-(4-phenoxyphenyl)-1H-pyrrol-1-yl]acetamide;
2-[2-[4-(4-acetylphenoxy)phenyl]-5-(2,5-dimethoxyphenyl)-1H-pyrrol-1-yl]-N-[amino(imino)methyl]acetamide;
N-[amino(imino)methyl]-2-(2-{4-[(4-methylpiperidin-1-yl)carbonyl]phenyl}-5-phenyl-1H-pyrrol-1-yl)acetamide;
N-{4-[1-(2-{[amino(imino)methyl]amino}-2-oxoethyl)-5-phenyl-1H-pyrrol-2-yl]phenyl}-2,4-dichlorobenzamide;
N-{4-[1-(2-{[amino(imino)methyl]amino}-2-oxoethyl)-5-phenyl-1H-pyrrol-2-yl]phenyl}-4-bromobenzamide;
N-{4-[1-(2-{[amino(imino)methyl]amino}-2-oxoethyl)-5-phenyl-1H-pyrrol-2-yl]phenyl}-3-methoxybenzamide;
N-{4-[1-(2-{[amino(imino)methyl]amino}-2-oxoethyl)-5-phenyl-1H-pyrrol-2-yl]phenyl}-3-methylbenzamide;
N-{4-[1-(2-{[amino(imino)methyl]amino}-2-oxoethyl)-5-phenyl-1H-pyrrol-2-yl]phenyl}-2-phenoxyacetamide;
N-{4-[1-(2-{[amino(imino)methyl]amino}-2-oxoethyl)-5-phenyl-1H-pyrrol-2-yl]phenyl}-3-bromobenzamide;
2-{2-[4-(allyloxy)phenyl]-5-phenyl-1H-pyrrol-1-yl}-N-[amino(imino)methyl]acetamide;
N-[amino(imino)methyl]-2-(2-{4-[(2-methylprop-2-enyl)oxy]phenyl}-5-phenyl-1H-pyrrol-1-yl)acetamide;
N-[amino(imino)methyl]-2-{2-[4-(but-3-enyloxy)phenyl]-5-phenyl-1H-pyrrol-1-yl}acetamide;
N-[amino(imino)methyl]-2-(2-{4-[(4-cyanobenzyl)oxy]phenyl}-5-phenyl-1H-pyrrol-1-yl)acetamide;
N-[amino(imino)methyl]-2-[2-(4-ethoxyphenyl)-5-phenyl-1H-pyrrol-1-yl]acetamide;
N-[amino(imino)methyl]-2-[2-(4-butoxyphenyl)-5-phenyl-1H-pyrrol-1-yl]acetamide;
N-[amino(imino)methyl]-2-{2-[4-(3-cyanopropoxy)phenyl]-5-phenyl-1H-pyrrol-1-yl}acetamide;
N-[amino(imino)methyl]-2-[2-(4-{[(2S)-2-methylbutyl]oxy}phenyl)-5-phenyl-1H-pyrrol-1-yl]acetamide;
N-{(1E)-amino[(3-cyanopropyl)amino]methylene}-2-[2-(2-chlorophenyl)-5-(4-phenoxyphenyl)-1H-pyrrol-1-yl]acetamide;
N-{(1E)-amino[(3-hydroxypropyl)amino]methylene}-2-[2-(2-chlorophenyl)-5-(4-phenoxyphenyl)-1H-pyrrol-1-yl]acetamide;
methyl(2R)-3-{[(Z)-amino({[2-(2-chlorophenyl)-5-(4-phenoxyphenyl)-1H-pyrrol-1-yl]acetyl}imino)methyl]amino}-2-methylpropanoate;
2-{[(Z)-amino({[2-(2-chlorophenyl)-5-(4-phenoxyphenyl)-1H-pyrrol-1-yl]acetyl}imino)methyl]amino}ethyl acetate;
2-{2-(2-chlorophenyl)-5-[4-(pent-4-enyloxy)phenyl]-1H-pyrrol-1-yl}-N-[[(3-hydroxypropyl)amino](imino)methyl]acetamide;
2-{2-(2-chlorophenyl)-5-[4-(4-cyanobutoxy)phenyl]-1H-pyrrol-1-yl}-N-[[(3-hydroxypropyl)amino](imino)methyl]acetamide;
2-{2-(2-chlorophenyl)-5-[4-(hex-5-enyloxy)phenyl]-1H-pyrrol-1-yl}-N-[[(3-hydroxypropyl)amino](imino)methyl]acetamide;
2-(2-(2-chlorophenyl)-5-{4-[2-(1,3-dioxolan-2-yl)ethoxy]phenyl}-1H-pyrrol-1-yl)-N-[[(3-hydroxypropyl)amino](imino)methyl]acetamide;
2-{2-(2-chlorophenyl)-5-[4-(pentyloxy)phenyl]-1H-pyrrol-1-yl}-N-[[(3-hydroxypropyl)amino](imino)methyl]acetamide;
2-[2-(4-cyanophenyl)-5-phenyl-1H-pyrrol-1-yl]-N-[[(3-hydroxypropyl)amino](imino)methyl]acetamide;
N-[[(3-hydroxypropyl)amino](imino)methyl]-2-[2-(4-isopropylphenyl)-5-phenyl-1H-pyrrol-1-yl]acetamide;
N-[[(3-hydroxypropyl)amino](imino)methyl]-2-[2-phenyl-5-(4-propylphenyl)-1H-pyrrol-1-yl]acetamide;
2-[2-(4-butylphenyl)-5-phenyl-1H-pyrrol-1-yl]-N-[[(3-hydroxypropyl)amino](imino)methyl]acetamide;
N-[[(3-hydroxypropyl)amino](imino)methyl]-2-[2-(4-isobutylphenyl)-5-phenyl-1H-pyrrol-1-yl]acetamide;
N-[[(3-hydroxypropyl)amino](imino)methyl]-2-[2-(4-pentylphenyl)-5-phenyl-1H-pyrrol-1-yl]acetamide;
2-[2-(4-butoxyphenyl)-5-phenyl-1H-pyrrol-1-yl]-N-[[(3-hydroxypropyl)amino](imino)methyl]acetamide;
2-[2-(1,1'-biphenyl-4-yl)-5-phenyl-1H-pyrrol-1-yl]-N-[[(3-hydroxypropyl)amino](imino)methyl]acetamide;
2-[2-(4-bromophenyl)-5-phenyl-1H-pyrrol-1-yl]-N-[[(3-hydroxypropyl)amino](imino)methyl]acetamide;
2-[2-(4-cyclohexylphenyl)-5-phenyl-1H-pyrrol-1-yl]-N-[[(3-hydroxypropyl)amino](imino)methyl]acetamide;
N-[[(3-hydroxypropyl)amino](imino)methyl]-2-[2-(4-phenoxyphenyl)-5-phenyl-1H-pyrrol-1-yl]acetamide;
2-{2-[4-(4-acetylphenoxy)phenyl]-5-phenyl-1H-pyrrol-1-yl}-N-[[(3-hydroxypropyl)amino](imino)methyl]acetamide;
2-[2-(4-cyanophenyl)-5-phenyl-1H-pyrrol-1-yl]-N-{imino[(2,3,4-trifluorobenzyl)amino]methyl}acetamide;
N-{imino[(2,3,4-trifluorobenzyl)amino]methyl}-2-[2-phenyl-5-(4-propylphenyl)-1H-pyrrol-1-yl]acetamide;
2-[2-(4-butylphenyl)-5-phenyl-1H-pyrrol-1-yl]-N-{imino[(2,3,4-trifluorobenzyl)amino]methyl}acetamide;
2-[2-(4-butoxyphenyl)-5-phenyl-1H-pyrrol-1-yl]-N-{imino[(2,3,4-trifluorobenzyl)amino]methyl}acetamide;

2-[2-(4-cyclohexylphenyl)-5-phenyl-1H-pyrrol-1-yl]-N-{imino[(2,3,4-trifluorobenzyl)amino]methyl}acetamide;
N-{imino[(2,3,4-trifluorobenzyl)amino]methyl}-2-[2-(4-phenoxyphenyl)-5-phenyl-1H-pyrrol-1-yl]acetamide;
2-{2-[4-(4-acetylphenoxy)phenyl]-5-phenyl-1H-pyrrol-1-yl}-N-{imino[(2,3,4-trifluorobenzyl)amino]methyl}acetamide;
2-[2-(1-adamantyl)-5-phenyl-1H-pyrrol-1-yl]-N-[(1Z)-amino(ethylamino)methylene]acetamide;
2-[2-(1-adamantyl)-5-phenyl-1H-pyrrol-1-yl]-N-[(1Z)-amino(propylamino)methylene]acetamide;
2-[2-(1-adamantyl)-5-phenyl-1H-pyrrol-1-yl]-N-{(1E)-amino[(3-cyanopropyl)amino]methylene}acetamide;
2-{[(Z)-({[2-(1-adamantyl)-5-phenyl-1H-pyrrol-1-yl]acetyl}imino)(amino)methyl]amino}ethyl acetate;
2-[2-(1-adamantyl)-5-phenyl-1H-pyrrol-1-yl]-N-{(1E)-amino[(3-hydroxypropyl)amino]methylene}acetamide;
2-[2-(1-adamantyl)-5-phenyl-1H-pyrrol-1-yl]-N-{(1E)-amino[(2-hydroxyethyl)amino]methylene}acetamide;
2-[2-(1-adamantyl)-5-phenyl-1H-pyrrol-1-yl]-N-{(1E)-amino[(2-cyanoethyl)amino]methylene}acetamide;
2-[2-(1-adamantyl)-5-phenyl-1H-pyrrol-1-yl]-N-((1E)-amino{[2-(1,3-dioxolan-2-yl)ethyl]amino}methylene)acetamide;
2-[2-(1-adamantyl)-5-phenyl-1H-pyrrol-1-yl]-N-{(1E)-amino[(4-hydroxybutyl)amino]methylene}acetamide;
2-[2-(1-adamantyl)-5-phenyl-1H-pyrrol-1-yl]-N-{(1E)-amino[(tetrahydrofuran-2-ylmethyl)amino]methylene}acetamide;
2-[2-(1-adamantyl)-5-phenyl-1H-pyrrol-1-yl]-N-((1Z)-amino{[(2R)-2-hydroxypropyl]amino}methylene)acetamide;
2-[2-(1-adamantyl)-5-phenyl-1H-pyrrol-1-yl]-N-((1Z)-amino{[(2S)-2-hydroxypropyl]amino}methylene)acetamide;
2-[2-(1-adamantyl)-5-phenyl-1H-pyrrol-1-yl]-N-{(1E)-amino[(2,3-dihydroxypropyl)amino]methylene}acetamide;
2-[2-(1-adamantyl)-5-phenyl-1H-pyrrol-1-yl]-N-{(1Z)-amino(isobutylamino)methylene}acetamide;
2-[2-(1-adamantyl)-5-phenyl-1H-pyrrol-1-yl]-N-{(1E)-amino[(2,2,2-trifluoroethyl)amino]methylene}acetamide;
ethyl 4-{[(Z)-({[2-(1-adamantyl)-5-phenyl-1H-pyrrol-1-yl]acetyl}imino)(amino)methyl]amino}butanoate;
2-[2-(1-adamantyl)-5-phenyl-1H-pyrrol-1-yl]-N-[(1E)-amino(cyclopropylamino)methylene]acetamide;
2-[2-(1-adamantyl)-5-phenyl-1H-pyrrol-1-yl]-N-{(1E)-amino[(cyclohexylmethyl)amino]methylene}acetamide;
2-[2-(1-adamantyl)-5-phenyl-1H-pyrrol-1-yl]-N-{(1E)-amino[(trans-4-hydroxycyclohexyl)amino]methylene}acetamide;
2-[2-(1-adamantyl)-5-phenyl-1H-pyrrol-1-yl]-N-((1E)-amino{[3-(1H-imidazol-1-yl)propyl]amino}methylene)acetamide;
2-[2-(1-adamantyl)-5-phenyl-1H-pyrrol-1-yl]-N-{(1Z)-amino[(3-methoxypropyl)amino]methylene}acetamide;
2-[2-(1-adamantyl)-5-phenyl-1H-pyrrol-1-yl]-N-{(1Z)-amino[(2-methoxyethyl)amino]methylene}acetamide;
2-[2-(1-adamantyl)-5-phenyl-1H-pyrrol-1-yl]-N-{(1E)-amino[(2,2,3,3,3-pentafluoropropyl)amino]methylene}acetamide;
2-[2-(1-adamantyl)-5-phenyl-1H-pyrrol-1-yl]-N-[(1E)-amino(cycloheptylamino)methylene]acetamide;
2-[2-(1-adamantyl)-5-phenyl-1H-pyrrol-1-yl]-N-((1Z)-amino{[(5-methyl-1,3,4-oxadiazol-2-yl)methyl]amino}methylene)acetamide;
2-[2-(1-adamantyl)-5-phenyl-1H-pyrrol-1-yl]-N-((1Z)-amino{[(4-methyl-1,3-thiazol-2-yl)methyl]amino}methylene)acetamide;
2-[2-(1-adamantyl)-5-phenyl-1H-pyrrol-1-yl]-N-{(1E)-amino[(2-thien-2-ylethyl)amino]methylene}acetamide;
2-[2-(1-adamantyl)-5-phenyl-1H-pyrrol-1-yl]-N-{(1E)-amino[(3-aminobenzyl)amino]methylene}acetamide;
2-[2-(1-adamantyl)-5-phenyl-1H-pyrrol-1-yl]-N-{(1E)-amino[(2-thien-3-ylethyl)amino]methylene}acetamide;
N-allyl-4-(1-{2-[((1Z)-amino{[(5-methyl-1,3,4-oxadiazol-2-yl)methyl]amino}methylene)amino]-2-oxoethyl}-5-phenyl-1H-pyrrol-2-yl)benzamide;
N-allyl-4-(1-{2-[((1Z)-amino{[(4-methyl-1,3-thiazol-2-yl)methyl]amino}methylene)amino]-2-oxoethyl}-5-phenyl-1H-pyrrol-2-yl)benzamide;
N-allyl-4-{1-[2-({(1E)-amino[(2-thien-2-ylethyl)amino]methylene}amino)-2-oxoethyl]-5-phenyl-1H-pyrrol-2-yl}benzamide;
N-allyl-4-{1-[2-({(1E)-amino[(3-aminobenzyl)amino]methylene}amino)-2-oxoethyl]-5-phenyl-1H-pyrrol-2-yl}benzamide;
2-[2-(1-adamantyl)-5-phenyl-1H-pyrrol-1-yl]-N-{(1Z)-amino[(ethylsulfonyl)amino]methylene}acetamide;
N-(3-cyano-propyl)-N'-[2-(2-cyclohexyl-5-phenyl-pyrrol-1-yl)-acetyl]-guanidine;
N"-{[2-(4-butylphenyl)-5-phenyl-1H-pyrrol-1-yl]acetyl}guanidine;
N"-{[2-(2,5-dimethylphenyl)-5-phenyl-1H-pyrrol-1-yl]acetyl}guanidine;
N"-({2-[3-(cyanomethyl)phenyl]-5-phenyl-1H-pyrrol-1-yl}acetyl)guanidine;
N"-({2-[4-(2-cyanoethyl)phenyl]-5-phenyl-1H-pyrrol-1-yl}acetyl)guanidine;
N"-[(2-cyclohexyl-5-phenyl-1H-pyrrol-1-yl)acetyl]guanidine;
4-{1-[2-({(1E)-amino[(3-hydroxypropyl)amino]methylene}amino)-2-oxoethyl]-5-phenyl-1H-pyrrol-2-yl}-N-ethylbenzamide;
4-{1-[2-({(1E)-amino[(3-hydroxypropyl)amino]methylene}amino)-2-oxoethyl]-5-phenyl-1H-pyrrol-2-yl}-N-cyclopropylbenzamide;
N-allyl-4-{1-[2-({(1E)-amino[(3-hydroxypropyl)amino]methylene}amino)-2-oxoethyl]-5-phenyl-1H-pyrrol-2-yl}benzamide;
4-{1-[2-({(1E)-amino[(3-hydroxypropyl)amino]methylene}amino)-2-oxoethyl]-5-phenyl-1H-pyrrol-2-yl}-N-(2-hydroxyethyl)benzamide;
4-{1-[2-({(1E)-amino[(3-hydroxypropyl)amino]methylene}amino)-2-oxoethyl]-5-phenyl-1H-pyrrol-2-yl}-N-(2-cyanoethyl)benzamide;
4-{1-[2-({(1E)-amino[(3-hydroxypropyl)amino]methylene}amino)-2-oxoethyl]-5-phenyl-1H-pyrrol-2-yl}-N-propylbenzamide;
4-{1-[2-({(1E)-amino[(3-hydroxypropyl)amino]methylene}amino)-2-oxoethyl]-5-phenyl-1H-pyrrol-2-yl}-N-(2-methoxyethyl)benzamide;
4-{1-[2-({(1E)-amino[(3-hydroxypropyl)amino]methylene}amino)-2-oxoethyl]-5-phenyl-1H-pyrrol-2-yl}-N-(sec-butyl)benzamide;
N-allyl-4-{1-[2-({(1E)-amino[(3-hydroxypropyl)amino]methylene}amino)-2-oxoethyl]-5-phenyl-1H-pyrrol-2-yl}-N-methylbenzamide;
4-{1-[2-({(1E)-amino[(3-hydroxypropyl)amino]methylene}amino)-2-oxoethyl]-5-phenyl-1H-pyrrol-2-yl}-N-(2,2,3,3,3-pentafluoropropyl)benzamide;

N-{(1E)-amino[(3-cyanopropyl)amino]methylene}-2-[2-phenyl-5-(trans-4-propylcyclohexyl)-1H-pyrrol-1-yl]acetamide;

N-{(1E)-amino[(3-cyanopropyl)amino]methylene}-2-(2-cyclohexyl-5-phenyl-1H-pyrrol-1-yl)acetamide; or the tautomers thereof, the stereoisomers thereof or the pharmaceutically acceptable salts thereof.

Compounds of the invention may be prepared employing conventional methods that utilize readily available reagents and starting materials. The reagents used in the preparation of the compounds of this invention can be either commercially obtained or can be prepared by standard procedures described in the literature. Representative compounds of the present invention can be prepared using the following synthetic schemes. The skilled practitioner will know how to make use of variants of these reaction sequences, which in themselves are well known in the art. For example, compounds of formula I may be prepared by reacting an azole of formula II with a t-butyl bromoacetate derivative of formula V to give the azolylester of formula III and reacting said formula III ester with an aminoquanidine of formula IV to give the desired compound of formula I. The reaction is shown in flow diagram I.

FLOW DIAGRAM I

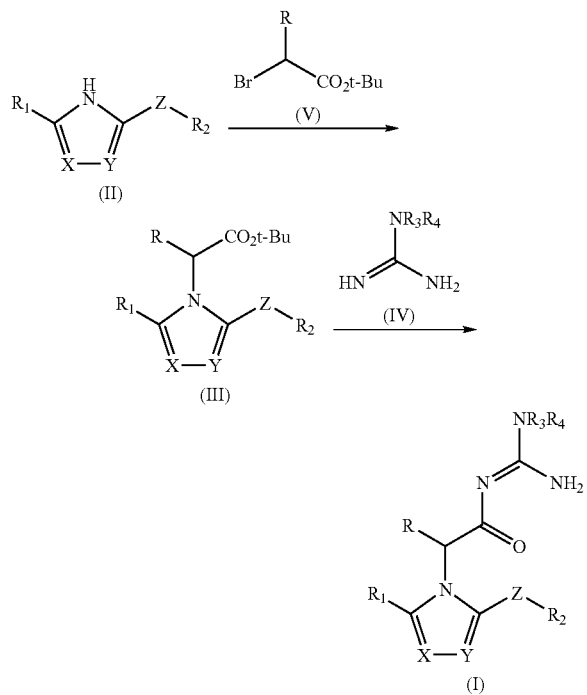

Compounds of formula I wherein R is H (I') may also be prepared by reacting an azolylacid of formula VI with an aminoquanidine of formula IV in the presence of a coupling agent such as 1,1'-carbonyldiimidazole (CDI). The reaction is shown in flow diagram II.

FLOW DIAGRAM II

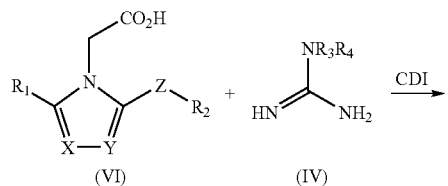

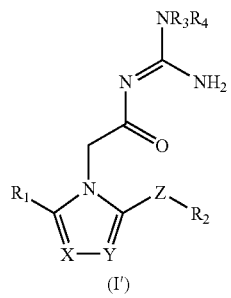

Compounds of formula VI wherein $R_1$ and $R_2$ are each independently phenyl; Z is $(CH_2)_n$; and n is 0 (VIa) may be prepared by reacting a diketone of formula VII with 1-aminoacetic acid in the presence of an acid catalyst such as p-toluenesulfonic acid (ptsa). The compound of formula VIa may then be converted to the corresponding compounds of formula Ia as shown hereinabove in flow diagram I. The reactions are illustrated in flow diagram III.

FLOW DIAGRAM III

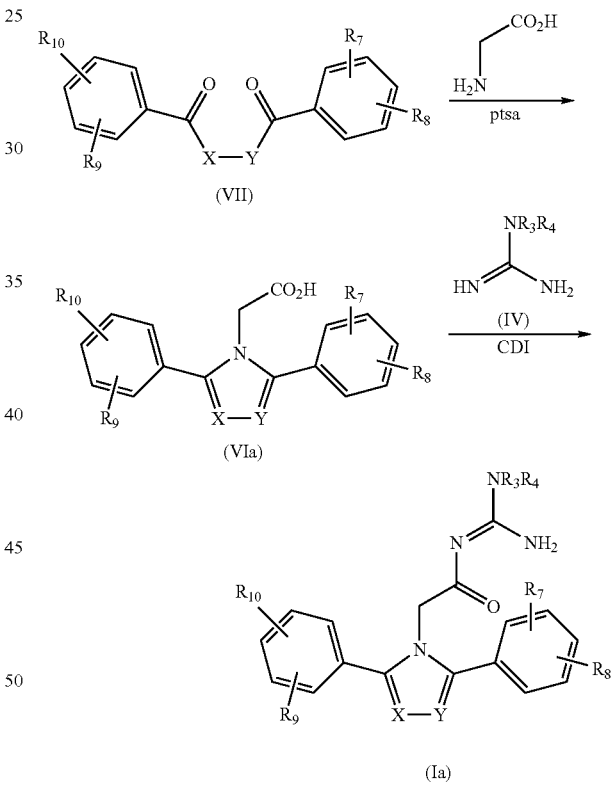

Alternatively, compounds of formula Ia may be prepared by reacting a 2-phenylazole of formula VIII with t-butyl 1-bromoacetate to give the corresponding 2-phenylazolyl ester of formula IX; brominating the formula IX ester with a brominating agent such as N-bromosuccinimide (NBS) to; give the 5-bromoazole derivative of formula X; and coupling the formula X compound with a boronic acid or ester of formula XI to give the intermediate compound of formula IIIa. Said formula IIIa intermediate may be converted to the desired compounds of formula Ia as described hereinabove in flow diagram I. The reactions are illustrated in flow diagram IV wherein R' represents H or alkyl.

FLOW DIAGRAM IV

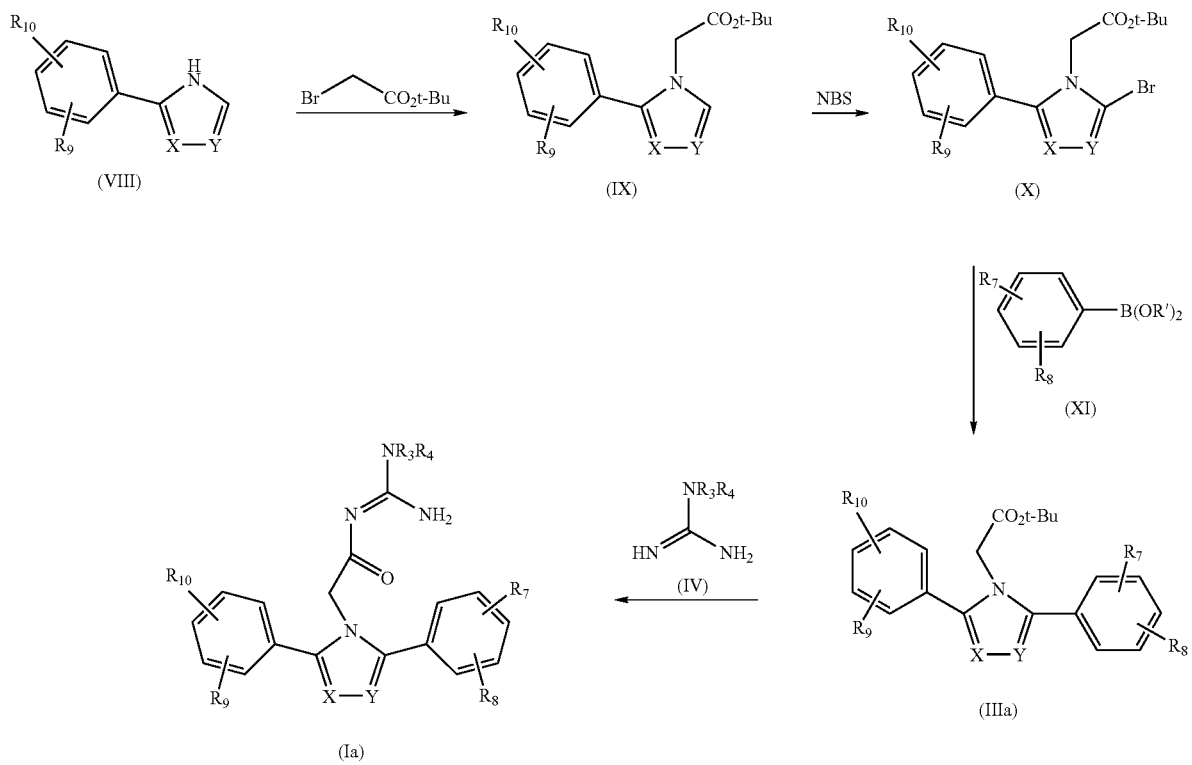

Compounds of formula I wherein Z is CO (Ib) may be prepared by reacting a substituted azole compound of formula XII with a pyridinylcarbothioate of formula XIII to give the azole of formula XIV; the formula XIV azole may be alkylated with a t-butyl 1-bromoacetate derivative of formula V and then converted to desired formula Ib product as shown hereinabove in flow diagram 1. Alternatively, the formula XIV compound may be reduced with a reducing agent such as NaBH$_4$ to give the compound of formula XV and said formula XV compound may be alkylated with the formula V bromoacetate and then converted to the compound of formula I wherein Z is CH$_2$ (Ic). The reactions are shown in flow diagram V.

FLOW DIAGRAM V

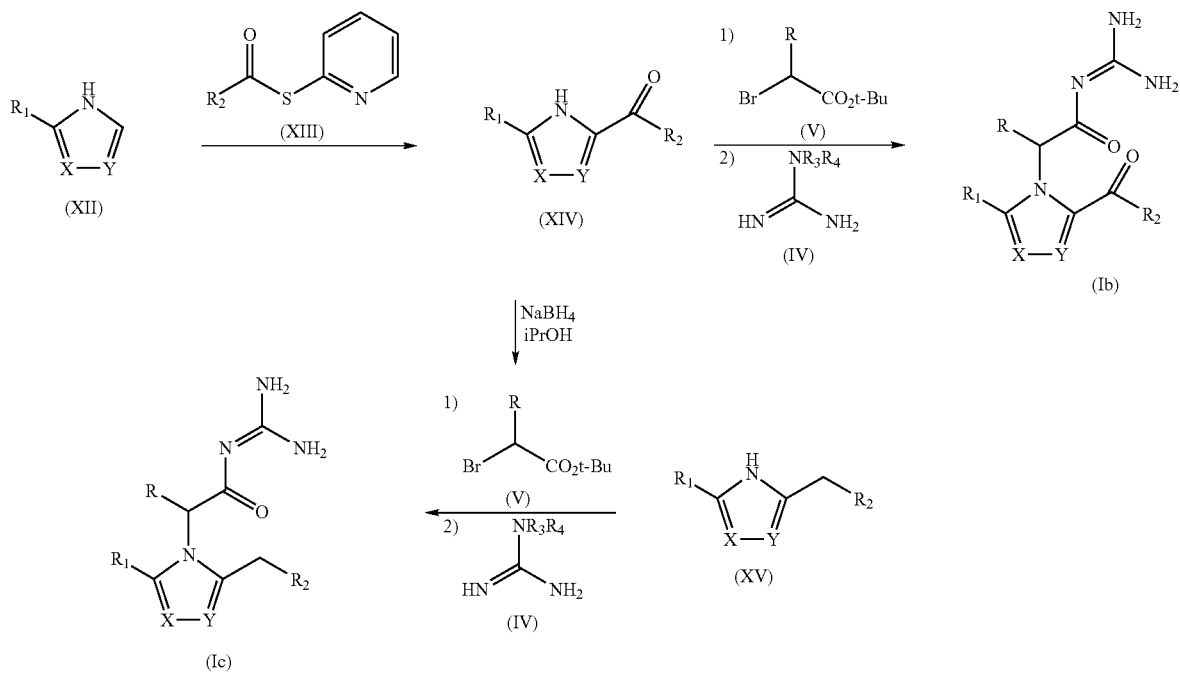

Advantageously, the compounds of the invention are useful for the treatment, prevention or amelioration of a disease or disorder characterized by elevated β-amyloid deposits or β-amyloid levels in a patient, including Alzheimer's disease, Downs Syndrome, Hereditary Cerebral Hemorrhage with Amyloidosis of the Dutch type or other neurodegenerative or dementia-inducing disorders. Accordingly, the present invention provides a method for the treatment, prevention or amelioration of a disease or disorder characterized by elevated β-amyloid deposits or β-amyloid levels in a patient which comprises providing said patient with a therapeutically effective amount of a compound of formula I as described hereinabove. The compound may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

As described herein, a therapeutically or prophylactically useful amount of a compound of the invention is that amount of a compound which alleviates the symptoms of the disease, e.g., AD, or which prevents the onset of symptoms, or the onset of more severe symptoms. The useful amounts of a compound may vary depending upon the formulation and route of delivery. For example, higher amounts may be delivered orally than when the compound is formulated for injection or inhalation, in order to deliver a biologically equivalent amount of the drug. Suitably, an individual dose (i.e., per unit) of a compound of the invention is in the range from about 1 μg/kg to about 10 g/kg. Desirably, these amounts are provided on a daily basis. However, the dosage to be used in the treatment or prevention of a specific cognitive deficit or other condition may be subjectively determined by the attending physician. The variables involved include the specific cognitive deficit and the size, age and response pattern of the patient. For example, based upon the activity profile and potency of the compounds of this invention, a starting dose of about 375 to 500 mg per day with gradual increase in the daily dose to about 1000 mg per day may provide the desired dosage level in the human.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

Alternatively, the use of sustained delivery devices may be desirable, in order to avoid the necessity for the patient to take medications on a daily basis. "Sustained delivery" is defined as delaying the release of an active agent, i.e., a compound of the invention, until after placement in a delivery environment, followed by a sustained release of the agent at a later time. Those of skill in the art know suitable sustained delivery devices. Examples of suitable sustained delivery devices include, e.g., hydrogels (see, e.g., U.S. Pat. Nos. 5,266,325; 4,959,217; and 5,292,515), an osmotic pump, such as described by Alza (U.S. Pat. Nos. 4,295,987 and 5,273,752) or Merck (European Patent No. 314,206), among others; hydrophobic membrane materials, such as ethylenemethacrylate (EMA) and ethylenevinylacetate (EVA); bioresorbable polymer systems (see, e.g., International Patent Publication No. WO 98/44964, Bioxid and Cellomeda; U.S. Pat. Nos. 5,756,127 and 5,854,388); other bioresorbable implant devices have been described as being composed of, for example, polyesters, polyanhydrides, or lactic acid/glycolic acid copolymers (see, e.g., U.S. Pat. No. 5,817,343 (Alkermes Inc.)). For use in such sustained delivery devices, the compounds of the invention may be formulated as described herein.

In another aspect, the invention provides a pharmaceutical kit for delivery of a product. Suitably, the kit contains packaging or a container with the compound formulated for the desired delivery route. For example, if the kit is designed for administration by inhalation, it may contain a suspension containing a compound of the invention formulated for aerosol or spray delivery of a predetermined dose by inhalation. Suitably, the kit contains instructions on dosing and an insert regarding the active agent. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of the spray pump or other delivery device.

Other suitable components to such kits will be readily apparent to one of skill in the art, taking into consideration the desired indication and the delivery route. The doses may be repeated daily, weekly, or monthly, for a predetermined length of time or as prescribed.

For a more clear understanding, and in order to illustrate the invention more clearly, specific examples thereof are set forth hereinbelow. The following examples are merely illustrative and are not to be understood as limiting the scope and underlying principles of the invention in any way. Indeed, various modifications of the invention, in addition to those shown and described herein, will become apparent to those skilled in the art from the examples set forth hereinbelow and the foregoing description. Such modifications are also intended to fall within the scope of the appended claims.

Unless otherwise noted, all parts are parts by weight. The terms HNMR and HPLC designate proton nuclear magnetic resonance and high performance liquid chromatography, respectively. The terms DMSO and DMF designate dimethylsulfoxide and N,N-dimethylformamide, respectively. MS designates mass spectroscopy, with (+) referring to the positive mode which generally gives a M+1 (or M+H) absorption wherein M represents the molecular mass. At the minimum, all compounds are analyzed by HPLC, MS and/or HNMR.

Commercially available reagents and solvents were used directly as received except for N-bromosuccinimide which was recrystallized from water. All procedures employing air- and/or moisture-sensitive reagents were conducted under an inert atmosphere in flame-dried glassware where appropriate. HNMR spectra were recorded in DMSO-$d_6$ on a Varian Inova spectrometer at 500 MHz, unless otherwise indicated.

EXAMPLE 1

Preparation of (N-(diaminomethylene)-2,4-diphenyl-1H-pyrrole-1-acetamide)

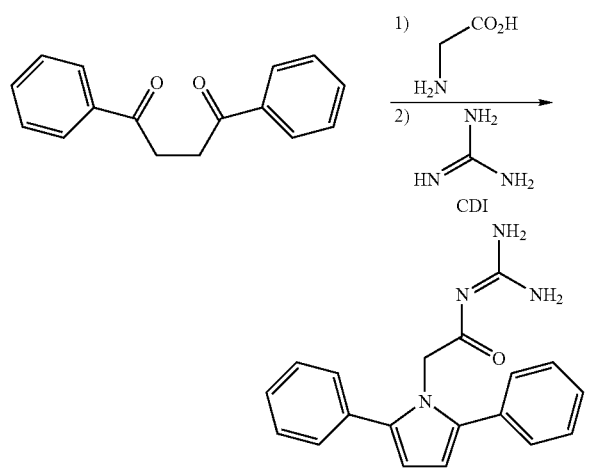

Step 1

A solution of 1,4-diphenyl-butane-1,4-dione (1 eq), glycine (3 eq.) and pTSA (0.05 eq) in ethanol is refluxed for 3 days. The mixture is cooled and the EtOH evaporated in vacuo. The residue is diluted with DCM and washed with NaOH (1 N). The aqueous phase is acidified with conc. HCl and extracted with EtOAc, dried over MgSO$_4$ and concentrated.

Step 2

To a solution of (2,5-diphenyl-pyrrol-1-yl)-acetic acid (1 eq.) in DMF is added CDI (1.2 eq.) and the mixture stirred at RT for 1 hour. Then add a solution of guanidine HCl (3 eq.) and triethylamine (3 eq.) in DMF is added. The reaction is stirred for 5 hours, then water is added and the mixture extracted with EtOAc, dried over MgSO4 and concentrated. The residue is dissolved in a mixture of DMSO, MeOH and water (1.5 mL total) and purified by Gilson preparative HPLC system. See Gilson Preparative HPLC conditions: Gilson Preparative HPLC system; YMC Pro C18, 20 mm×50 mm ID, 5 µM column; 2 mL injection; Solvent A: 0.02% TFA/water; Solvent B: 0.02% TFA/acetonitrile; Gradient: Time 0: 95% A; 2 min: 95% A; 14 min: 10% A, 15 min: 10% A, 16 min: 95% A; Flow rate 22.5 mL/min; Detection: 254 nm DAD.

EXAMPLES 2-7

Preparation of Derivatives of (N-(diaminomethylene)-2,4-diphenyl-1H-pyrrole-1-acetamide)

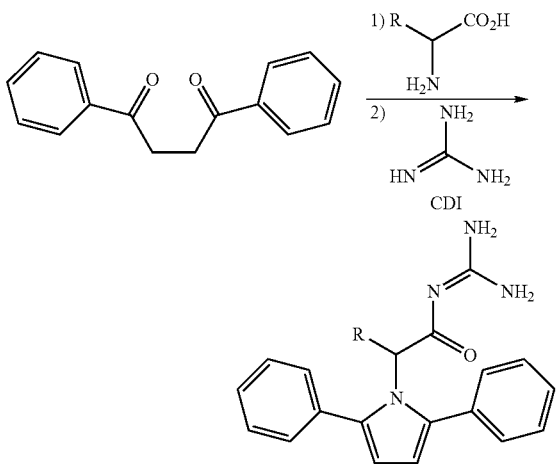

Using essentially the same procedure described in Example 1 and employing the appropriate amino acid, the compounds shown in Table I were prepared and identified by HPLC and mass spectral analyses. HPLC Conditions: HP 1100 HPLC system; Waters Xterra MS C18, 2 mm (i.d.)×50 mm (length), 3.5 µm column, set at 50° C.; Flow rate 1.0 mL/min; Solvent A: 0.02% formic acid in water; Solvent B 0.02% formic acid in ACN; Gradient: Time O: 10% B; 2.5 min 90% B; 3 min 90% B; Sample concentration: ~2.0 mM; Injection volume: 5 µL; Detection: 220 nm, 254 nm DAD.

TABLE I

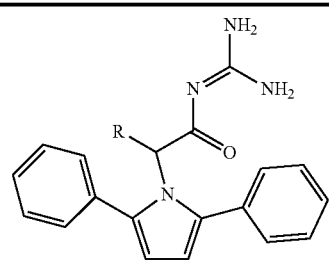

| Ex. No. | R | Observed Ion | HPLC (min) |
|---|---|---|---|
| 2 | n-Pr | 361 [M + H] | 2.21 |
| 3 | i-Bu | 375 [M + H] | 2.36 |
| 4 | CH$_2$CO$_2$H | 377 [M + H] | 1.80 |
| 5 | (CH$_2$)$_2$SCH$_3$ | 393 [M + H] | 2.12 |

TABLE I-continued

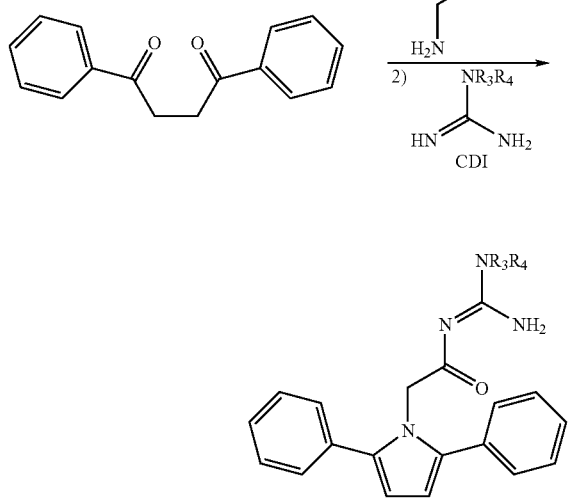

| Ex. No. | R | Observed Ion | HPLC (min) |
|---|---|---|---|
| 6 | 1-naphthyl-methyl | 459 [M + H] | 2.45 |
| 7 | $CH_2CO_2$-t-Bu | 433 [M + H] | 2.29 |

EXAMPLES 8-10

Preparation of 2,5-Dihenylpyrrole Acylguanidine Derivatives

Using essentially the same procedures described in Example 1 and employing the appropriate substituted guanidine in step 2, the compounds shown in Table II were prepared and identified by HPLC and mass spectral analyses. HPLC Conditions: HP 1100 HPLC system; Waters Xterra MS C18, 2 mm (i.d.)×50 mm (length), 3.5 μm column, set at 50° C.; Flow rate 1.0 mL/min; Solvent A: 0.02% formic acid in water; Solvent B 0.02% formic acid in ACN; Gradient: Time 0: 10% B; 2.5 min 90% B; 3 min 90% B; Sample concentration: ~2.0 mM; Injection volume: 5 μL; Detection: 220 nm, 254 nm DAD.

TABLE II

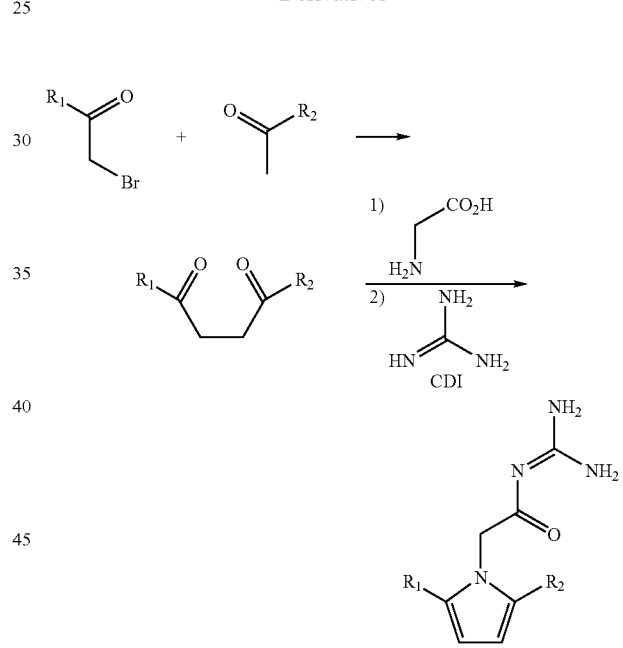

| Ex. No. | R3 | R4 | Observed Ion | HPLC (min) |
|---|---|---|---|---|
| 8 | $COCH_3$ | H | 361 [M + H] | 2.69 |
| 9 | $CH_2CH_2OCH_2CH_2$ | | 389 [M + H] | 2.14 |
| 10 | 4-$CH_3OC_6H_4$ | H | 425 [M + H] | 2.21 |

EXAMPLES 11-159

Preparation of 2,5-Diarylpyrrole Acylguanidine Derivatives

Step 1

To a solution of diethylamine (1.5 eq) and t-BuOH (1.5 eq) in toluene is added $ZnCl_2$ (Aldrich, anhydrous powder or beads). The mixture is stirred at RT for 2 hours until it is mostly dissolved. The acetophenone (1.5 eq) followed by the bromoacetophenone (1 eq) are added. The mixture is stirred for 3-5 days. Then 5% aqueous sulfuric acid is added. The product may precipitate and be filtered. Otherwise the phases are separated and the organic washed with aqueous sodium chloride, dried over $MgSO_4$ and concentrated in vacuo. See Kulinkovich, Synthesis 2000, 9, 1259-1262.

Step 2

A solution of 1,4-diaryl-butane-1,4-dione (1 eq), glycine (3 eq.) and pTSA (0.05 eq) in ethanol is refluxed for 3 days. The mixture is cooled and the EtOH evaporated in vacuo. The residue is diluted with DCM and washed with NaOH (1 N).

The aqueous phase is acidified with conc. HCl and extracted with EtOAc, dried over MgSO₄ and concentrated.

Step 3

To a solution of (2,5-diaryl-pyrrol-1-yl)-acetic acid (1 eq.) in DMF was aded CDI (1.2 eq.) and the mixture stirred at r.t. 1 hour. Then add a solution of guanidine HCl (3 eq.) and triethylamine (3 eq.) in DMF is added. The reaction is stirred for 5 hours, then water is added and the mixture extracted with EtOAc, dried over MgSO₄ and concentrated. The residue is dissolved in a mixture of DMSO, MeOH and water (1.5 mL total) and purified by Gilson preparative HPLC system. See Gilson Preparative HPLC conditions: Gilson Preparative HPLC system; YMC Pro C18, 20 mm×50 mm ID, 5 uM column; 2 mL injection; Solvent A: 0.02% TFA/water; Solvent B: 0.02% TFA/acetonitrile; Gradient: Time 0: 95% A; 2 min: 95% A; 14 min: 10% A, 15 min: 10% A, 16 min: 95% A; Flow rate 22.5 mL/min; Detection: 254 nm DAD. HPLC Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% formic acid in water; Solvent B 0.02% formic acid in ACN; Gradient: Time O: 10% B; 2.5 min 90% B; 3 min 90% B; Sample concentration: ~2.0 mM; Injection volume: 5 uL; Detection: 220 nm, 254 nm DAD.

Using the procedures described hereinabove in steps 1-3, the compounds shown in Table III were obtained and identified by HPLC, MS and NMR analyses. Table III, the term Ph designates phenyl, the term AC designates acetyl and the term Me designates methyl.

TABLE III

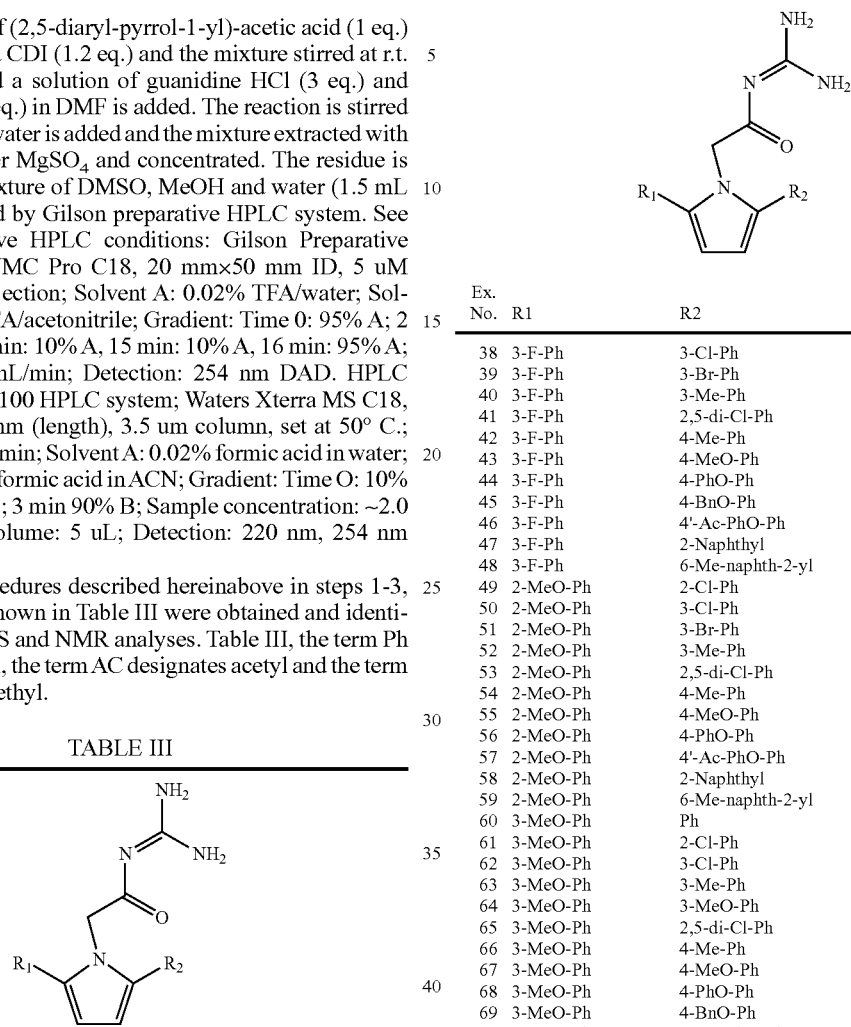

| Ex. No. | R1 | R2 | Observed Ion | HPLC (min) |
|---|---|---|---|---|
| 11 | Ph | 2-Cl-Ph | 351 [M − H] | 2.31 |
| 12 | Ph | 3-Cl-Ph | 351 [M − H] | 2.36 |
| 13 | Ph | 3-F-Ph | 335 [M − H] | 2.27 |
| 14 | Ph | 3-Br-Ph | 396 [M − H] | 2.39 |
| 15 | Ph | 3-Me-Ph | 331 [M − H] | 2.33 |
| 16 | Ph | 2,5-di-Cl-Ph | 386 [M − H] | 2.43 |
| 17 | Ph | 4-Me-Ph | 333 [M + H] | 2.24 |
| 18 | Ph | 4-MeO-Ph | 349 [M + H] | 2.24 |
| 19 | Ph | 4-PhO-Ph | 409 [M − H] | 2.53 |
| 20 | Ph | 4-BnO-Ph | 423 [M − H] | 2.53 |
| 21 | Ph | 4'-Ac-PhO-Ph | 451 [M − H] | 2.44 |
| 22 | Ph | 2-Naphthyl | 367 [M − H] | 2.44 |
| 23 | Ph | 6-Me-naphth-2-yl | 383 [M + H] | 2.56 |
| 24 | 2-Cl-Ph | 2-Cl-Ph | 388 [M + H] | 2.37 |
| 25 | 2-Cl-Ph | 3-Cl-Ph | 388 [M + H] | 2.42 |
| 26 | 2-Cl-Ph | 3-Br-Ph | 433 [M + H] | 2.45 |
| 27 | 2-Cl-Ph | 3-Me-Ph | 367 [M + H] | 2.39 |
| 28 | 2-Cl-Ph | 2,5-di-Cl-Ph | 422 [M + H] | 2.48 |
| 29 | 2-Cl-Ph | 4-Me-Ph | 367 [M + H] | 2.4 |
| 30 | 2-Cl-Ph | 4-PhO-Ph | 445 [M + H] | 2.57 |
| 31 | 2-Cl-Ph | 4-BnO-Ph | 459 [M + H] | 2.57 |
| 32 | 2-Cl-Ph | 4'-Ac-PhO-Ph | 487 [M + H] | 2.49 |
| 33 | 2-Cl-Ph | 2-Naphthyl | 403 [M + H] | 2.49 |
| 34 | 2-Cl-Ph | 6-Me-naphth-2-yl | 417 [M + H] | 2.58 |
| 35 | 3-Cl-Ph | 4-PhO-Ph | 445 [M + H] | 3.2 |
| 36 | 3-Cl-Ph | 3-Br-4-NHAc-Ph | 489 [M + H] | 1.98 |
| 37 | 3-F-Ph | 2-Cl-Ph | 369 [M − H] | 2.34 |
| 38 | 3-F-Ph | 3-Cl-Ph | 369 [M − H] | 2.39 |
| 39 | 3-F-Ph | 3-Br-Ph | 417 [M + H] | 2.41 |
| 40 | 3-F-Ph | 3-Me-Ph | 349 [M − H] | 2.36 |
| 41 | 3-F-Ph | 2,5-di-Cl-Ph | 406 [M + H] | 2.43 |
| 42 | 3-F-Ph | 4-Me-Ph | 349 [M − H] | 2.36 |
| 43 | 3-F-Ph | 4-MeO-Ph | 365 [M − H] | 2.28 |
| 44 | 3-F-Ph | 4-PhO-Ph | 427 [M − H] | 2.54 |
| 45 | 3-F-Ph | 4-BnO-Ph | 441 [M − H] | 2.54 |
| 46 | 3-F-Ph | 4'-Ac-PhO-Ph | 469 [M − H] | 2.46 |
| 47 | 3-F-Ph | 2-Naphthyl | 385 [M − H] | 2.46 |
| 48 | 3-F-Ph | 6-Me-naphth-2-yl | 399 [M − H] | 2.55 |
| 49 | 2-MeO-Ph | 2-Cl-Ph | 383 [M + H] | 2.35 |
| 50 | 2-MeO-Ph | 3-Cl-Ph | 383 [M + H] | 2.37 |
| 51 | 2-MeO-Ph | 3-Br-Ph | 428 [M + H] | 2.39 |
| 52 | 2-MeO-Ph | 3-Me-Ph | 363 [M + H] | 2.35 |
| 53 | 2-MeO-Ph | 2,5-di-Cl-Ph | 418 [M + H] | 2.44 |
| 54 | 2-MeO-Ph | 4-Me-Ph | 363 [M + H] | 2.36 |
| 55 | 2-MeO-Ph | 4-MeO-Ph | 379 [M + H] | 2.28 |
| 56 | 2-MeO-Ph | 4-PhO-Ph | 441 [M + H] | 2.54 |
| 57 | 2-MeO-Ph | 4'-Ac-PhO-Ph | 483 [M + H] | 2.46 |
| 58 | 2-MeO-Ph | 2-Naphthyl | 399 [M + H] | 2.45 |
| 59 | 2-MeO-Ph | 6-Me-naphth-2-yl | 413 [M + H] | 2.55 |
| 60 | 3-MeO-Ph | Ph | 349 [M + H] | 2.24 |
| 61 | 3-MeO-Ph | 2-Cl-Ph | 383 [M + H] | 2.32 |
| 62 | 3-MeO-Ph | 3-Cl-Ph | 383 [M + H] | 2.36 |
| 63 | 3-MeO-Ph | 3-Me-Ph | 363 [M + H] | 2.33 |
| 64 | 3-MeO-Ph | 3-MeO-Ph | | |
| 65 | 3-MeO-Ph | 2,5-di-Cl-Ph | 418 [M + H] | 2.42 |
| 66 | 3-MeO-Ph | 4-Me-Ph | 363 [M + H] | 2.33 |
| 67 | 3-MeO-Ph | 4-MeO-Ph | 379 [M + H] | 2.25 |
| 68 | 3-MeO-Ph | 4-PhO-Ph | 441 [M + H] | 2.52 |
| 69 | 3-MeO-Ph | 4-BnO-Ph | 455 [M + H] | 2.52 |
| 70 | 3-MeO-Ph | 4'-Ac-PhO-Ph | 483 [M + H] | 2.44 |
| 71 | 3-MeO-Ph | 2-Naphthyl | 399 [M + H] | 2.43 |
| 72 | 3-MeO-Ph | 6-Me-naphth-2-yl | 413 [M + H] | 2.52 |
| 73 | 3-CN-Ph | Ph | 344 [M + H] | 2.19 |
| 74 | 3-CN-Ph | 2-Cl-Ph | 378 [M + H] | 2.26 |
| 75 | 3-CN-Ph | 3-Cl-Ph | 378 [M + H] | 2.31 |
| 76 | 3-CN-Ph | 3-Br-Ph | 423 [M + H] | 2.33 |
| 77 | 3-CN-Ph | 3-Me-Ph | 358 [M + H] | 2.28 |
| 78 | 3-CN-Ph | 2,5-di-Cl-Ph | 413 [M + H] | 2.37 |
| 79 | 3-CN-Ph | 4-Me-Ph | 358 [M + H] | 2.28 |
| 80 | 3-CN-Ph | 4-MeO-Ph | 374 [M + H] | 2.2 |
| 81 | 3-CN-Ph | 4-PhO-Ph | 436 [M + H] | 2.47 |
| 82 | 3-CN-Ph | 4-BnO-Ph | 450 [M + H] | 2.47 |
| 83 | 3-CN-Ph | 4'-Ac-PhO-Ph | 478 [M + H] | 2.39 |
| 84 | 3-CN-Ph | 2-Naphthyl | 394 [M + H] | 2.38 |
| 85 | 3-CN-Ph | 6-Me-naphth-2-yl | 408 [M + H] | 2.48 |
| 86 | 4-F-Ph | Ph | 335 [M − H] | 2.26 |
| 87 | 4-F-Ph | 2-Cl-Ph | 369 [M + H] | 2.33 |
| 88 | 4-F-Ph | 3-Cl-Ph | 369 [M + H] | 2.38 |
| 89 | 4-F-Ph | 3-Br-Ph | 416 [M + H] | 2.4 |
| 90 | 4-F-Ph | 3-Me-Ph | 349 [M − H] | 2.35 |
| 91 | 4-F-Ph | 2,5-di-Cl-Ph | 404 [M + H] | 2.44 |
| 92 | 4-F-Ph | 4-Me-Ph | 349 [M − H] | 2.35 |
| 93 | 4-F-Ph | 4-MeO-Ph | 365 [M + H] | 2.27 |
| 94 | 4-F-Ph | 4-PhO-Ph | 427 [M − H] | 2.53 |
| 95 | 4-F-Ph | 4-BnO-Ph | 443 [M + H] | 2.58 |
| 96 | 4-F-Ph | 4'-Ac-PhO-Ph | 469 [M − H] | 2.45 |
| 97 | 4-F-Ph | 2-Naphthyl | 387 [M + H] | 1.99 |
| 98 | 4-F-Ph | 6-Me-naphth-2-yl | 399 [M − H] | 2.54 |
| 99 | 4-MeO-Ph | 2-Cl-Ph | 383 [M + H] | 2.32 |
| 100 | 4-MeO-Ph | 3-Cl-Ph | 383 [M + H] | 2.36 |

TABLE III-continued

| Ex. No. | R1 | R2 | Observed Ion | HPLC (min) |
|---|---|---|---|---|
| 101 | 4-MeO-Ph | 3-Br-Ph | 428 [M + H] | 2.39 |
| 102 | 4-MeO-Ph | 3-Me-Ph | 363 [M + H] | 2.33 |
| 103 | 4-MeO-Ph | 2,5-di-Cl-Ph | 418 [M + H] | 2.42 |
| 104 | 4-MeO-Ph | 4-Me-Ph | 363 [M + H] | 2.33 |
| 105 | 4-MeO-Ph | 4-MeO-Ph | 379 [M + H] | 2.18 |
| 106 | 4-MeO-Ph | 4-PhO-Ph | 441 [M + H] | 2.52 |
| 107 | 4-MeO-Ph | 4'-Ac-PhO-Ph | 483 [M + H] | 2.44 |
| 108 | 4-MeO-Ph | 2-Naphthyl | 399 [M + H] | 2.44 |
| 109 | 4-MeO-Ph | 6-Me-naphth-2-yl | 413 [M + H] | 2.54 |
| 110 | 4-Me-Ph | 2-Cl-thien-5-yl | 373 [M + H] | 2.15 |
| 111 | 4-CF3-Ph | Ph | 387 [M + H] | 2.39 |
| 112 | 4-CF3-Ph | 2-Cl-Ph | 421 [M + H] | 2.45 |
| 113 | 4-CF3-Ph | 3-Cl-Ph | 421 [M + H] | 2.49 |
| 114 | 4-CF3-Ph | 3-Br-Ph | 465 [M + H] | 2.51 |
| 115 | 4-CF3-Ph | 3-Me-Ph | 401 [M + H] | 2.47 |
| 116 | 4-CF3-Ph | 2,5-di-Cl-Ph | 456 [M + H] | 2.54 |
| 117 | 4-CF3-Ph | 4-Me-Ph | 401 [M + H] | 2.47 |
| 118 | 4-CF3-Ph | 4-MeO-Ph | 417 [M + H] | 2.4 |
| 119 | 4-CF3-Ph | 4-PhO-Ph | 479 [M + H] | 2.62 |
| 120 | 4-CF3-Ph | 4-BnO-Ph | 493 [M + H] | 2.62 |
| 121 | 4-CF3-Ph | 4'-Ac-PhO-Ph | 521 [M + H] | 2.22 |
| 122 | 4-CF3-Ph | 2-Naphthyl | 437 [M + H] | 2.55 |
| 123 | 4-CF3-Ph | 6-Me-naphth-2-yl | 451 [M + H] | 2.63 |
| 124 | 4-CF3O-Ph | 4-EtO2C-Ph | 475 [M + H] | 2.33 |
| 125 | 2,5-di-MeO-Ph | Ph | 379 [M + H] | 2.25 |
| 126 | 2,5-di-MeO-Ph | 2-Cl-Ph | 413 [M + H] | 2.36 |
| 127 | 2,5-di-MeO-Ph | 3-Cl-Ph | 413 [M + H] | 2.35 |
| 128 | 2,5-di-MeO-Ph | 3-Br-Ph | 458 [M + H] | 2.38 |
| 129 | 2,5-di-MeO-Ph | 3-Me-Ph | 393 [M + H] | 2.34 |
| 130 | 2,5-di-MeO-Ph | 2,5-di-Cl-Ph | 448 [M + H] | 2.44 |
| 131 | 2,5-di-MeO-Ph | 4-Me-Ph | 393 [M + H] | 2.35 |
| 132 | 2,5-di-MeO-Ph | 4-MeO-Ph | 409 [M + H] | 2.29 |
| 133 | 2,5-di-MeO-Ph | 4-PhO-Ph | 471 [M + H] | 2.53 |
| 134 | 2,5-di-MeO-Ph | 4-BnO-Ph | 485 [M + H] | 3.08 |
| 135 | 2,5-di-MeO-Ph | 4'-Ac-PhO-Ph | 513 [M + H] | 2.44 |
| 136 | 2,5-di-MeO-Ph | 2-Naphthyl | 429 [M + H] | 2.44 |
| 137 | 2,5-di-MeO-Ph | 6-Me-naphth-2-yl | 443 [M + H] | 2.54 |
| 138 | 1-Naphthyl | Ph | 369 [M + H] | 2.44 |
| 139 | 1-Naphthyl | 2-Cl-Ph | 403 [M + H] | 2.52 |
| 140 | 1-Naphthyl | 3-Cl-Ph | 403 [M + H] | 2.36 |
| 141 | 1-Naphthyl | 3-Br-Ph | 448 [M + H] | 2.58 |
| 142 | 1-Naphthyl | 3-Me-Ph | 383 [M + H] | 2.29 |
| 143 | 1-Naphthyl | 2,5-di-Cl-Ph | 438 [M + H] | 2.6 |
| 144 | 1-Naphthyl | 4-Me-Ph | 383 [M + H] | 2.38 |
| 145 | 1-Naphthyl | 4-MeO-Ph | 399 [M + H] | 2.41 |
| 146 | 1-Naphthyl | 2-Naphthyl | 419 [M + H] | 2.58 |
| 147 | 2-Naphthyl | 3-MeO-Ph | 399 [M + H] | 2.25 |
| 148 | 2-Naphthyl | 3,5-di-CF3-Ph | 505 [M + H] | 2.54 |
| 149 | Benzothiophen-3-yl | 2-Cl-Ph | 409 [M + H] | 2.49 |
| 150 | Benzothiophen-3-yl | 3-Cl-Ph | 409 [M + H] | 2.52 |
| 151 | Benzothiophen-3-yl | 3-Br-Ph | 454 [M + H] | 2.56 |
| 152 | Benzothiophen-3-yl | 3-Me-Ph | 389 [M + H] | 2.5 |
| 153 | Benzothiophen-3-yl | 4-MeO-Ph | 405 [M + H] | 2.42 |
| 154 | Benzothiophen-3-yl | 4-BnO-Ph | 481 [M + H] | 2.66 |
| 155 | Benzothiophen-3-yl | 4'-Ac-PhO-Ph | 509 [M + H] | 2.52 |
| 156 | Benzothiophen-3-yl | 2-Naphthyl | 425 [M + H] | 2.59 |
| 157 | Benzothiophen-2-yl | 3,5-di-CF3-Ph | 511 [M + H] | 2.48 |
| 158 | 3-Ph-isoxazol-5-yl | 4-PhO-Ph | 478 [M + H] | 2.41 |
| 159 | 3-Ph-isoxazol-5-yl | 3-Br-4-NHAc-Ph | 522 [M + H] | 1.94 |

EXAMPLE 160

Preparation of 4-[1-(2-{[amino(imino)methyl]amino}-2-oxoethyl)-5-phenyl-1H-pyrrol-2-yl]-N-benzyl-N-methylbenzamide)

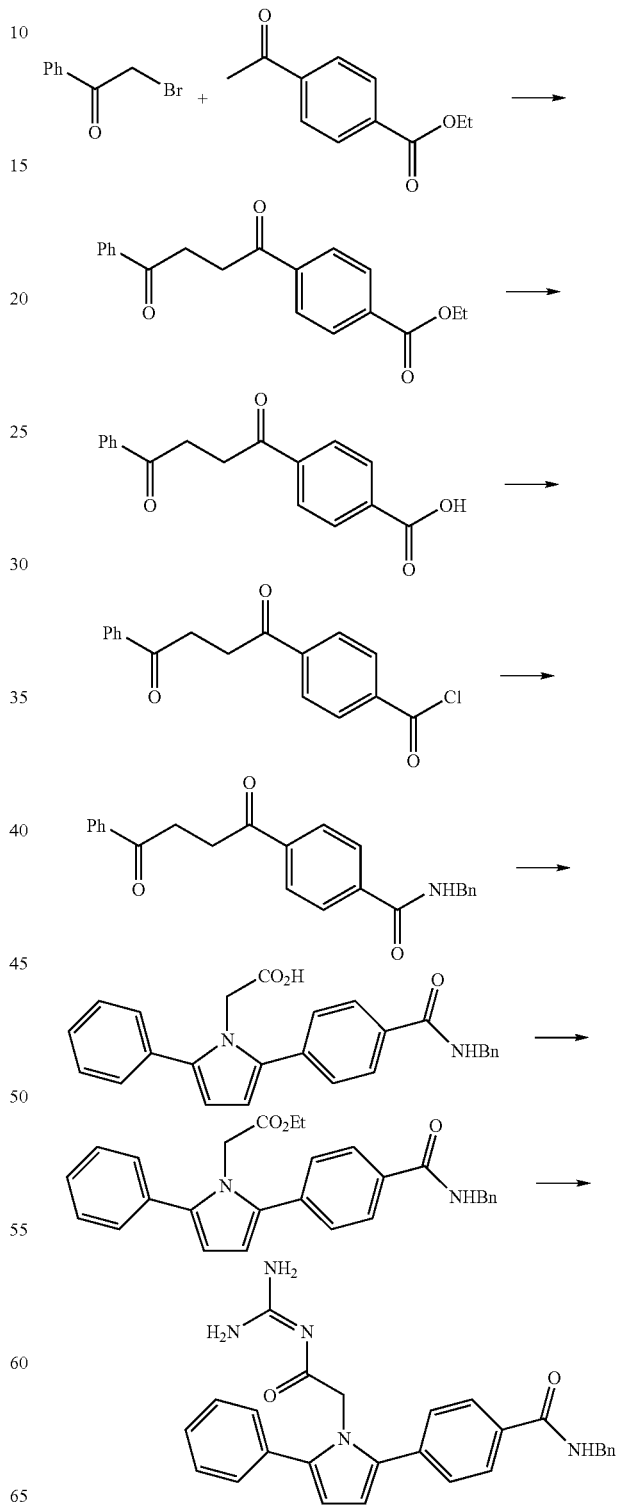

Step 1: 4-(4-Oxo-4-phenyl-butyryl)-benzoic acid ethyl ester 4-(4-Oxo-4-phenyl-butyryl)-benzoic acid ethyl ester is prepared from bromoacetophenone and ethyl 4-acetyl-benzoate and following the procedure in Example 11, Step 1.

Step 2: 4-(4-Oxo-4-phenyl-butyryl)-benzoic acid 4-(4-Oxo-4-phenyl-butyryl)-benzoic acid ethyl ester (3.22 g, 10.4 mmol) is dissolved in THF (100 mL) and an aqueous solution of KOH (15.6 mmol in 50 mL) is added. The reaction is stirred and heated (65° C.) for 6 h, whereupon HPLC analysis indicated the formation of a single product at the expense of the diketone. The reaction is neutralized with aqueous HCl and the THF removed in vacuo. The resulting solid is dissolved in EtOAc and the organic phase dried (Na$_2$SO$_4$), filtered and concentrated to afford 2.93 g (>99%) of the desired carboxylic acid (R$_f$=0.90). LCMS confirmed the identity of the product (ES+Exact Mass: 282.09, Obs.: 283.48). This product is used without further purification.

Step 3: 4-(4-Oxo-4-phenyl-butyryl)-benzoyl chloride

To a stirred slurry of the acid (1.98 g, 7 mmol) in CH$_2$Cl$_2$ (30 mL) is added oxalyl chloride (1.84 mL, 21 mmol) followed by the addition of a catalytic amount of DMF (~20 μL). Upon the addition of the oxalyl chloride, the reaction became homogeneous. The reaction is covered and stirred at room temperature. After 2 h, an aliquot from the reaction is concentrated and treated with piperidine and a single product w is observed, indicating that the acid had been completely activated to the acid chloride. The reaction is concentrated to dryness to afford a yellow solid. The solid is dissolved in CHCl$_3$ and concentrated to dryness and used without further purification.

Step 4: N-Benzyl-N-methyl-4-(4-oxo-4-phenyl-butyryl)-benzamide

Benzylmethylamine (220 μmol) is added to a 2-dram vial and dissolved in CH$_2$Cl$_2$ (2 mL) followed by the addition of TEA (40 μL). The acid chloride core (200 μmol) is dissolved in CH$_2$Cl$_2$ (1 mL) and the solution is added to the amines. The reactions sit at room temperature without agitation, overnight. Water is added and removed (2×1 mL) and upon the final water wash the organic phase is transferred to a clean vial and concentrated.

Step 5: {2-[4-(Benzyl-methyl-carbamoyl)-phenyl]-5-phenyl-pyrrol-1-yl}-acetic acid The resulting residue is dissolved in glacial acetic acid (1 mL) and glycine (30 mg, 400 μmol) is added in one portion as a solid using a solid dispenser. The vial is capped and heated (105-110° C.) for 3 h. LCMS analysis indicates that the pyrrole formation is complete. The reaction is concentrated at reduced pressure (35° C.) for 12 h. The resulting residue is dissolved in EtOAc (2 ml) and washed with H$_2$O (3×1 mL). The organic phase is transferred to a clean vial and concentrated.

Step 6: {2-[4-(Benzyl-methyl-carbamoyl)-phenyl]-5-phenyl-pyrrol-1-yl}-acetic acid ethyl ester The resulting residue is dissolved in MeOH (1 mL) and a methanolic HCl solution (TMSCl (1 mL) added to MeOH (35 mL) with stirring) (1 mL) is added. The vial is capped and heated (65° C.) for 16 h. LCMS analysis indicates that the ester is the predominate product. The reaction is concentrated in vacuo.

Step 7: 4-[1-(2-{[amino(imino)methyl]amino}-2-oxoethyl)-5-phenyl-1H-pyrrol-2-yl]-N-benzyl-N-methylbenzamide To the ester from step 6 (200 μmol) is disslved in DMSO (1 mL) and a solution of neutralized guanidine in DMSO is added (500 μL, 2 M in DMSO) and allowed to sit at room temperature for 16 h. The reaction is quenched by the addition of glacial AcOH (100 μL) and distilled water (200 μL) and concentrated in vacuo. The residue is dissolved in a mixture of DMSO, MeOH and water (1.5 mL total) and purified by Gilson preparative HPLC system.

EXAMPLES 161-185

Preparation of 5-Phenyl-2-(4-amidophenyl)pyrrole Acylguanidine Derivatives

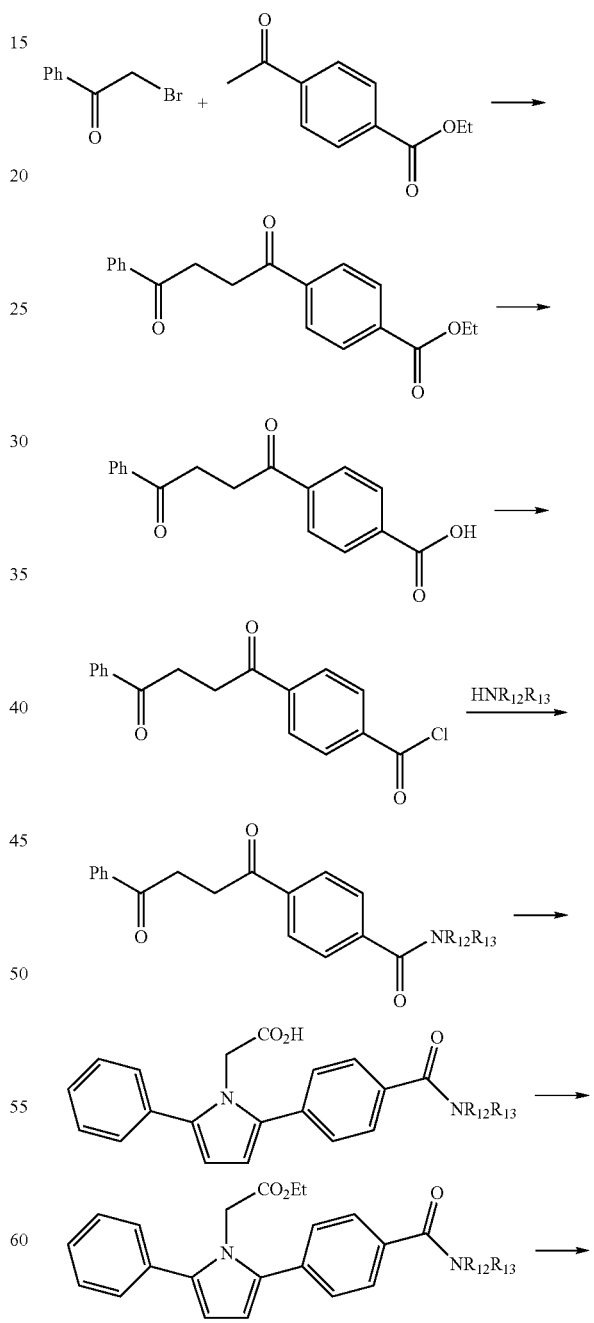

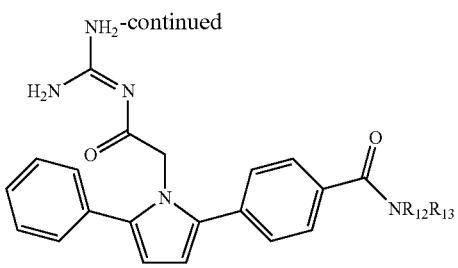

Using essentially the same procedures described in Example 160 and employing the appropriate amine is step 4, the compounds shown in Table IV were prepared and identified by HPLC and mass spectral analyses. HPLC Conditions: ZMD (Waters) or Platform (Micromass) or LCZ (Micromass) HPLC system: Zorbax SB-C8; Flow rate 3.0 mL/min; Solvent A: 0.1% TFA in water; Solvent B 0.1% TFA in ACN; Gradient: Time 0: 15% B; 2.5 min 95% B; Detection: ELSD detection (SEDEX 55); UV 253 detection (Schimadzu)

TABLE IV

| Ex. No. | NR12R13 | Observed Ion | HPLC (min) |
|---|---|---|---|
| 160 | benzylmethylamine | 466.16 | 0.81 |
| 161 | diethylamine | 418.18 | 0.72 |
| 162 | 2,5-dihydro-1H-pyrrole | 415.1 | 0.68 |
| 163 | piperidine | 430.19 | 0.74 |
| 164 | morpholine | 432.13 | 0.62 |
| 165 | homopiperidine | 444.21 | 0.78 |
| 166 | pyrrolidine | 416.16 | 0.67 |
| 167 | thiomorpholine | 449.11 | 0.71 |
| 168 | dimethylamine | 390.15 | 0.63 |
| 169 | Thiazolidine | 434.09 | 0.71 |
| 170 | 4-methylpiperidine | 444.19 | 0.8 |
| 171 | cis-2,6-dimethyl-piperidine | 458.19 | 0.82 |
| 172 | Cyclopropylmethyl-propyl-amine | 458.19 | 0.83 |
| 173 | 4-benzylpiperidine | 520.14 | 0.92 |
| 174 | 3,5-dimethyl-piperidine | 458.18 | 0.85 |
| 175 | 3-hydroxy-pyrrolidine | 432.13 | 0.57 |
| 176 | 2,5-dihydro-2,5-dimethyl-1H-pyrrole | 442.2 | 0.76 |
| 177 | ethyl-methylamine | 404.15 | 0.44 |
| 178 | di-iso-butylamine | 474.23 | 0.9 |
| 179 | 3-hydroxypiperidine | 446.15 | 0.6 |
| 180 | 2-methylpyrrolidine | 431.12 | 0.73 |
| 181 | methyl-2-methoxyethyl-amine | 434.18 | 0.65 |
| 182 | iso-propyl-2-methoxyethyl-amine | 462.2 | 0.74 |
| 183 | iso-butyl-methylamine | 432.2 | 0.76 |
| 184 | (S)-3-hydroxy-pyrrolidine | 432.13 | 0.56 |
| 185 | 4-n-propyl-piperidine | 473.13 | 0.92 |

EXAMPLE 186

Preparation of (N-[amino(imino)methyl]-2-[2-phenyl-5-(4-piperidin-1-ylphenyl)-1H-pyrrol-1-yl]acetamide)

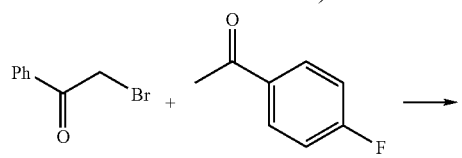

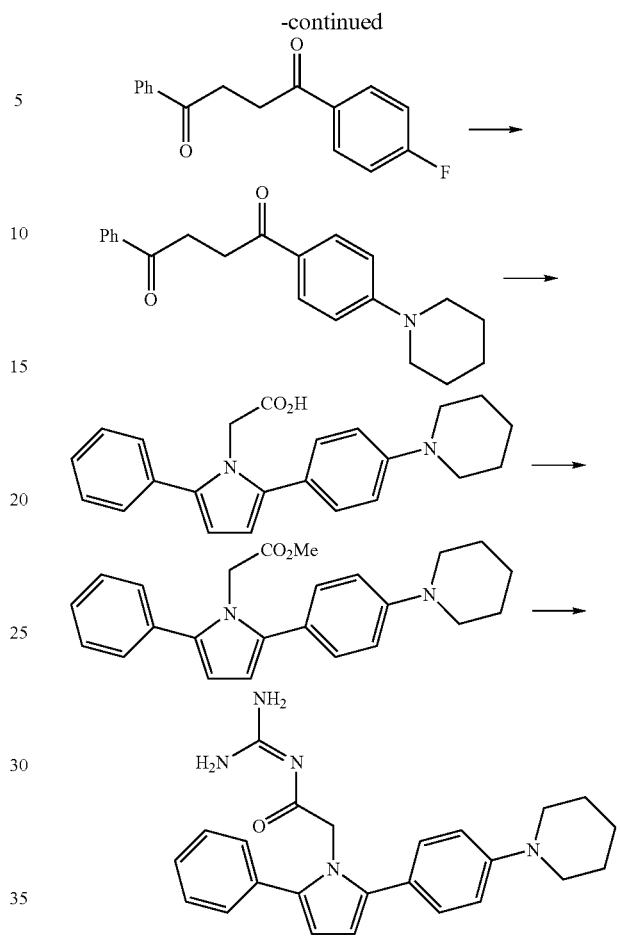

Step 1: 1-(4-Fluoro-phenyl)-4-phenyl-butane-1,4-dione

Diethylamine (55 mmol, 5.69 mL) and t-Butanol (55 mmol, 5.26 mL) are added to a stirred solution of Zinc Chloride (74 mmol, 10 g) in anhydrous toluene (100 mL). After two hours of stirring at room temperature, Zinc Chloride is completely dissolved. 1-(4-Fluorophenyl)-ethanone (40 mmol, 4.90 mL) is added, followed by the addition of bromoacetophenone (37 mmol, 7.4 g). The reaction is allowed to stir at room temperature for 3 days. A 5% aqueous solution of sulfuric acid (75 mL) is added and the organic phase is separated from the aqueous phase. The aqueous phase is extracted with Ethyl Acetate (50 mL) and the two organic phases are combined. The organic phase is dried with Sodium Sulfate, filtered and concentrated to give 1-(4-fluoro-phenyl)-4-phenyl-butane-1,4-dione (5.2 g) confirmed by LCMS, as a white solid.

Step 2: 1-Phenyl-4-(4-piperidin-1-yl-phenyl)-butane-1,4-dione 1-(4-Fluoro-phenyl)-4-phenyl-butane-1,4-dione (390 mmol, 100 mg) and piperdine (3.9 mmol, 0.34 mL) are dissolved in DMSO (100 uL) in a vial. The vial is capped and allowed to heat/shake at 110° overnight. After which time, the reaction is checked by HPLC. After the reaction cooled to room temperature, 500 uL of water is added. The product precipitates and is filtered. 74 mg is collected and confirmed by LCMS.

Step 3: [2-Phenyl-5-(4-piperidin-1-yl-phenyl)-pyrrol-1-yl]-acetic acid

Acetic Acid (251 mmol, 15 mg) is added to 1-phenyl-4-(4-piperidin-1-yl-phenyl)-butane-1,4-dione (228 mmol, 74 mg) and dissolved in 100 uL of DMSO. The reaction is capped and allowed to heat/shake at 110° C. overnight. The reaction is extracted with Ethyl Acetate (2×2 mL), dried with Sodium Sulfate, filtered and concentrated. The product is confirmed by LCMS.

Step 4: [2-Phenyl-5-(4-piperidin-1-yl-phenyl)-pyrrol-1-yl]-acetic acid methyl ester Chlorotrimethylsilane (275 mmol, 35 uL) is added dropwise to a cooled (0° C.) solution of [2-phenyl-5-(4-piperidin-1-yl-phenyl)-pyrrol-1-yl]-acetic acid (228 mmol) in methanol (anhydrous, 150 uL). The reaction is capped and allowed to heat/shake overnight at 65° C. The reaction is concentrated purified by flash chromatography over silica gel (3:1 methanol:methylene chloride). 64 mg of isolated product is confirmed by LCMS.

Step 5: N-{2-[2-Phenyl-5-(4-piperidin-1-yl-phenyl)-pyrrol-1-yl]-acetyl}-guanidine Guanidine HCl (700 mmol, 66.5 mg) is dissolved in 1 mL of 0.5M NaOMe/methanol solution and rotated to dryness. The residue is subsequently dissolved in 400 uL dry DMSO. A white NaCl precipitate remained and the supernatant (free guanidine base in solution) is added to a vial containing [2-phenyl-5-(4-piperidin-1-yl-phenyl)-pyrrol-1-yl]-acetic acid methyl ester (170 mmol, 64 mg). The solution is agitated in a shaker at room temperature. The reaction is quenched with excess AcOH (75 uL), concentrated in vacuo. The residue is dissolved in a mixture of DMSO, MeOH and water (1.5 mL total) and purified by Gilson preparative HPLC system.

EXAMPLES 187 AND 188

Preparation of 5-Phenyl-2-(4-aminophenyl)pyrrole Acylguanidine Derivatives

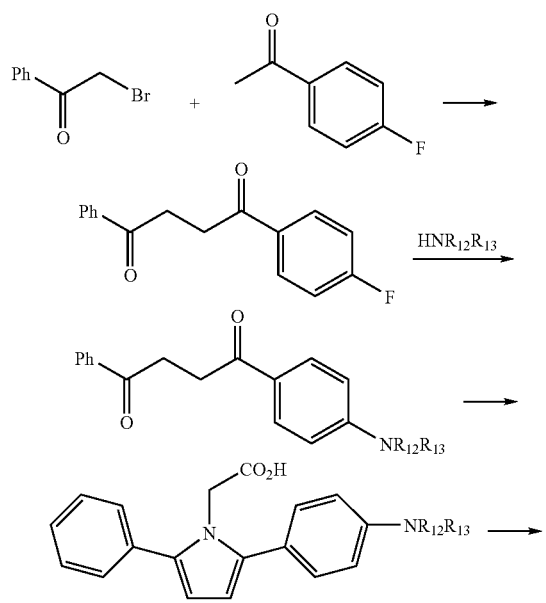

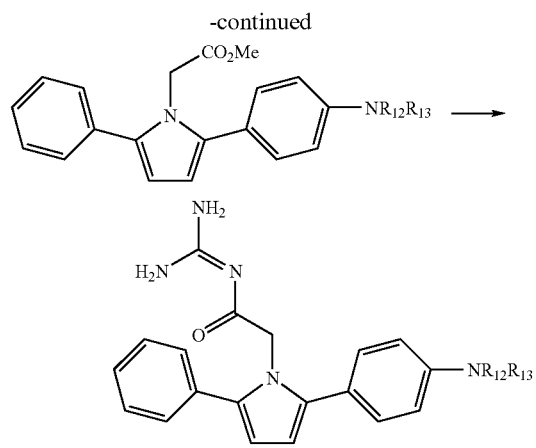

Using essentially the same procedurse described in Example 186 and employing the appropriate amine is step 2, the compounds shown in Table V were prepared and identified by HPLC and mass spectral analyses. HPLC Conditions: HP 1100 HPLC system; Waters Xterra MS C18, 2 mm (i.d.)× 50 mm (length), 3.5 um column, set at 50° C.; Flow rate 1.0 mL/min; Solvent A: 0.02% formic acid in water; Solvent B 0.02% formic acid in ACN; Gradient: Time O: 10% B; 2.5 min 90% B; 3 min 90% B; Sample concentration: ~2.0 mM; Injection volume: 5 uL; Detection: 220 nm, 254 nm DAD.

TABLE V

| Ex. No. | $NR_{12}R_{13}$ | Observed Ion | HPLC Ret. Time (min) |
|---|---|---|---|
| 187 | 4-benzylpiperidine | 402 [+ mode] | 2.44 |
| 188 | morpholine | 404 [M + H] | 2.2 |

EXAMPLE 189

Preparation of (N-{3-[1-(2-{[amino(imino)methyl]amino}-2-oxoethyl)-5-phenyl-1H-pyrrol-2-yl]phenyl}-5-methylisoxazole-3-carboxamide)

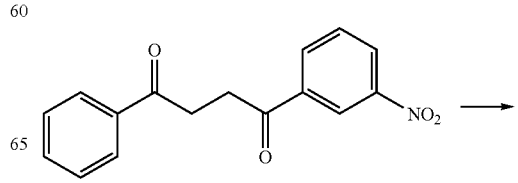

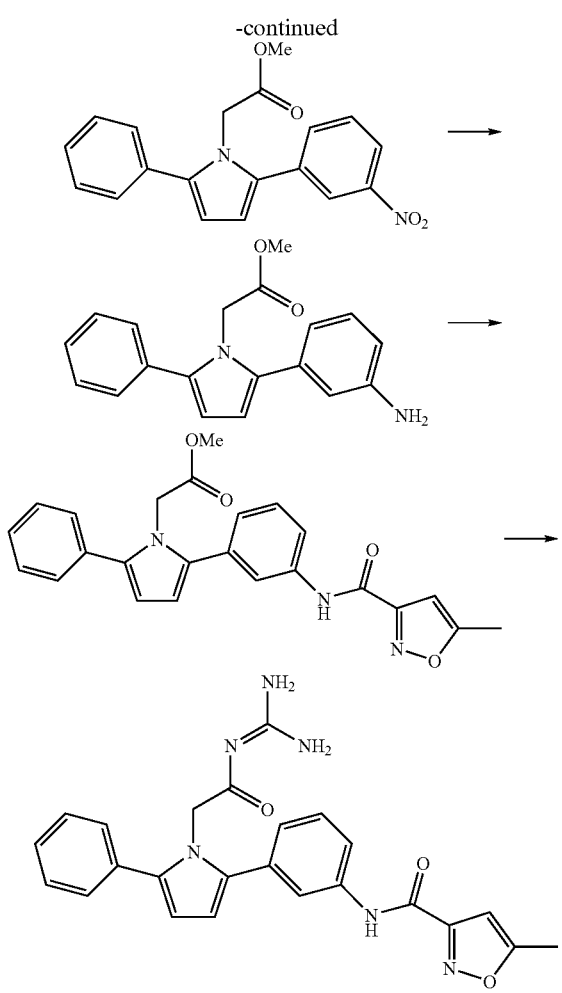

Step 1: [2-(3-Nitro-phenyl)-5-phenyl-pyrrol-1-yl]-acetic acid methyl ester 1-(3-Nitro-phenyl)-4-phenyl-butane-1,4-dione (2.58 g, 9.1 mmoles) is suspended in a solution of glycine (1.37 g, 18.2 mmoles) in 20 ml glacial acetic acid. The suspension is heated to 120° C. for 4.5 h. Subsequently the mixture is cooled to room temperature and the solvent is evaporated under vacuum. The crude product is dissolved in methylene chloride and the solution is extracted twice with 5% sulfuric acid in water. The combined methylene chloride extracts are dried over sodium sulfate and evaporated under reduced pressure to afford the free acid as a brown solid (purity>90%, TLC). The residue is dissolved in a solution of 3 ml trimethylsilyl chloride in 20 ml methanol and the brown solution is agitated for 2 h at 70° C. Subsequently the solvent is removed under vacuum and the product is recrystallized from ethylacetate/hexane. The mother liquor which contained more product is further purified by flash chromatography on silica gel 60 using hexane in ethylacetate 5→20% for elution. Product containing fractions are combined, the solvent is evaporated under reduced pressure and the product is recrystallized as described above. In total 1.8 g of product are obtained. TLC: methylene chloride/methanol 9:1, $R_f$=0.35; $^1$H-NMR (CDCl$_3$, 300 MHz) 3.7 (s, 3H, CH$_3$), 4.6 (s, 2H, CH$_2$), 6.4 (d, 1H, CH), 6.5 (d, 1H, CH), 7.45 (m, 5H, C$_6$H$_5$), 7.6-8.3 (m, 4H, C$_6$H$_4$NO$_2$); MS (ES+) 337 (M+1).

Step 2: [2-(3-Amino-phenyl)-5-phenyl-pyrrol-1-yl]-acetic acid methyl ester

[2-(3-Nitro-phenyl)-5-phenyl-pyrrol-1-yl]-acetic acid methyl ester (2.74 g, 8.1 mmoles) is dissolved in a 1:1 mixture of methanol and tetrahydrofuran (160 mL). Palladium on activated charcoal (10%, 800 mg) is added to the solution under nitrogen. The reaction flask is pressurized in a Parr-shaker with 1-2 bar hydrogen. After 1 h agitation at room temperature, excess hydrogen is replaced with nitrogen and the palladium catalyst is filtered off. The solvent is removed under reduced pressure and [2-(4-amino-phenyl)-5-phenyl-pyrrol-1-yl]-acetic acid methyl ester (2.32 g, 7.6 mmoles) is isolated as a clear oil (94% yield). TLC: etylacetate/hexane 1:1, $R_f$=0.67; MS: (ES+) 307 (M+1).

Step 3: (2-{3-[(5-Methyl-isoxazole-3-carbonyl)-amino]-phenyl}-5-phenyl-pyrrol-1-yl)-acetic acid methyl ester To a solution of [2-(3-amino-phenyl)-5-phenyl-pyrrol-1-yl]-acetic acid methyl ester (0.1 mmol) in DCM (2 mL) is added 5-methyl-isoxazole-3-carbonyl chloride (0.1 mmol) and triethylamine (0.02 mmol). The reactions are agitated at room temperature over night. The solvent is removed under vacuum and the residues are subsequently dried under high vacuum at 50° C. for 2 h.

Step 4: 5-Methyl-isoxazole-3-carboxylic acid {3-[1-(2-guanidino-2-oxo-ethyl)-5-phenyl-1H-pyrrol-2-yl]-phenyl}-amide A solution of free guanidine is prepared by dissolving 500 μmoles Guanidine hydrochloride in sodium methoxide solution (1 ml 0.5 M) and rotated to dryness. The oily residue containing a white precipitate (sodium chloride) is further dried under high vacuum at 50° C. for 2 h. The residue is subsequently dissolved in 300 μl dry dimethylsulfoxide. A white sodium chloride precipitate remained and the supernatant (free guanidine base in solution) is used for guanidinolysis.

The residue from step 3 is dissolved in 300 μl guanidine in dimethylsulfoxide (500 μmoles) and agitated in a shaker at room temperature for 1-4 h. The reaction is quenched with excess acetic acid (ca. 1 mmole), DMSO (200 uL) and water (100 uL), and concentrated in vacuo. The residue is dissolved in a mixture of DMSO, MeOH and water (1.5 mL total) and purified by Gilson preparative HPLC system, Retention Time, 0.76 min., M+H 443.

EXAMPLES 190-211

Preparation of 5-Phenyl-2-(3-amidophenyl)pyrrole Acylguanidine Derivatives

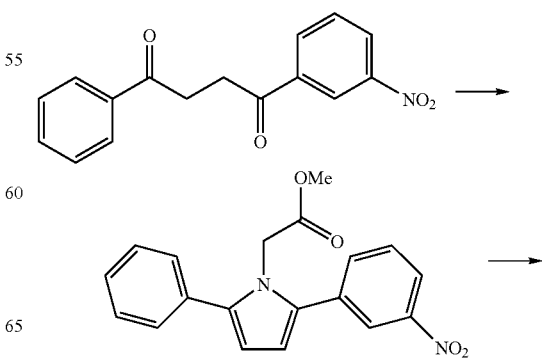

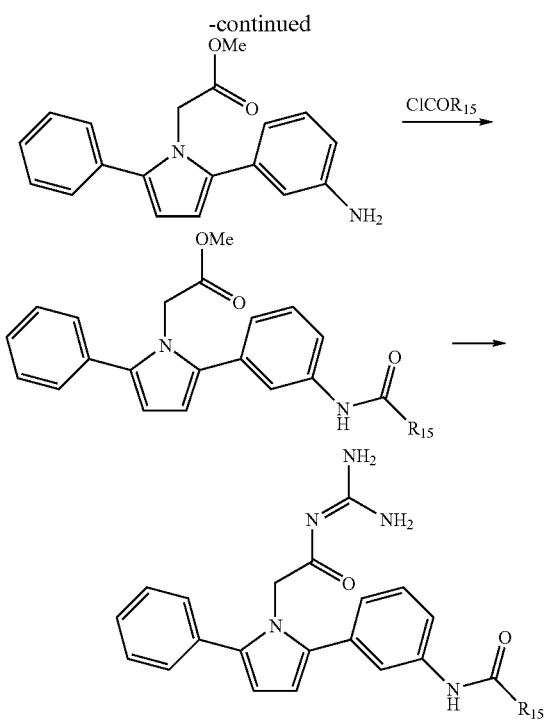

Using essentially the same procedure described in Example 189 and employing the appropriate acid chloride in step 3, the compounds shown in Table VI, were prepared and identified by HPLC and mass spectral analyses. HPLC Conditions: ZMD (Waters) or Platform (Micromass) or LCZ (Micromass) HPLC system: Zorbax SB-C8; Flow rate 3.0 mL/min; Solvent A: 0.1% TFA in water; Solvent B 0.1% TFA in ACN; Gradient: Time 0: 15% B; 2.5 min 95% B; Detection: ELSD detection (SEDEX 55); UV 253 detection (Schimadzu)

The following abbreviations are used in Table VI: Ph is phenyl; Me is methyl; Et is ethyl and Bn is benzyl.

TABLE VI

| Ex. No. | R15 | Observed Ion | HPLC (min) |
|---|---|---|---|
| 189 | 5-methyl-isoxazol-3-yl | 443 | 0.76 |
| 190 | Me | 376 | 0.63 |
| 191 | Et | 390.1 | 0.68 |
| 192 | 2,4-diCl-Ph | 505.9 | 0.89 |
| 193 | i-Bu | 418.1 | 0.77 |
| 194 | 4-Br-Ph | 517.8 | 0.89 |
| 195 | isopropene | 402 | 0.72 |
| 196 | 3-MeO-Ph | 468 | 0.81 |
| 197 | 3-Me-Ph | 452 | 0.84 |
| 198 | cyclohexyl | 444.1 | 0.84 |

TABLE VI-continued

| Ex. No. | R15 | Observed Ion | HPLC (min) |
|---|---|---|---|
| 199 | t-Bu | 418.1 | 0.78 |
| 200 | cyclopropyl | 402 | 0.71 |
| 201 | 2,6-diCl-Ph | 505.9 | 0.82 |
| 202 | 2-thiophenyl methyl | 458 | 0.79 |
| 203 | PhO—CH$_2$ | 468.1 | 0.84 |
| 204 | 1-propene | 402.1 | 0.72 |
| 205 | 2,4-di-MeO-Ph | 498.1 | 0.88 |
| 206 | 3-Br-Ph | 516 | 0.89 |
| 207 | 2-F-5-CF$_3$-Ph | 524.1 | 0.92 |
| 208 | 2,4,5-triF-Ph | 492.1 | 0.85 |
| 209 | 2,4-diCl-5-F-Ph | 524 | 0.91 |
| 210 | 4-F-Bn | 470.1 | 0.83 |
| 211 | 3-F-4-triF-Ph | 524 | 0.96 |

EXAMPLES 212-227

Preparation of 5-Phenyl-2-(3-sulfonamidophenyl)pyrrole Acylguanidine Derivatives

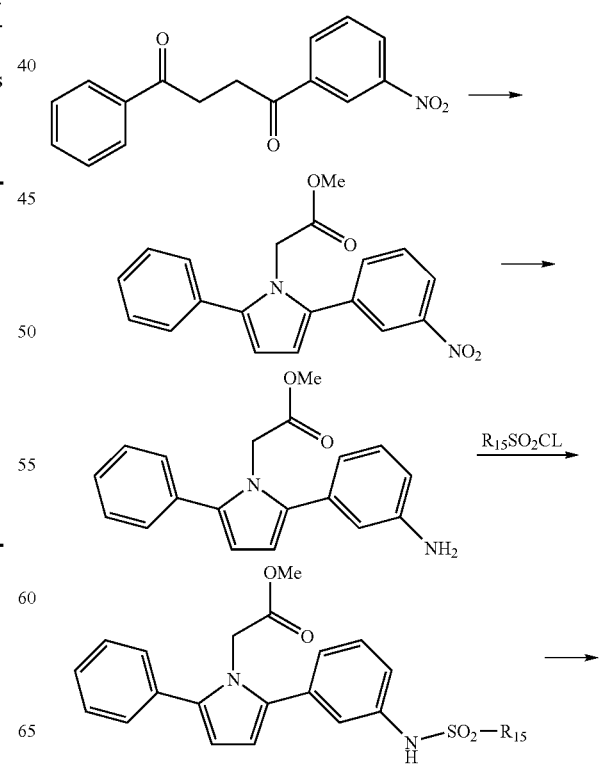

-continued

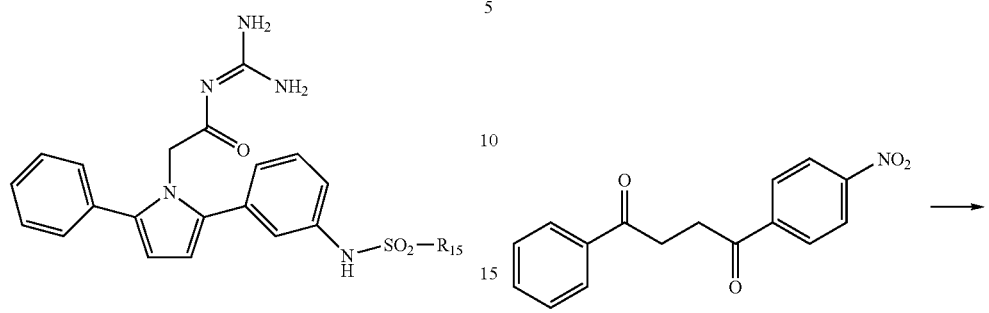

Using essentially the same procedure described in Example 189 and employing the appropriate sulfonyl chloride is step 3, the compounds shown in Table VII were prepared and identified by HPLC and mass spectral analyses.
[3]HPLC Conditions: ZMD (Waters) or Platform (Micromass) or LCZ (Micromass) HPLC system: Zorbax SB-C8; Flow rate 3.0 mL/min; Solvent A: 0.1% TFA in water; Solvent B 0.1% TFA in ACN; Gradient: Time 0: 15% B; 2.5 min 95% B; Detection: ELSD detection (SEDEX 55); UV 253 detection (Schimadzu).

TABLE VII

| Ex. No. | R15 | Observed Ion | HPLC (min) |
|---|---|---|---|
| 212 | 4-Br-Ph | 553.8 | 0.87 |
| 213 | 4-Me-Ph | 488 | 0.81 |
| 214 | Me | 412 | 0.66 |
| 215 | Et | 426 | 0.7 |
| 216 | Bn | 488 | 0.81 |
| 217 | n-Pr | 440 | 0.73 |
| 218 | 2-Phenyl-ethene | 500 | 0.84 |
| 219 | 4-CN-Ph | 499 | 0.79 |
| 220 | 1,1,1-trifluoroethyl | 480 | 0.76 |
| 221 | 4-CF3O-Ph | 558 | 0.91 |
| 222 | 2-Cl-thiophen-2-yl | 514 | 0.84 |
| 223 | 3-Br-Ph | 553.9 | 0.86 |
| 224 | 3-F-6-Me-Ph | 506 | 0.85 |
| 225 | 3-Cl-2-Me-Ph | 522 | 0.89 |
| 226 | 2,5-diMe-Ph | 502.1 | 0.87 |
| 227 | 3-MeO-Ph | 504.1 | 0.81 |

EXAMPLES 228-248

Preparation of 5-Phenyl-2-(4-amidophenyl)pyrrole Acylguanidine Derivatives

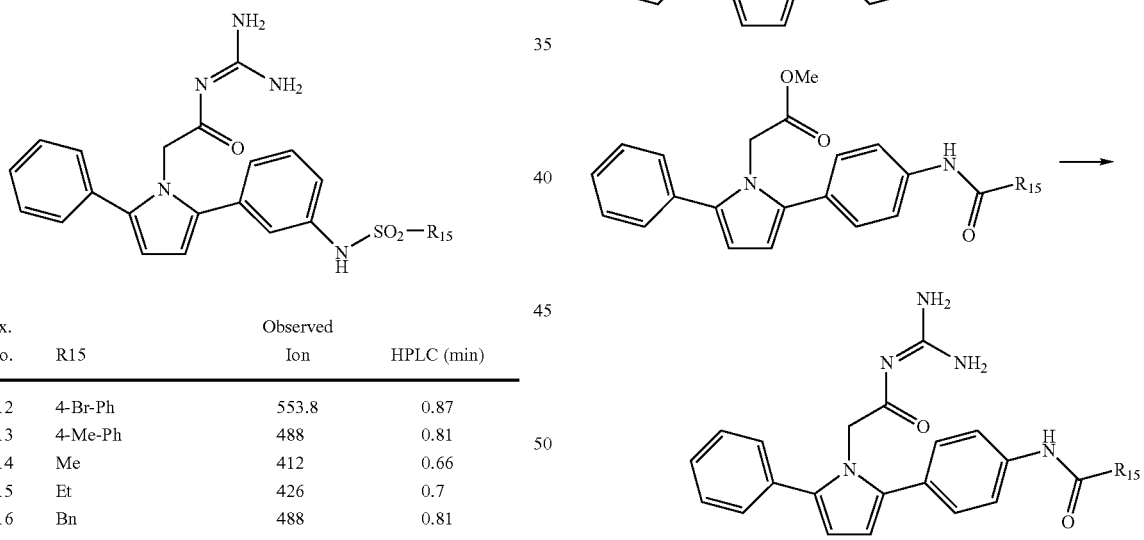

Using essentially the same procedure described in Example 189 and employing 1-(4-nitrophenyl)4-phenylbutane-1,4-dione in Step 1 and the appropriate acid chloride in step 3, the compounds shown in Table VIII were prepared and identified by HPLC and mass spectral analyses. HPLC Conditions: ZMD (Waters) or Platform (Micromass) or LCZ (Micromass) HPLC system: Zorbax SB-C8; Flow rate 3.0 mL/min; Solvent A: 0.1% TFA in water; Solvent B 0.1% TFA in ACN; Gradient: Time 0: 15% B; 2.5 min 95% B; Detection: ELSD detection (SEDEX 55); UV 253 detection (Schimadzu).

TABLE VIII

| Ex. No. | R15 | Observed Ion | HPLC (min) |
|---|---|---|---|
| 228 | 5-methyl-isoxazol-3-yl | 443.1 | 0.77 |
| 229 | Me | 376.1 | 0.63 |
| 230 | Et | 390.1 | 0.67 |
| 231 | 2,4-diCl-Ph | 506 | 0.9 |
| 232 | I-Bu | 418.2 | 0.77 |
| 233 | 4-Br-Ph | 516 | 0.88 |
| 234 | isopropene | 402.1 | 0.72 |
| 235 | 3-MeO-Ph | 468.1 | 0.82 |
| 236 | 3-Me-Ph | 452.1 | 0.84 |
| 237 | cyclohexyl | 444.1 | 0.84 |
| 238 | t-Bu | 418.2 | 0.77 |
| 239 | cyclopropyl | 402.1 | 0.7 |
| 240 | 2,6-diCl-Ph | 506 | 0.85 |
| 241 | 2-thiophenyl methyl | 458.1 | 0.8 |
| 242 | PhO—CH2 | 468.1 | 0.84 |
| 243 | 2,4-diMeO-Ph | 498.1 | 0.86 |
| 244 | 3-Br-Ph | 516 [M − H] | 2.17[1] |
| 245 | 2,4,5-triF-Ph | 492.1 | 0.85 |
| 246 | 2,4-diCl-5-F-Ph | 524 | 0.92 |
| 247 | 4-F-Bn | 470.1 | 0.82 |
| 248 | 3-F-4-triF-Ph | 524 | 0.95 |

[1] HPLC Conditions: HP 1100 HPLC system; Waters Xterra MS C18, 2 mm (i.d.) × 50 mm (length), 3.5 um column, set at 50° C; Flow rate 1.0 mL/min; Solvent A: 0.02% formic acid in water; Solvent B 0.02% formic acid in ACN; Gradient: Time 0:10% B; 2.5 mm 90% B; 3 min 90% B; Sample concentration: ~2.0 mM; Injection volume: 5 uL; Detection: 220 nm, 254 nm DAD.

EXAMPLES 249-264

Preparation of 5-Phenyl-2-(4-sulfonamidophenyl)pyrrole Acylguanidine Derivatives

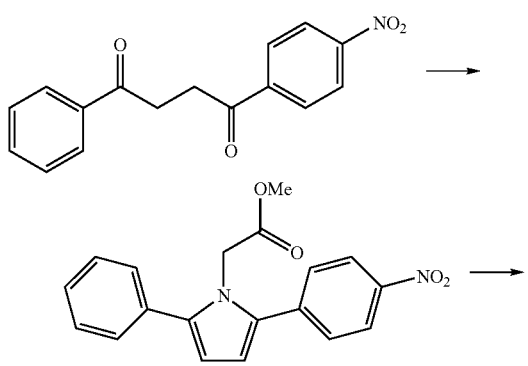

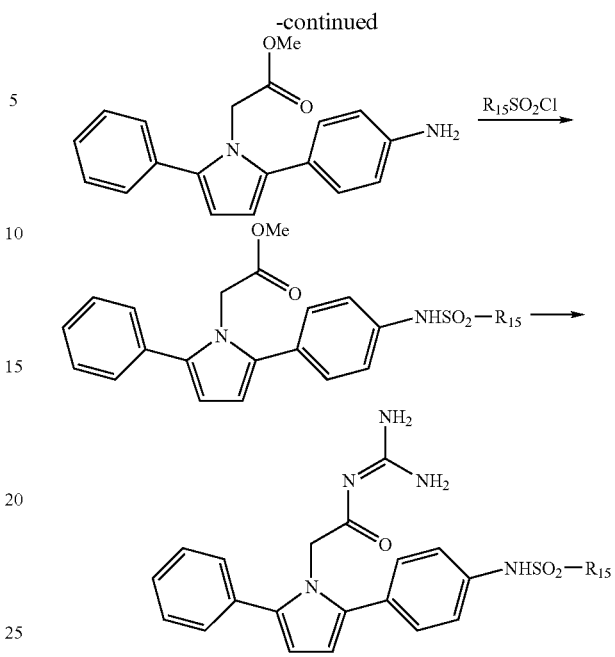

Using essentially the same procedure described in Example 189 and employing 1-(4-nitrophenyl)-4-phenylbutane-1,4-dione in Step 1 and the appropriate sulfonyl chloride in step 3, the compounds shown in Table IX were prepared and identified by HPLC and mass spectral analyses. HPLC Conditions: ZMD (Waters) or Platform (Micromass) or LCZ (Micromass) HPLC system: Zorbax SB-C8; Flow rate 3.0 mL/min; Solvent A: 0.1% TFA in water; Solvent B 0.1% TFA in ACN; Gradient: Time 0: 15% B; 2.5 min 95% B; Detection: ELSD detection (SEDEX 55); UV 253 detection (Schimadzu).

TABLE IX

| Ex. No. | R15 | Observed Ion | HPLC(min) |
|---|---|---|---|
| 249 | 4-Br-Ph | 552 | 0.88 |
| 250 | 4-Me-Ph | 488.1 | 0.82 |
| 251 | Me | 412.1 | 0.66 |
| 252 | Et | 426.1 | 0.69 |
| 253 | Bn | 488.1 | 0.82 |
| 254 | n-Pr | 440.1 | 0.74 |
| 255 | 2-Phenyl-ethene | 500.1 | 0.87 |
| 256 | 4-CF3O-Ph | 558 | 0.93 |
| 257 | 3-Me-Ph | 488.1 | 0.83 |
| 258 | 5-Cl-thien-2-yl | 514 | 0.87 |
| 259 | 3-Br-Ph | 552 | 0.88 |
| 260 | 5-F-2-Me-Ph | 506 | 0.85 |
| 261 | 3-Cl-2-Me-Ph | 522 | 0.91 |
| 262 | 3-CN-Ph | 499 | 0.79 |
| 263 | 2,5-diMe-Ph | 502.1 | 0.87 |
| 264 | 3-MeO-Ph | 504 | 0.81 |

EXAMPLE 265

Preparation of (N-[amino(imino)methyl]-2-{2-phenyl-5-[4-(2-phenylethoxy)phenyl]-1H-pyrrol-1-yl}acetamide)

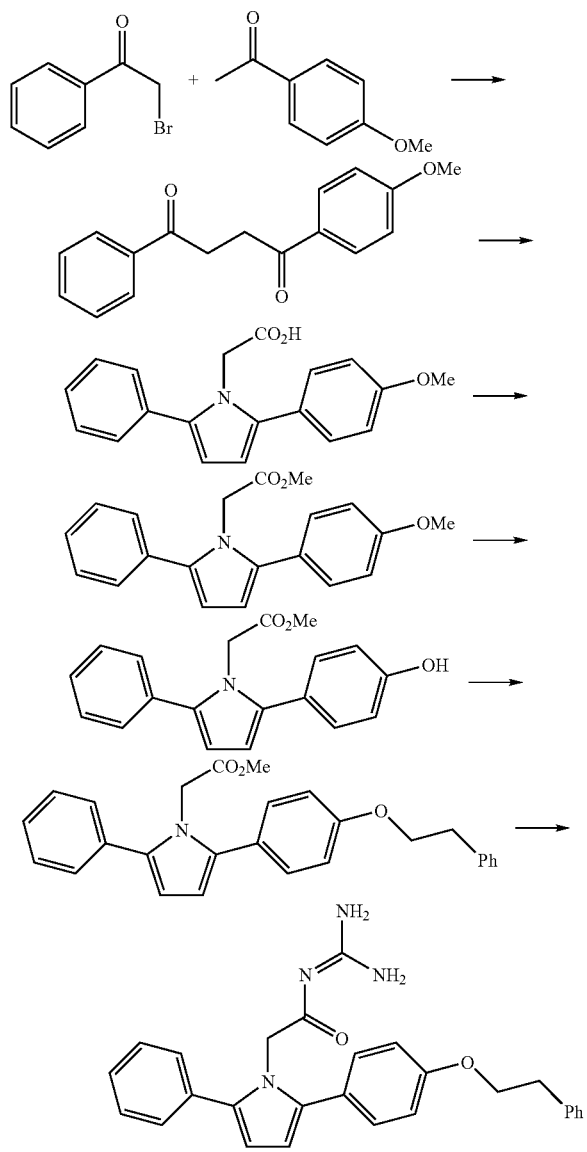

Step 1: 1-(4-Methoxy-phenyl)-4-phenyl-butane-1,4-dione

To a vigorously stirred mixture of zinc chloride (5 g, 36.6 mmol) in anhydrous toluene (200 mL) is added a mixture of diethylamine (2.82 mL, 27.5 mmol) and t-BuOH (2.61 mL, 27.5 mmol) under Argon. After 1 h, 4'-methoxyacetophenone (4.12 g, 27.45 mmol) and 2-bromoacetophenone 1 (3.64 g, 18.3 mmol) are added sequentially. The mixture is stirred for 3 days at room temperature. The mixture is washed with 5% $H_2SO_4$ (200 mL) and the organics separated. The aqueous layer is washed with ethyl acetate (2×100 mL). The organics are combined, dried over sodium sulfate, filtered and concentrated in vacuo. Silica gel column chromatography (hexane/ethyl acetate (5→15%)) afforded 1-(4-Methoxy-phenyl)-4-phenyl-butane-1,4-dione (1.8 g), characterized by LCMS (Obs: 269.09, Cal: 268.11) and $^1$H NMR.

Step 2: [2-(4-Methoxy-phenyl)-5-phenyl-pyrrol-1-yl]-acetic acid

A mixture of 1-(4-methoxy-phenyl)-4-phenyl-butane-1,4-dione (2.90 g, 10.8 mmol) and glycine 4 (1.62 g, 21.6 mmol) in 100 mL of glacial acetic acid is heated at 100° C. The reaction is monitored by TLC, when the starting material is consumed, the mixture is washed with 5% $H_2SO_4$ (200 mL) and then extracted with ethyl acetate (2×200 mL). The organics are combined, dried over sodium sulfate, filtered and concentrated to yield [2-(4-Methoxy-phenyl)-5-phenyl-pyrrol-1-yl]-acetic acid as a green solid (3.40 g, crude), characterized by LCMS (Obs: 308.54, Cal: 307.34).

Step 3: (2,5-Diphenyl-pyrrol-1-yl)-acetic acid methyl ester

To [2-(4-methoxy-phenyl)-5-phenyl-pyrrol-1-yl]-acetic acid (3.4 g, 11.0 mmol) dissolved in anhydrous MeOH (200 mL) and cooled to 0° C. is added chlorotrimethylsilane (1.40 mL, 11.0 mmol). The mixture is refluxed for ~12 h. The contents are concentrated in vacuo. The crude product is purified by flash chromatography on silica gel (10% hexanes/ethyl acetate) to give-(2,5-Diphenyl-pyrrol-1-yl)-acetic acid methyl ester as a yellow solid (2.68 g), characterized by LCMS (Obs: 322.56, Cal: 321.14) and $^1$H NMR.

Step 4: [2-(4-Hydroxy-phenyl)-5-phenyl-pyrrol-1-yl]-acetic acid methyl ester

To a stirred solution of (2,5-diphenyl-pyrrol-1-yl)-acetic acid methyl ester (2.68 g, 8.36 mmol) in anhydrous $CH_2Cl_2$ (250 mL) cooled to −78° C. under argon is added dropwise $BBr_3$ (41.8 mL, 41.8 mmol, 1M). The mixture is warmed to room temperature and monitored by TLC until the reaction is complete (~5 h). The mixture is cooled to −78° C. and slowly quenched with anhydrous MeOH. The mixture is concentrated in vacuo to give [2-(4-Hydroxy-phenyl)-5-phenyl-pyrrol-1-yl]-acetic acid methyl ester a red oil which is purified by flash chromatography on silica gel (5→20% hexanes/ethyl acetate) to give [2-(4-Hydroxy-phenyl)-5-phenyl-pyrrol-1-yl]-acetic acid methyl ester (1.25 g, 48.8% yield) as light brown oil, characterized by LCMS (Obs: 308.25, Cal: 307.34) and $^1$H NMR.

Step 5: [2-(4-Phenethyloxy-phenyl)-5-phenyl-pyrrol-1-yl]-acetic acid methyl ester A solution [2-(4-Hydroxy-phenyl)-5-phenyl-pyrrol-1-yl]-acetic acid methyl ester (0.1 mmol) in DMF (1 mL) is added phenethyl bromide (0.2 mmol) followed by $K_2CO_3$ (80 mg, 578 μmol). The mixture is heated without agitation overnight at 60° C. and monitored by TLC. The mixtures are cooled, water (2 mL) and $CH_2Cl_2$ (2 mL) are added, vortexed, centrifuged and the organics separated. The process is repeated with solely $CH_2Cl_2$ (1 mL). The organics are combined and concentrated in vacuo.

N-{2-[2-(4-Phenethyloxy-phenyl)-5-phenyl-pyrrol-1-yl]-acetyl}-guanidine

To the residue from step 4 is added a solution of guanidine (500 μL, 1M in DMSO) and allowed the mixture allowed to agitate for 8 h. The reaction is quenched by the addition of glacial AcOH (50 μL) and distilled water (100 μL), and the mixture concentrated in vacuo. The residue is dissolved in a mixture of DMSO, MeOH and water (1.5 mL total) and purified by Gilson preparative HPLC system, Retention Time 0.95 min., M+H 439.2.

EXAMPLES 266-284

Preparation of 5-Phenyl-2-(4-alkoxyphenyl)pyrrole Acylguanidine Derivatives

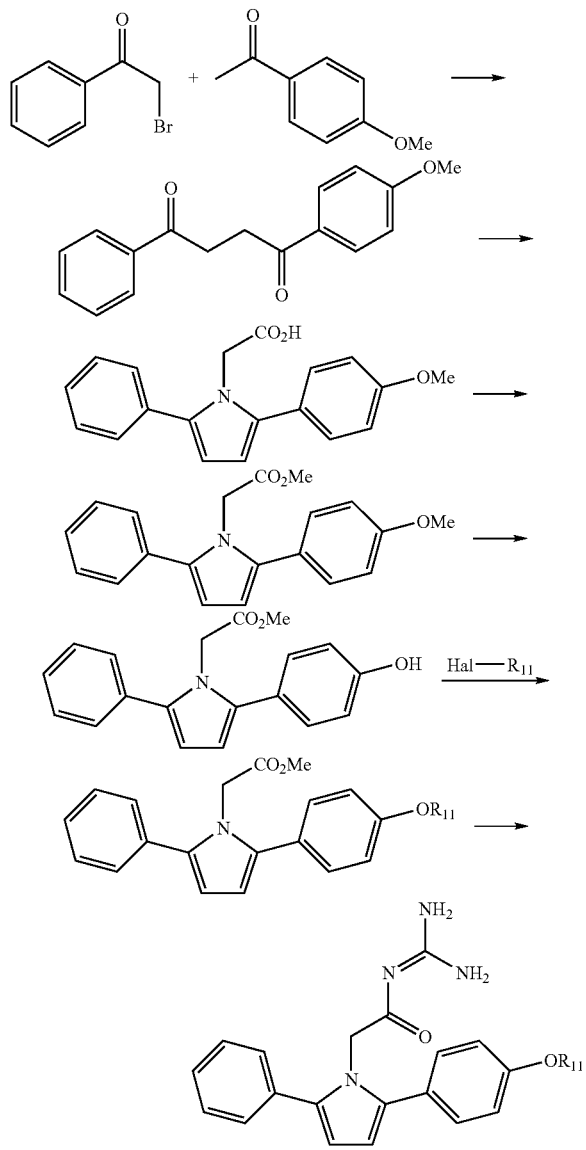

Using essentially the same procedure described in Example 265 and employing the appropriate alkyl halide (Hal-R) in step 5, the compounds shown in Table X were prepared and identified by HPLC and mass spectral analyses. HPLC Conditions: ZMD (Waters) or Platform (Micromass) or LCZ (Micromass) HPLC system: Zorbax SB-C8; Flow rate 3.0 mL/min; Solvent A: 0.1% TFA in water; Solvent B 0.1% TFA in ACN; Gradient: Time 0: 15% B; 2.5 min 95% B; Detection: ELSD detection (SEDEX 55); UV 253 detection (Schimadzu).

TABLE X

| Ex. No. | R11 | Observed Ion | HPLC (Min) |
|---|---|---|---|
| 265 | $CH_2CONHC(NH)NH_2$ | 434.2 | 0.43 |
| 266 | | | |
| 267 | Allyl | 375.2 | 0.77 |
| 268 | $(CH_2)_2OH$ | 379.2 | 0.61 |
| 269 | $(CH_2)_2Oet$ | 407.2 | 0.74 |
| 270 | $CH_2CONH_2$ | 392.2 | 0.55 |
| 271 | 2-isobutene | 389.3 | 0.81 |
| 272 | Cyclohexylmethyl | 431.3 | 1.02 |
| 273 | 3-butene | 389.3 | 0.84 |
| 274 | 4-CN-Bn | 450.2 | 0.85 |
| 275 | 3-Br-Bn | 503.1 | 0.95 |
| 276 | 3-F-Bn | 443.2 | 0.9 |
| 277 | Et | 363.2 | 0.75 |
| 278 | 3-CN-Bn | 450.2 | 0.84 |
| 279 | 2-ethyl-butyl | 419.3 | 1 |
| 280 | n-butyl | 391.3 | 0.88 |
| 281 | 2-propargyl | 373.2 | 0.75 |
| 282 | 3-cyanopropyl | 402.3 | 0.73 |
| 283 | S-2-methyl-butyl | 405.3 | 0.95 |
| 284 | 4-methyl-pentyl | 419.3 | 0.97 |

EXAMPLES 285-303

Preparation of 5-Phenyl-2-(3-alkoxyphenyl)pyrrole Acyguanidine Derivatives

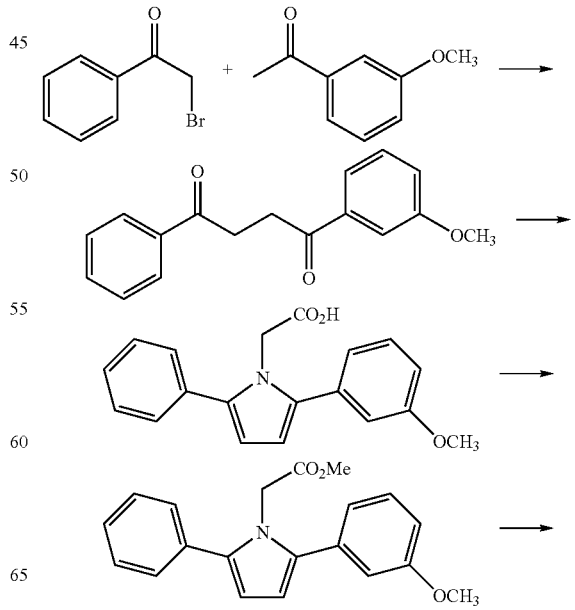

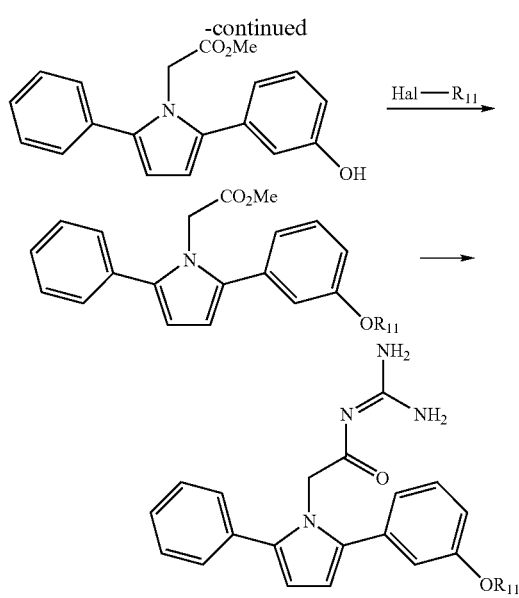

Using essentially the same procedure described in Example 265 and employing 3'-methoxyacetophenone in step 1 and the appropriate alkyl halide in step 5, the compounds shown in Table XI were prepared and identified by [3]HPLC and mass spectral analyses. HPLC Conditions: ZMD (Waters) or Platform (Micromass) or LCZ (Micromass) HPLC system: Zorbax SB-C8; Flow rate 3.0 mL/min; Solvent A: 0.1% TFA in water; Solvent B 0.1% TFA in ACN; Gradient: Time 0: 15% B; 2.5 min 95% B; Detection: ELSD detection (SEDEX 55); UV 253 detection (Schimadzu)

TABLE XI

| Ex. No. | R11 | Observed Ion | HPLC (Min) |
|---|---|---|---|
| 285 | $CH_2CONHC(NH)NH_2$ | 434.2 | 0.42 |
| 286 | phenethyl | 439.2 | 0.94 |
| 287 | allyl | 375.2 | 0.8 |
| 288 | $(CH_2)_2OH$ | 379.2 | 0.62 |
| 289 | $(CH_2)_2OEt$ | 407.2 | 0.74 |
| 290 | $CH_2CONH_2$ | 392.2 | 0.58 |
| 291 | 2-isobutene | 389.3 | 0.86 |
| 292 | cyclohexylmethyl | 430.3 | 1 |
| 293 | 3-butene | 389.3 | 0.83 |
| 294 | 4-CN-Bn | 450.2 | 0.86 |
| 295 | 3-Br-Bn | 503.1 | 0.98 |
| 296 | 3-F-Bn | 443.2 | 0.9 |
| 297 | Et | 363.2 | 0.75 |
| 298 | 3-CN-Bn | 450.2 | 0.86 |
| 299 | 2-ethyl-butyl | 419.3 | 1.03 |
| 300 | n-butyl | 391.3 | 0.88 |
| 301 | 2-propargyl | 373.2 | 0.77 |
| 302 | 3-cyanopropyl | 402.3 | 0.73 |
| 303 | 4-methyl-pentyl | 419.3 | 0.98 |

EXAMPLE 304

Preparation of (N-[2-(2,5-Diphenyl-pyrrol-1-yl)-acetyl]-N'-phenethyl-guanidine)

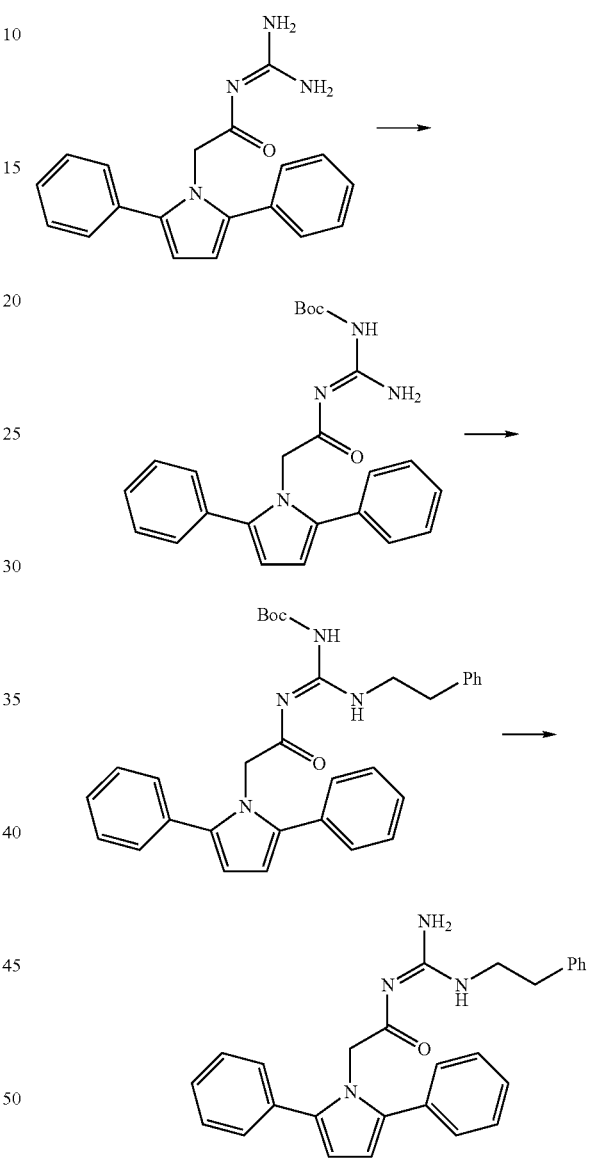

Step 1: Boc protected N-[2-(2,5-Diphenyl-pyrrol-1-yl)-acetyl]-guanidine

To a stirred solution of N-[2-(2,5-diphenyl-pyrrol-1-yl)-acetyl]-guanidine (2.59 g, 8.1 mmol) in $CH_2Cl_2$ (50 mL) is added DIPEA (2.83 mL, 16.2 mmol) and $Boc_2O$ (2.13 g, 9.8 mmol). The mixture is allowed to stir at room temperature and monitored by TLC/HPLC analysis. After 2 days, the reaction is incomplete and additional $Boc_2O$ (4 mmol) is added. The reaction appeared to be complete after an additional 24 h and the mixture is concentrated in vacuo and purified by flash column chromatography. The product is verified by LCMS (Exact Mass: 418.2, Obs: 419.23)

Step 2: Boc protected N-[2-(2,5-Diphenyl-pyrrol-1-yl)-acetyl]-N'-phenethyl-guanidine Boc protected N-[2-(2,5-Diphenyl-pyrrol-1-yl)-acetyl]-guanidine (47 mg, 0.11 mmol) is deprotonated using excess NaH (12 mg, 0.3 mmol, 60% in mineral oil) in anhydrous DMF (10 mL) for 1 h. Phenethyl bromide (200-250 μmol) is added and the mixture heated at 60° C. overnight without agitation. Water (2 mL) and $CH_2Cl_2$ (1.5 mL) are added and the contents vortexed, centrifuged and the organics collected. The extraction is repeated with an additional amount of $CH_2Cl_2$ (1.5 mL) and the organics are combined and concentrated in vacuo.

Step 3: N-[2-(2,5-Diphenyl-pyrrol-1-yl)-acetyl]-N'-phenethyl-guanidine

To the residue from step 2 is added a solution of TFA (500 μL, 1M in $CH_2Cl_2$) and the mixtures are allowed to react overnight at room temperature without agitation. The contents are concentrated in vacuo. The residue is dissolved in a mixture of DMSO, MeOH and water (1.5 mL total) and purified by Gilson preparative [1]HPLC system to give the title compound, RT 2.51 min., M+H 423.

EXAMPLES 305-312

Preparation of 2,5-Diphenyl Acyl guanidine Derivatives

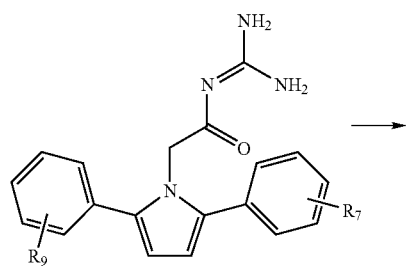

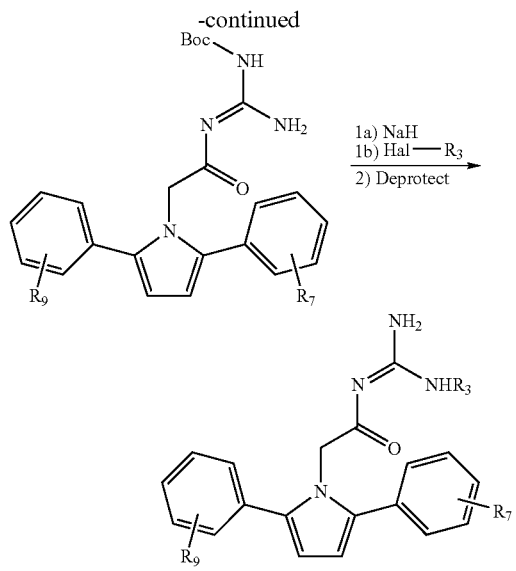

Using essentially the same procedure described in Example 304 and employing the appropriate alkyl halide in step 2, the compounds shown in Table XII were prepared and identified by HPLC and mass spectral analyses. HPLC Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% formic acid in water; Solvent B 0.02% formic acid in ACN; Gradient: Time O: 10% B; 2.5 min 90% B; 3 min 90% B; Sample concentration: ~2.0 mM; Injection volume: 5 uL; Detection: 220 nm, 254 nm DAD.

TABLE XII

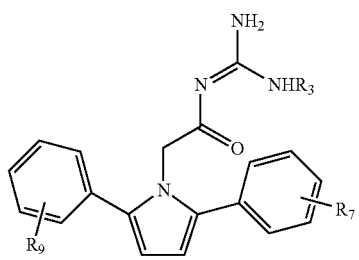

| Ex. No. | R3 | R7 | R9 | Observed Ion | HPLC (Min) |
|---|---|---|---|---|---|
| 305 | 4-t-Bu-Bn | H | H | 465.5[M + H] | 2.72 |
| 306 | —$CH_2$—CH—CH—$CO_2$Me | H | H | [M + H] | 2.23 |
| 307 | 2,3,5-triF-Bn | H | H | [M + H] | 2.52 |
| 308 | 2,3,4-triF-Bn | H | H | [M + H] | 2.56 |
| 309 | $(CH_2)_3$CN | 4-OPh | 2-Cl | 514[M + H] | 2.36 |
| 310 | $(CH_2)_3$OH | 4-OPh | 2-Cl | 505[M + H] | 2.22 |
| 311 | (S)-$CH_2$CH$(CH)_3CO_2$Me | 4-OPh | 2-Cl | 547[M + H] | 2.52 |
| 312 | $(CH_2)_2$OAc | 4-OPh | 2-Cl | 533[M + H] | 2.40 |

EXAMPLE 313

Preparation of (2-{(2-(2-Chlorophenyl)-5-[4-(pent-4-enyloxy)phenyl]-1H-pyrrol-1-yl}-N-[[(3-hydroxypropyl)amino](imino)methyl]acetamide)

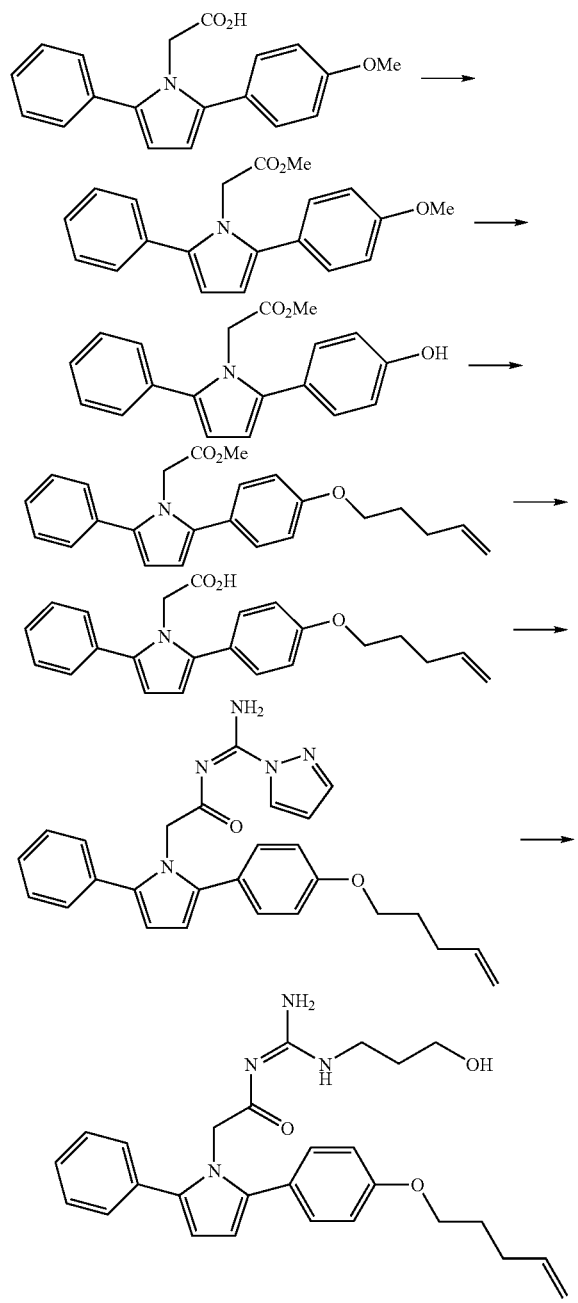

Step 1.

To an ice cooled solution of [2-(4-methoxyphenyl)-5-phenylpyrrol-1-yl]-acetic acid (44.33 g, 130 mmol) in methanol (500 mL) is added chlorotriethylsilane (21.8 mL, 130 mmol) dropwise. The mixture is then refluxed for 3.5 hours. The solvent is removed and the crude product purified by flash chromatography over silica gel with 5-20% ethyl acetate in hexanes to give 40 g (95% yield) identified by HPLC and MS.

Step 2.

To a solution of [2-(4-methoxyphenyl)-5-phenylpyrrol-1-yl]-acetic acid methyl ester (7.1 g, 20 mmol) in DCM at −78° C. is added boron tribromide (100 mL, 1 M solution in DCM, 100 mmol) dropwise. The mixture is stirred while warming to r.t. for 3.5 hours, and recooled to −78° C. and quenched by addition of methanol. The solvent is removed and the crude product purified by flash chromatography over silica gel with 5-20% ethyl acetate in hexanes to give the title product 2.0 g (30% yield) identified by HPLC and MS.

Step 3.

To a solution of [2-(4-hydroxyphenyl)-5-phenylpyrrol-1-yl]-acetic acid methyl ester (68 mg, 0.2 mmol) in DMF (2 mL) is added 5-bromo-1-pentene (89 mg, 0.6 mmol), sodium iodide (5 mg, catalytic amount) and cesium carbonate (195 mg, 0.6 mmol). The mixture is stirred at 60° C. for 16 hours then diluted with DCM (10 mL) and washed with water (2×5 mL) and dried over MgSO$_4$ and concentrated in vacuo to give the title product identified by HPLC and MS.

Step 4.

To a solution of [2-(4-Pent-4-enyloxyphenyl)-5-phenylpyrrol-1-yl]-acetic acid methyl ester (0.2 mmol) in ethanol (2 mL) is added sodium hydroxide (24 mg, 0.6 mmol). The mixture is stirred at 75° C. for 16 hours then concentrated in vacuo to give the title compounds identified by HPLC and MS.

Step 5.

A solution of [2-(4-pent-4-enyloxyphenyl)-5-phenylpyrrol-1-yl]-acetic acid and 1,1'-carbonyldiimidazole (162 mg, 1.0 mmol) in DCM (2 mL) is stirred at r.t. for 1 hour, then 1-H-pyrazole-1-carboxamidine.hydrochloride (146 mg, 1 mmol) triethylamine (0.278 mL, 2 mmol) and dimethylaminopyridine (5 mg, catalytic amount) are added and the mixture stirred at r.t. for 16 hours. The mixture is filtered and the solid washed with DCM. The filtrate is then washed with water, dried over MgSO$_4$ and concentrated to give the title product identified by HPLC and MS.

Step 6.

A solution of N-(Amino-pyrazol-1-yl-methylene)-2-[2-(4-pent-4-enyloxy-phenyl)-5-phenyl-pyrrol-1-yl]-acetamide (0.2 mmol), aminopropanol (45 uL, 0.6 mmol) and diisopropylethylamine (104 μL, 0.2 mmol) in DCM is stirred at r.t. for 16 hours. The solvent is removed in vacuo and the residue is dissolved in a mixture of DMSO, MeOH and water (1.5 mL total) and purified by Gilson preparative $^1$HPLC system.

EXAMPLES 314-317

Preparation of (2-{(2-(2-Chlorophenyl)-5-[4-(alkoxy)phenyl]-1H-pyrrol-1-yl}-N-[[(3-hydroxypropyl)amino](imino)methyl]acetamide) Derivatives

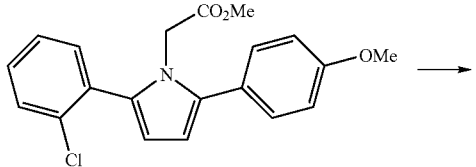

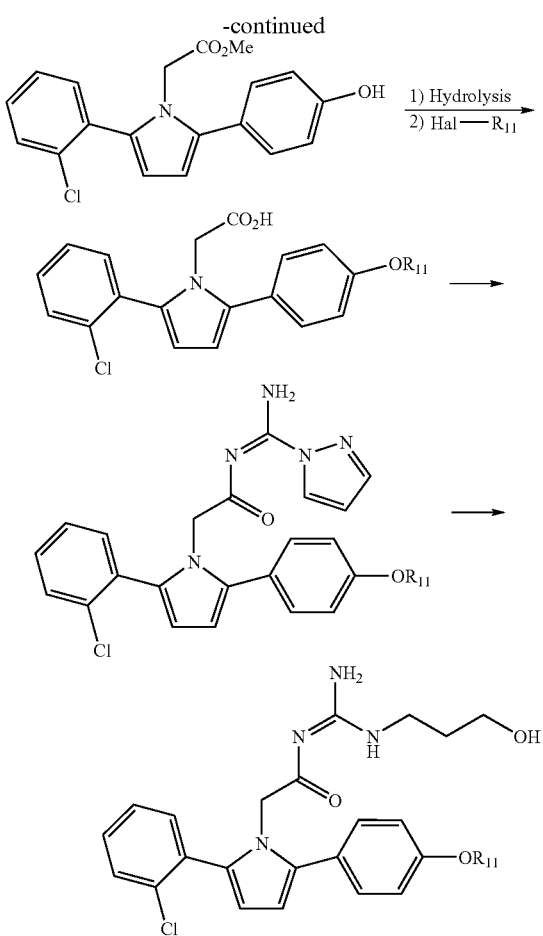

Using essentially the same procedure described in Example 313 and employing the appropriate alkyl halide in step 3, the compounds shown in Table XIII are prepared and identified by [2]HPLC and mass spectral analyses. HPLC Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% formic acid in water; Solvent B 0.02% formic acid in ACN; Gradient: Time o: 10% B; 2.5 min 90% B; 3 min 90% B; Sample concentration: ~2.0 mM; Injection volume: 5 μL; Detection: 220 nm, 254 nm DAD.

TABLE XIII

| Ex. No. | R11 | Observed Ion | HPLC (Min) |
|---|---|---|---|
| 314 | —(CH$_2$)$_4$CN | 508 [M + H] | 2.09 |
| 315 | —(CH$_2$)$_4$CHCH$_2$ | 509 [M + H] | 2.46 |

TABLE XIII-continued

| Ex. No. | R11 | Observed Ion | HPLC (Min) |
|---|---|---|---|
| 316 | (1,3-dioxolan-2-yl propyl) | 527 [M + H] | 2.04 |
| 317 | n-pentyl | 497 [M + H] | 2.44 |

EXAMPLES 318-338

Preparation of 2,5-Diphenylpyrrole Acylguanidine Derivatives

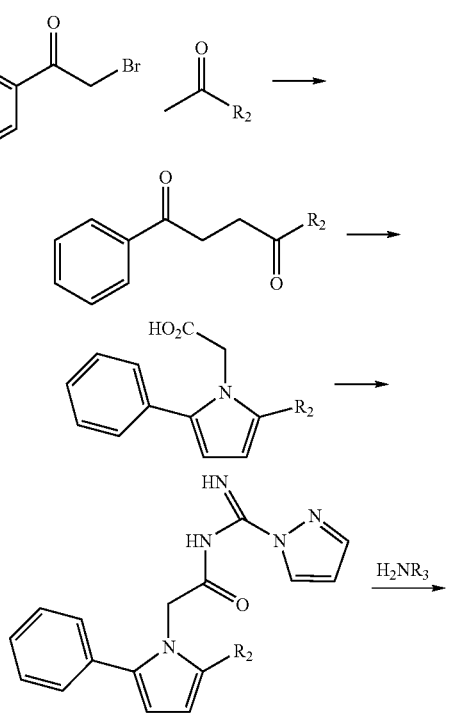

-continued

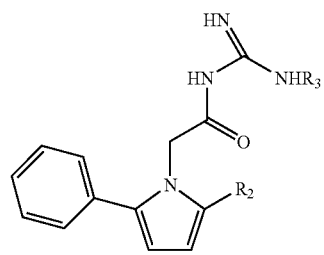

Using essentially the same procedure described in Examples 11 and 313 and employing the appropriate bromoacetophenone and amine, the compounds shown in Table XIV are prepared and identified by HPLC and mass spectral analyses. HPLC Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% formic acid in water; Solvent B 0.02% formic acid in ACN; Gradient: Time O: 10% B; 2.5 min 90% B; 3 min 90% B; Sample concentration: ~2.0 mM; Injection volume: 5 uL; Detection: 220 nm, 254 nm DAD.

TABLE XIV

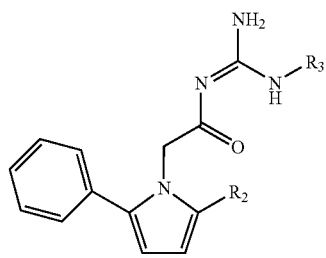

| Ex. No. | R3 | R2 | Observed Ion | HPLC (min) |
|---|---|---|---|---|
| 318 | (CH$_2$)$_3$OH | 4-CN-Ph | 402 [M + H] | 2.34 |
| 319 | (CH$_2$)$_3$OH | 4-i-Pr-Ph | 419 [M + H] | 2.58 |
| 320 | (CH$_2$)$_3$OH | 4-n-Pr-Ph | 419 [M + H] | 2.6 |
| 321 | (CH$_2$)$_3$OH | 4-n-Bu-Ph | 433 [M + H] | 2.7 |
| 322 | (CH$_2$)$_3$OH | 4-i-Bu-Ph | 433 [M + H] | 2.68 |
| 323 | (CH$_2$)$_3$OH | 4-n-pentyl-Ph | 447 [M + H] | 2.8 |
| 324 | (CH$_2$)$_3$OH | 4-n-BuO-Ph | 449 [M + H] | 2.64 |
| 325 | (CH$_2$)$_3$OH | 4-Ph-Ph | 453 [M + H] | 2.62 |
| 326 | (CH$_2$)$_3$OH | 4-Br-Ph | 456 [M + H] | 2.49 |
| 327 | (CH$_2$)$_3$OH | 4-cyclohexyl-Ph | 459 [M + H] | 2.8 |
| 328 | (CH$_2$)$_3$OH | 4-PhO-Ph | 469 [M + H] | 2.63 |
| 329 | (CH$_2$)$_3$OH | 4-(4'-Ac-PhO)-Ph | 511 [M + H] | 2.54 |
| 330 | 2,3,4-trifluorobenzyl | 4-CN-Ph | 488 [M + H] | 2.69 |
| 331 | 2,3,4-trifluorobenzyl | 4-i-Pr-Ph | 505 [M + H] | 2.97 |
| 332 | 2,3,4-trifluorobenzyl | 4-n-Pr-Ph | 505 [M + H] | 2.99 |
| 333 | 2,3,4-trifluorobenzyl | 4-n-Bu-Ph | 519 [M + H] | 3.1 |
| 334 | 2,3,4-trifluorobenzyl | 4-n-BuO-Ph | 535 [M + H] | 3.02 |
| 335 | 2,3,4-trifluorobenzyl | 4-Br-Ph | 542 [M + H] | 2.87 |
| 336 | 2,3,4-trifluorobenzyl | 4-cyclohexyl-Ph | 545 [M + H] | 3.2 |
| 337 | 2,3,4-trifluorobenzyl | 4-PhO-Ph | 555 [M + H] | 2.99 |
| 338 | 2,3,4-trifluorobenzyl | 4-(4'-Ac-PhO)-Ph | 597 [M + H] | 2.88 |

EXAMPLES 339-367

Preparation of 2-(2-Chlorophenyl)-5-(4-alkoxyphenyl)pyrrole Acylguanidine Derivatives

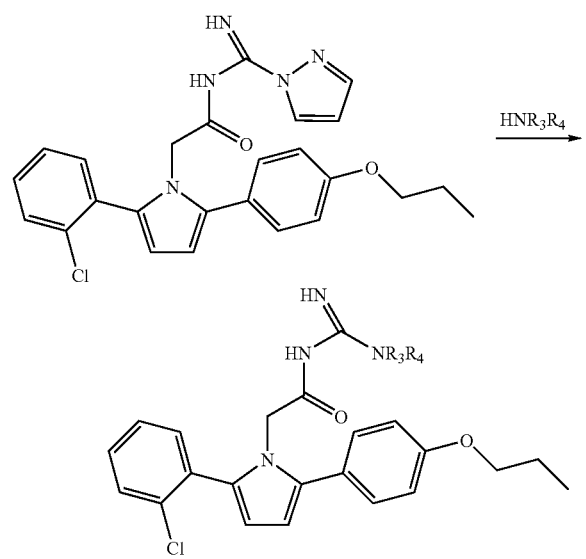

Using essentially the same procedure described in Example 313 and employing the appropriate bromoacetophenone and amine, the compounds shown in Table XV are prepared and identified by HPLC and mass spectral analyses. HPLC Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% formic acid in water; Solvent B 0.02% formic acid in ACN; Gradient: Time 0: 10% B; 2.5 min 90% B; 3 min 90% B; Sample concentration: ~2.0 mM; Injection volume: 5 uL; Detection: 220 nm, 254 nm DAD.

TABLE XV

| Ex. No. | R3R4NH | Observed Ion [M + H] | HPLC (min) |
|---|---|---|---|
| 339 | 4-aminocyclohexanecarboxylic acid | 537 | 2.43 |
| 340 | trans-4-aminocyclohexanol | 509] | 2.35 |
| 341 | 4-aminobutyric acid | 497 | 2.32 |
| 342 | beta-alanine | 483] | 2.31 |
| 343 | H-beta-ALA-NH2 | 482 | 2.12 |
| 344 | 3-amino-1-propanol | 469 | 2.14 |
| 345 | 3-methoxypropylamine | 483 | 2.35 |
| 346 | (+/−) 3-amino-1,2-propanediol | 485 | 2.14 |
| 347 | N-acetylethylenediamine | 496 | 2.19 |
| 348 | 3-amino-2,2-dimethyl-1-propanol | 497 | 2.35 |
| 349 | 3-(methylthio)propylamine | 499 | 2.40 |

TABLE XV-continued

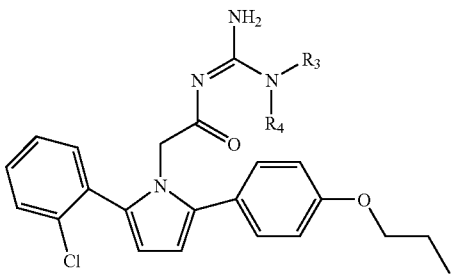

| Ex. No. | R3R4NH | Observed Ion [M + H] | HPLC (min) |
|---|---|---|---|
| 350 | 2-(2-aminomethyl)-1,3-dioxolane | 511 | 2.26 |
| 351 | phenethylamine | 515 | 2.53 |
| 352 | 1-(aminopropyl)imidazole | 519 | 1.72 |
| 353 | 2-thiopheneethylamine | 521 | 2.48 |
| 354 | 3-aminocyclohexanecarboxylic acid | 537 | 2.44 |
| 355 | 2,2,3,3,3-pentafluoropropylamine | 543 | 3.26 |
| 356 | 4-(methylamino)butyronitrile | 492 | 2.76 |
| 357 | 3-(trifluoromethyl)benzylamine | 569 | 2.84 |
| 358 | 2-thiophenemethylamine | 507 | 2.55 |
| 359 | furfurylamine | 491 | 2.43 |
| 360 | 4-(aminomethyl)benzoic acid | 545 | 2.41 |
| 361 | 4-(trifluoromethyl)benzyl amine | 569 | 2.88 |
| 362 | 2,3,4-trifluorobenzylamine | 555 | 2.87 |
| 363 | 3-methoxybenzylamine | 531 | 2.55 |
| 364 | 4-hydroxy-3-methoxybenzylamine | 547 | 2.32 |
| 365 | 3-(trifluoromethoxyy)benzylamine | 585 | 2.88 |
| 366 | methyl 4-(aminomethyl)benzoate | 559 | 2.59 |
| 367 | methyl trans-4-(aminomethyl) cyclohexanecarboxylate | 565 | 2.51 |

EXAMPLE 368

Preparation of (N-[Amino-(3-benzyl-ureido)-methylene]-2-(2,5-diphenyl-pyrrol-1-yl)-acetamide)

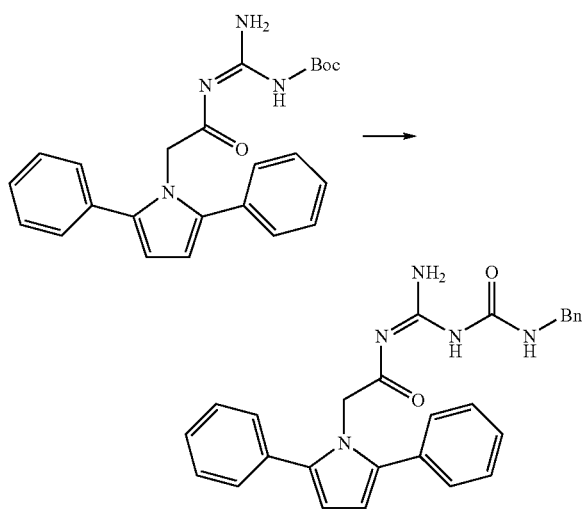

To a solution of Boc protected N-[2-(2,5-diphenyl-pyrrol-1-yl)-acetyl]-guanidine (48 mg, 0.11 mmol) in DMSO (0.5 mL) is added benzylamine (140 μmol). The reaction is heated (110° C.) for 3 h, then concentrated in vacuo. The residue is dissolved in a mixture of DMSO, MeOH and water (1.5 mL total) and purified by Gilson preparative HPLC system, RT 1.28 min., M+H 452.37 HPLC Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% formic acid in water; Solvent B 0.02% formic acid in ACN; Gradient: Time 0: 10% B; 2.5 min 90% B; 3 min 90% B; Sample concentration: ~2.0 mM; Injection volume: 5 μL; Detection: 220 nm, 254 nm DAD.

EXAMPLES 369-388

Preparation of (N-[Amino-(3-ureido)-methylene]-2-(2,5-diphenyl-pyrrol-1-yl)-acetamide) Derivatives

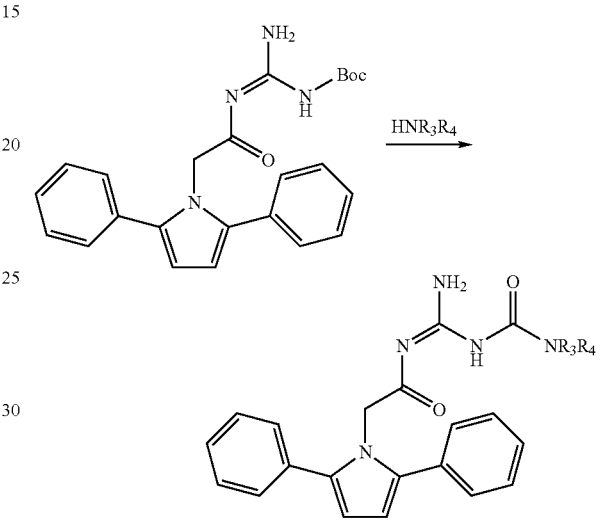

Using essentially the same procedure described in Example 368 and employing the appropriate amine, the compounds shown in Table XVI are prepared and identified by HPLC and mass spectral analyses. HPLC conditions are the same as those used in Example 368.

TABLE XVI

| Ex. No. | NR3R4 | Observed ion | HPLC (Min) |
|---|---|---|---|
| 369 | benzyl-methylamine | 466.34 | 1.41 |
| 370 | diethylamine | 418.37 | 1.26 |
| 371 | 2,5-dihydro-1H-pyrrole | 414.32 | 1.19 |
| 372 | ethylamino ethanol | 434.33 | 1.08 |
| 373 | piperazine | 431.29 | 0.88 |
| 374 | piperidine | 430.34 | 1.3 |
| 375 | morpholine | 432.32 | 1.2 |
| 376 | pyrrolidine | 416.33 | 1.15 |
| 377 | N-(4-fluorophenyl)-piperazine | 525.34 | 1.41 |
| 378 | N-benzyl-piperazine | 521.33 | 1.02 |
| 379 | 4-benzyl-piperidine | 520.39 | 1.52 |
| 380 | 3-hydroxy-pyrrolidine | 432.2 | 0.97 |
| 381 | cyclohexylmethylamine | 458.41 | 1.38 |

TABLE XVI-continued

[Structure: NH2-C(=N)-NH-C(=O)-NR3R4 connected via -C(=O)-CH2-N to 2,5-diphenyl-1H-pyrrole]

| Ex. No. | NR3R4 | Observed ion | HPLC (Min) |
|---|---|---|---|
| 382 | n-butylamine | 418.32 | 1.24 |
| 383 | ethyl-methylamine | 404.35 | 1.2 |
| 384 | 3-hydroxy-piperidine | 446.37 | 1.1 |
| 385 | i-propylamino ethanol | 448.33 | 1.15 |
| 386 | 2-methoxyethyl-methylamine | 434.42 | 1.17 |
| 387 | i-propyl-(2-methoxyethyl)amine | 462.2 | 1.3 |
| 388 | hexylamine | 446.42 | 1.39 |

EXAMPLE 389

Preparation of (N"-{[2-(2-adamantyl)-5-phenyl-1H-pyrrol-1-yl]acetyl}guanidine)

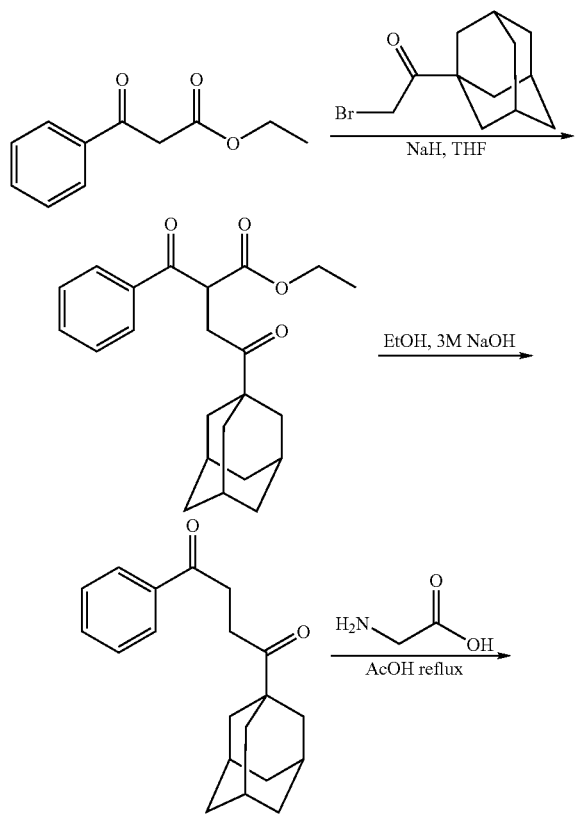

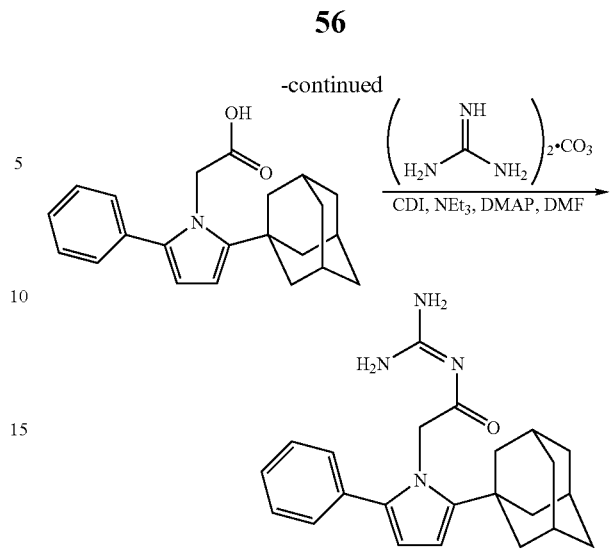

Step 1.

To a slurry of 1.08 g (27.08 mmol, 60%) NaH in 26 mL anhydrous THF under $N_2$ at 0° C. was added 5.00 g (26.01 mmol) ethyl benzoyl acetate. The mixture was stirred at room temperature for 20 minutes. The mixture was cooled to 0° C. in an ice-salt bath and 8.69 g (33.79 mmol) 1-adamantyl bromoethyl ketone was added. Reaction was left to warm to room temperature while stirring overnight. The mixture was cooled to 0° C. and 50-70 mL 10% citric acid was added. The solution was extracted twice with 80 mL ethyl acetate. The combined ethyl acetate extracts were washed with sat. aqueous NaCl, dried over $MgSO_4$, and concentrated to afford a yellow oil: m/z 369 (M+H).

Step 2.

To a solution of 12.04 g 4-adamantan-1-yl-2-benzoyl-4-oxo-butyric acid ethyl ester from Step 1 in 30 mL ethanol was added 30 mL 3M aqueous NaOH. The reaction was heated to 110° C. overnight. The reaction was diluted with ethyl acetate and washed with water. The organic extract was washed with sat. aqueous NaCl, dried over $MgSO_4$, and concentrated to afford a viscous brown oil: m/z 297 (M+H).

Step 3.

A solution of 5.54 g (18.69 mmol) 1-adamantan-1-yl-4-phenyl-butane-1,4-dione from Step 2 and 2.80 g (37.38 mmol) glycine in 62 mL acetic acid was heated to reflux for 5 hours. The reaction was concentrated and the residue was taken up in ethyl acetate and the undissolved solid was filtered off. The filtrate was washed with 5% aqueous $H_2SO_4$. The aqueous layer was extracted two times with ethyl acetate. The combined organic extracts were washed with sat. aqueous NaCl, dried over $MgSO_4$, and concentrated to afford a brown solid which was dried under vacuum overnight: m/z 336 (M+H).

Step 4.

To a solution of 3.00 g (8.94 mmol) 2-adamantan-1-yl-5-phenyl-pyrrol-1-yl)-acetic acid in 89 mL anhydrous DMF under $N_2$ was added 7.25 g (44.71 mmol) N,N'-carbonyldiimidazole. The solution was stirred at room temperature for 1 hr, upon which time 8.05 g (44.71 mmol) guanidine carbonate, 12.46 mL (89.43 mmol) triethylamine, and 0.10 g (0.8 mmol) DMAP were added. The mixture was stirred at room temperature overnight. The reaction mixture was added to water and extracted twice with ethyl acetate. The combined organic extracts were washed 3× with water, 1× with sat.

aqueous NaCl, dried over MgSO₄, and concentrated to give a brown solid which was dried under vacuum overnight: m/z 377 (M+H).

EXAMPLE 390

Preparation of (2-[2-(1-Adamantyl)-5-phenyl-1H-pyrrol-1-yl]-N-[(1Z)-amino(ethylamino-methylene] acetamide)

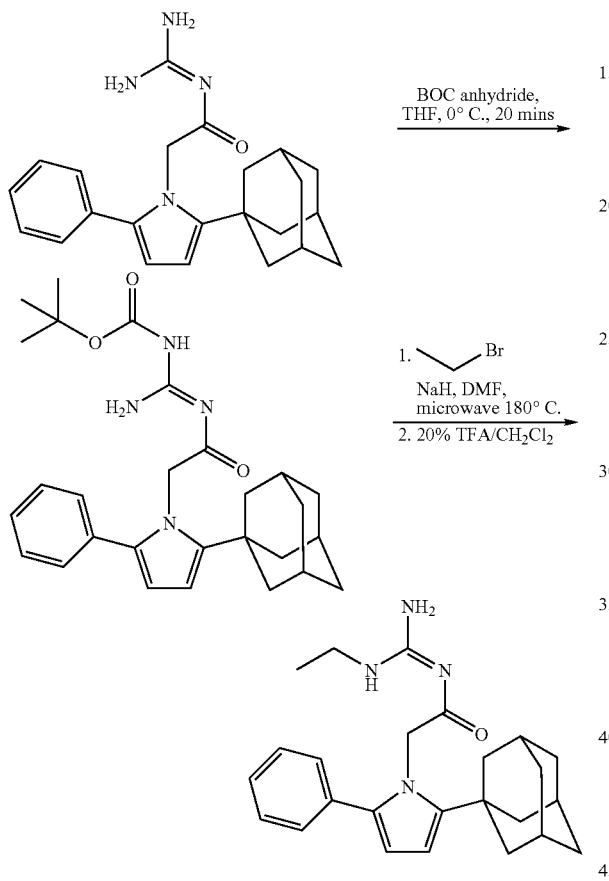

Step 1. To a solution of 1.04 g (2.77 mmol) N-[2-(2-adamantan-1-yl-5-phenyl-pyrrol-1-yl)-acetyl]-guanidine in 27 mL anhydrous THF under N₂ at 0° C. was added 1.25 mL (1.25 mmol) di-tert-butyldicarbonate dropwise. The reaction was stirred at 0° C. for 20 minutes. The reaction mixture was added to water and extracted twice with ethyl acetate. The combined organic extracts were washed with sat. aqueous NaCl, dried over MgSO₄, and concentrated to give a brown oil. The residue was purified by Gilson preparative ⁴HPLC to afford 427 mg of N-[2-(2-adamantan-1-yl-5-phenyl-pyrrol-1-yl)-acetyl]-guanidine carboxylic acid tert-butyl ester [²LC-MS data molecular ion and retention time): m/z 477 (M+H); 3.86 min] as a brown gum.

Step 2. N-[2-(2-adamantan-1-yl-5-phenyl-pyrrol-1-yl)-acetyl]-guanidine carboxylic acid tert-butyl ester was dissolved in 2.0 mL anhydrous DMF and was added to a glass microwave reaction tube containing 1 equivalent (60%) NaH under N₂. Reaction was stirred for 1 hr at room temperature before the addition of 1 equivalent of alkyl bromide. The reaction was subjected to microwave radiation at 180° C. for 540 seconds. The reaction was concentrated and the residue was taken up in CH₂Cl₂ and washed with water. The CH₂Cl₂ layer was diluted with TFA to make a 20% solution. The mixture was stirred for 4 hours at room temperature. The reaction was concentrated and the residue is dissolved in a mixture of DMSO, MeOH and water (1.5 mL total) and purified by Gilson preparative HPLC system, R. T. 2.1, M+H 405.4. HPLC conditions: YMC Pro C18 column, 20 mm×50 mm ID, 5 μM; 2 mL injection; Solvent A: Water (0.05% NH₄OH buffer); Solvent B: acetonitrile (0.05% NH₄OH buffer); Gradient: Time 0: 5% B; 2 min: 5% B; 12 min: 95% b, Hold 95% B 3 min; Flow rate 22.5 mL/min; Detection: 254 nm DAD.

EXAMPLES 391-395

Preparation of (2-[2-(1-Adamantyl)-5-phenyl-1H-pyrrol-1-yl]-N-[(1Z)-amino(ethylamino-methylene] acetamide)

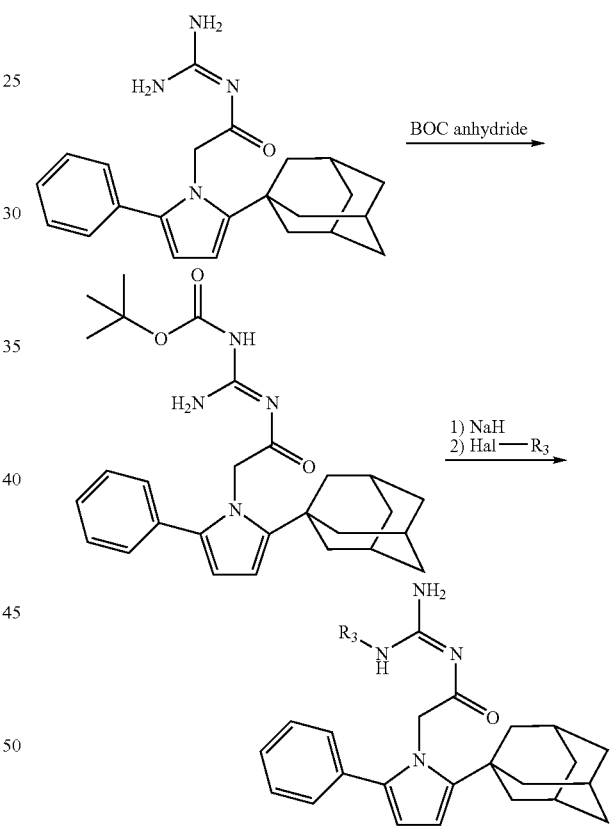

Using essentially the same procedure described in Example 390 and employing the appropriate alkyl or aryl halide, the compounds shown in Table XVII were prepared and identified by HPLC and mass spectral analyses. HPLC Conditions: HP 1100 HPLC system; Waters Xterra MS C₁₈ column, 2 mm (i.d.)×50 mm×2 mm, 3.5μ particle size, set at 50° C.; flow rate 1.0 mL/min; Solvent A: 0.05% NH₄OH in water; Solvent B: 0.05% NH₄OH in ACN; Gradient: Time 0: 10% B; 2.5 min: 90% B; 3 min: 90% B; Sample concentration: ~2.0 mM; Injection volume: 5 μL; Detection: 254 nm DAD, API-ES Scanning Mode Negative 150-700; Fragmentor 70 mV.

TABLE XVII

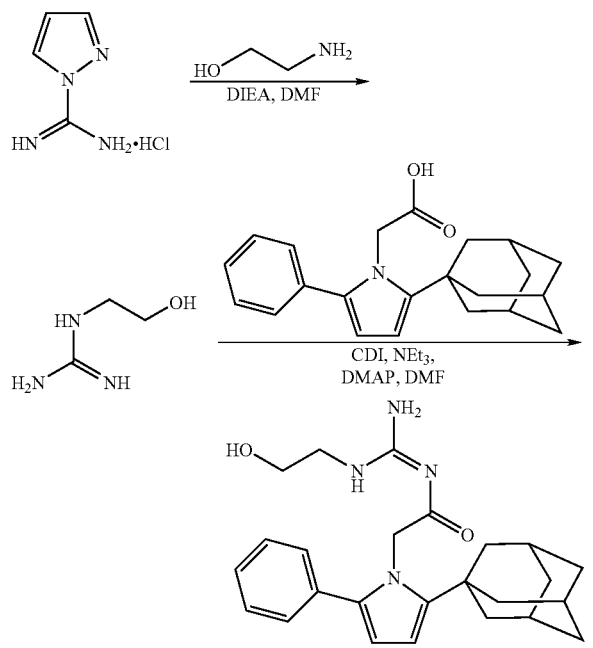

| Ex. No. | R3 | Observed Ion | HPLC (min) |
|---|---|---|---|
| 390 | ethyl | 405.4 [(M + H] | 2.1 |
| 391 | n-propyl | 419 [M + H] | 2.87 |
| 392 | n-pentyl | 447 [M + H] | 3.04 |
| 393 | (CH$_2$)$_3$—CN | 444.4 [(M + H] | 2.9 |
| 394 | (CH$_2$)$_2$—OAc | 463 [M + H] | 2.69 |
| 395 | (CH$_2$)$_3$—OH | 435.4 [(M + H] | 2.9 |

EXAMPLE 396

(2-[2-(1-adamantyl)-5-phenyl-1H-pyrrol-1-yl]-N-{(1E)-amino[(2-hydroxyethyl)-amino]methylene}acetamide)

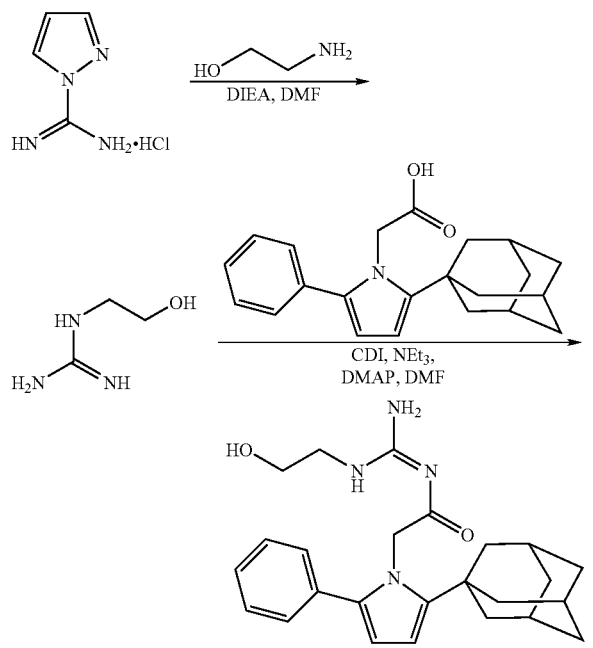

Step 1. To a solution of 1-H-pyrazole-1-carboxamidine HCl in 2.0 mL DMF was added one equivalent of DIEA. The reaction was stirred for 15 minutes at room temperature and added to a 20 mL glass scintillation vial containing 1 equivalent of ethanol amine. The reaction was mixed at room temperature overnight. The reaction was concentrated, the residue was triturated with CH$_2$Cl$_2$, and the CH$_2$Cl$_2$ layer was pipetted off. The remaining residue was dried under vacuum overnight.

Step 2. To a solution of one equivalent of 2-adamantan-1-yl-5-phenyl-pyrrol-1-yl)-acetic acid in 2.0 mL DMF was added 5 equivalents of N,N'-carbonyldiimidazole. The solution was stirred at room temperature for 1 hour, upon which time 5 equivalents of alkyl guanidine from Step 1, 10 equivalents of triethylamine, and 10 mol % DMAP were added. The mixture was stirred at room temperature overnight. The reaction was concentrated and the residue is dissolved in a mixture of DMSO, MeOH and water (1.5 mL total) and purified by Gilson preparative HPLC system, R. T. 2.59, M+H 433. HPLC conditions: YMC Pro C18 column, 20 mm×50 mm ID, 5 µM; 2 mL injection; Solvent A: Water (0.05% NH$_4$OH buffer); Solvent B: acetonitrile (0.05 µM NH$_4$OH buffer); Gradient: Time 0: 5% B; 2 min: 5% B; 12 min: 95% b, Hold 95% B 3 min; Flow rate 22.5 mL/min; Detection: 254 nm DAD.

EXAMPLES 397-399

Preparation of (2-[2-(1-adamantyl)-5-phenylpyrrole Acylguanidine Derivatives

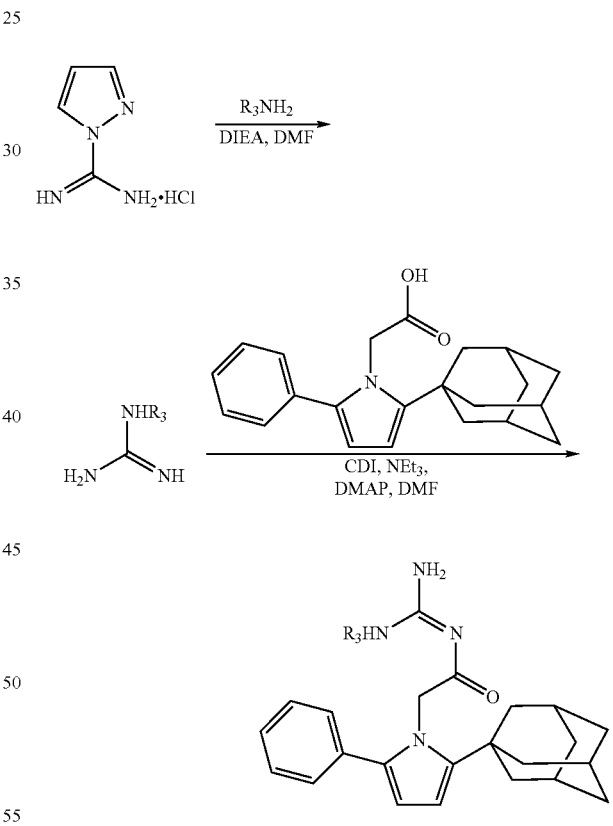

Using essentially the same procedure described in Example 396 and employing the appropriate amine, R$_3$NH$_2$, the compounds shown in Table XVIII were prepared and identified by HPLC and mass spectral analyses. HPLC Conditions: HP 1100 HPLC system; Waters Xterra MS C$_{18}$ column, 2 mm (i.d.)×50 mm×2 mm, 3.5µ particle size, set at 50° C.; flow rate 1.0 mL/min; Solvent A: 0.05% NH$_4$OH in water; Solvent B: 0.05% NH$_4$OH in ACN; Gradient: Time 0: 10% B; 2.5 min: 90% B; 3 min: 90% B; Sample concentration: ~2.0 mM; Injection volume: 5 μL; Detection: 254 nm DAD, API-ES Scanning Mode Negative 150-700; Fragmentor 70 mV.

TABLE XVIII

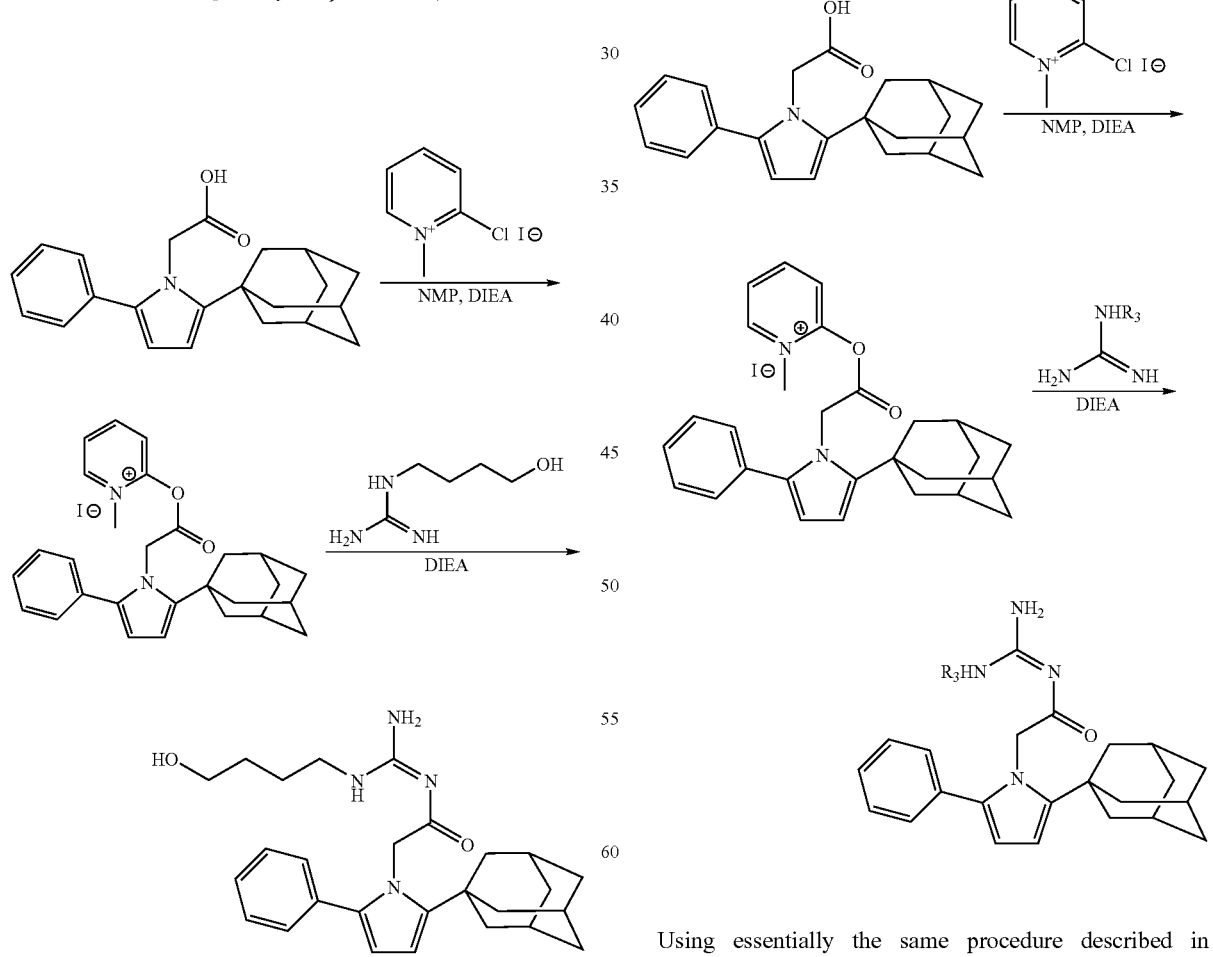

| Ex. No. | R3 | Observed Ion | HPLC (min) |
|---|---|---|---|
| 397 | $(CH_2)_2$—CN | 430 [M + H] | 2.55 |
| 398 | $(CH_2)_2$-dioxolane | 477 [M + H] | 2.68 |
| 399 | thien-2-ylmethyl | 473 [M + H] | 2.69 |

EXAMPLE 400

Preparation of (2-[2-(1-Adamantyl)-5-phenyl-1H-pyrrol-1-yl]-N-{(1E)-amino[(4-hydroxybutyl)amino]-methylene}acetamide)

Step 1. To a solution of 2-adamantan-1-yl-5-phenyl-pyrrol-1-yl)-acetic acid (1 eq.) in 1.3 mL N-methylpyrrolidinone was added 2-chloro-1-methyl-pyridinium iodide (1.1 eq.). The reaction was stirred for 2 hours at room temperature and added to a 20 mL glass scintillation vial containing 1.2 equivalents of hydroxybutyl guanidine and 2.9 equivalents of DIEA. The reaction was mixed at room temperature overnight. The reaction was concentrated and the residue is dissolved in a mixture of DMSO, MeOH and water (1.5 mL total) and purified by Gilson preparative [4]HPLC system, R. T. 2.75, M+H 449.5. HPLC conditions: YMC Pro C18 column, 20 mm×50 mm ID, 5 μM; 2 mL injection; Solvent A: Water (0.05% $NH_4OH$ buffer); Solvent B: acetonitrile (0.05% $NH_4OH$ buffer); Gradient: Time 0: 5% B; 2 min: 5% B; 12 min: 95% b, Hold 95% B 3 min; Flow rate 22.5 mL/min; Detection: 254 nm DAD.

EXAMPLES 401-417

Preparation of 2-(1-Adamantyl)-5-phenylpyrrole Acylguanidine Derivatives

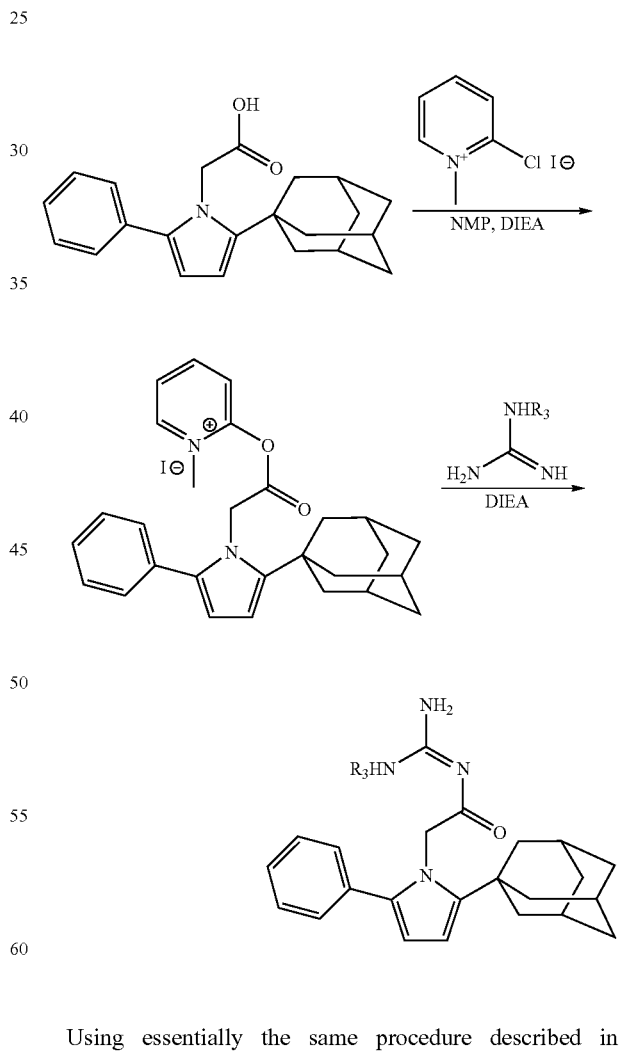

Using essentially the same procedure described in Example 400 and employing the appropriate guanidine derivative, the compounds shown in Table XIX were prepared and identified by HPLC and mass spectral analyses.

TABLE XIX

![structure with R3HN-C(=NH)(NH2)-N=... attached to acetamide on N of pyrrole bearing phenyl and 1-adamantyl]

| Ex. No. | R3 | Observed Ion | ¹HPLC (min) |
|---|---|---|---|
| 401 | 2-furylmethyl | 457 [M + H] | 2.94 |
| 402 | tetrahydrofuran-2-ylmethyl | 461 [M + H] | 2.91 |
| 403 | Cyclohexyl | 459.5 [M + H] | 3.1 |
| 404 | (2R)-2-hydroxypropyl | 435.5 [M + H] | 2.76 |
| 405 | (2S)-2-hydroxypropyl | 435.5 [M + H] | 2.75 |
| 406 | 2,3-dihydroxypropyl | 451.6 [M + H] | 2.84² |
| 407 | i-butyl | 433.5 [M + H] | 3.63² |
| 408 | 2,2,2-trifluoroethyl | 457.5 [M − H] | 3.64² |
| 409 | 3-ethoxycarbonyl-propyl | 491.7 [M + H] | 3.49² |
| 410 | cyclopropyl | 473 [M + H] | 3.04 |
| 411 | cyclohexylmethyl | 417.1 [M + H] | 2.78² |
| 412 | trans-4-hydroxycyclohexyl | 476.2 [M + H] | 2.61² |
| 413 | 3-(1H-imidazol-1-yl)propyl | 485.2 [M + H] | 2.66² |
| 414 | 3-methoxypropyl | 449.2 [M + H] | 2.87² |
| 415 | 2-methoxyethyl | 435 [M + H] | 2.69 |

TABLE XIX-continued

![same structure as above]

| Ex. No. | R3 | Observed Ion | ¹HPLC (min) |
|---|---|---|---|
| 416 | 2,2,3,3,3-pentafluoropropyl | 509 [M + H] | 3.06 |
| 417 | cycloheptyl | 473.2 [M + H] | 3.334 |

¹HPLC Conditions: HP 1100 HPLC system; Waters Xterra MS C₁₈ column, 2 mm (i.d.) × 50 mm × 2 mm, 3.5 μ particle size, set at 50° C.; flow rate 1.0 mL/min; Solvent A: 0.05% NH₄OH in water; Solvent B: 0.05% NH₄OH in ACN; Gradient: Time 0:10% B; 2.5 min: 90% B; 3 min: 90% B; Sample concentration: ~2.0 mM; Injection volume: 5 μL; Detection: 254 nm DAD, API-ES Scanning Mode Negative 150-700; Fragmentor 70 mV.

²HPLC Conditions (except as noted): Hewlett Packard 1100 MSD with ChemStation Software; Keystone Aquasil C₁₈ column, 50 mm × 2 mm, 5μ particle size, at 40° C.; Solvent A: 10 mM NH₄OAc; Solvent B: acetonitrile; Gradient: Time 0: 5% B; 2.5 min 95% B; Hold 95% B 4 min; Flow rate 0.8 mL/min; Detection: 254 nm DAD; API-ES Scanning Mode Negative 150-700; Fragmentor 70 mV.

EXAMPLE 418

Preparation of (2-[2-(1-Adamantyl)-5-phenyl-1H-pyrrol-1-yl]-N-((1Z)-amino{[(5-methyl-1,3,4-oxadiazol-2-yl)methyl]amino}methylene)acetamide)

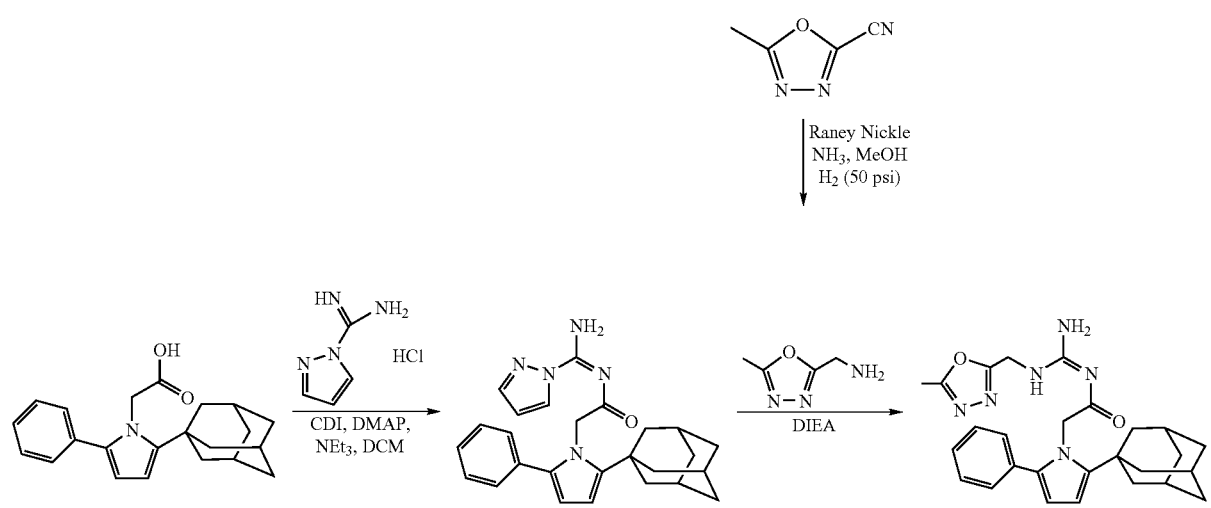

Step 1. To a solution of 1 equivalent of nitrile in 60 mL of 1M solution of NH$_3$ in MeOH in a hydrogenation bottle was added a mixture of 5.0 g of Raney Nickel in 80 mL of MeOH. The reaction was hydrogenated at 50 psi for approximately 5 hours. The reaction mixture was filtered through celite. The filtrate was concentrated and the residue was taken up in CH$_2$Cl$_2$ and washed with 1.0N NaOH solution. The mixture was filtered to remove the emulsion. The organic and aqueous layers were separated. The organic extract was dried over Na$_2$SO$_4$ and concentrated to give the desired amines.

Step 2. To a solution of 1 equivalent of the phenylpyrrole acetic acid in 4.0 mL CH$_2$Cl$_2$ was added 5 equivalent N,N'-carbonyldiimidazole. The solution was stirred at room temperature for 1 hr, upon which time 5 equivalents of 1-H-pyrazole-1-carboxamidine HCl, 10 equivalents of triethylamine and 10 mol % DMAP were added. The mixture was stirred at room temperature for 2½ hours. The reaction was filtered and the organic layer was washed with water, dried over MgSO$_4$, and concentrated.

Step 3. The residue from Step 2 was taken up in CH$_2$Cl$_2$ and 3 equivalents of DIEA and amine were added. The reaction was stirred at room temperature overnight. The reaction was concentrated and the residue is dissolved in a mixture of DMSO, MeOH and water (1.5 mL total) and purified by Gilson preparative HPLC system, R. T. 2.32, M+H 473. HPLC conditions: YMC Pro C18 column, 20 mm×50 mm ID, 5 μM; 2 mL injection; Solvent A: Water (0.05% NH$_4$OH buffer); Solvent B: acetonitrile (0.05% NH$_4$OH buffer); Gradient: Time 0: 5% B; 2 min: 5% B; 12 min: 95% b, Hold 95% B 3 min; Flow rate 22.5 mL/min; Detection: 254 nm DAD.

EXAMPLES 419-430

Preparation of 2-(1-Adamantyl)-5-phenylpyrrole Acylguanidine Derivatives

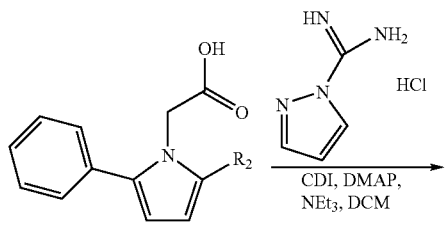

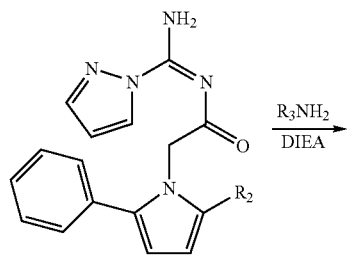

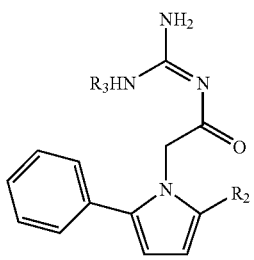

Using essentially the same procedure described in Example 418 and employing the appropriate amino acid, the compounds shown in Table XX are prepared and identified by HPLC and mass spectral analyses. HPLC Conditions: HP 1100 HPLC system; Waters Xterra MS C$_{18}$ column, 2 mm (i.d.)×50 mm×2 mm, 3.5μ particle size, set at 50° C.; flow rate 1.0 mL/min; Solvent A: 0.05% NH$_4$OH in water; Solvent B: 0.05% NH$_4$OH in ACN; Gradient: Time 0: 10% B; 2.5 min: 90% B; 3 min: 90% B; Sample concentration: ~2.0 mM; Injection volume: 5 μL; Detection: 254 nm DAD, API-ES Scanning Mode Negative 150-700; Fragmentor 70 mV.

TABLE XX

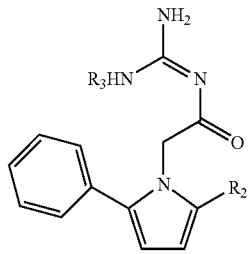

| Ex. No. | R3 | R2 | [M + H] | HPLC (min) |
|---|---|---|---|---|
| 418 | 5-methyl-1,3,4-oxadiazol-2-yl)methyl | adamantyl | | |
| 419 | (4-methyl-1,3-thiazol-2-yl)methyl | adamantyl | 488 | 2.45 |
| 420 | 2-thien-2-ylethyl | adamantyl | 487 | 2.53 |
| 421 | 3-aminobenzyl | adamantyl | 482 | 2.42 |
| 422 | 2-thien-3-ylethyl | adamantyl | 487 | 2.54 |
| 423 | (5-methyl-1,3,4-oxadiazol-2-yl)methyl | 4-allylcarbamoyl-phenyl | 498 | 2.03 |
| 424 | (4-methyl-1,3-thiazol-2-yl)methyl | 4-allylcarbamoyl-phenyl | 513 | 2.18 |

TABLE XX-continued

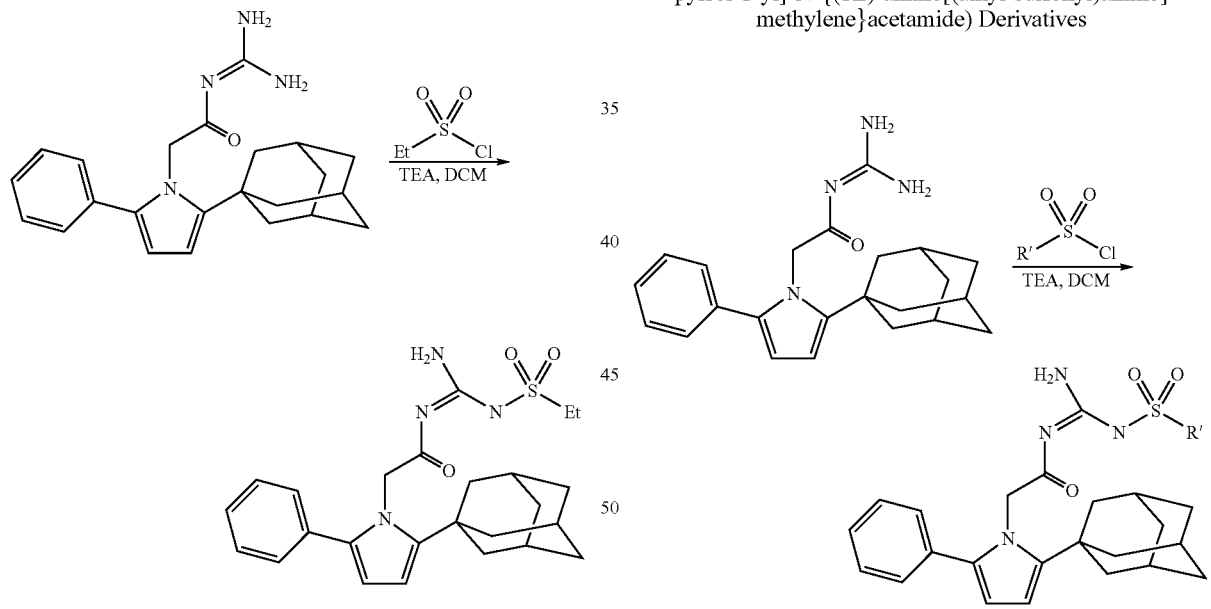

| Ex. No. | R3 | R2 | [M + H] | HPLC (min) |
|---|---|---|---|---|
| 425 | 2-thien-2-ylethyl | 4-allylcarbamoyl-phenyl | 512 | 1.94 |
| 426 | 3-aminobenzyl | 4-allylcarbamoyl-phenyl | 507 | 2.1 |
| 427 | 2-thien-3-ylethyl | 4-allylcarbamoylphenyl | 512 | 2.24 |
| 428 | 1H-indol-3-ylmethyl | 4-allylcarbamoyl-phenyl | 531 | 2.22 |
| 429 | 1H-pyrrol-2-ylmethyl | 4-allylcarbamoyl-phenyl | 481 | 2.15 |
| 430 | 5-acetyl-thiophen-2-ylmethyl | 4-allylcarbamoyl-phenyl | 540 | 1.72 |

EXAMPLE 431

Preparation of (2-[2-(1-adamantyl)-5-phenyl-1H-pyrrol-1-yl]-N-{(1Z)-amino[(ethyl-sulfonyl)amino]methylene}acetamide)

A solution of 1 equivalent of N-[2-(2-adamantan-1-yl-5-phenyl-pyrrol-1-yl)-acetyl]-guanidine in 2.0 mL CH$_2$Cl$_2$ was cooled to 7° C. To the solution 1.0 equivalent of triethylamine was added. The reaction was stirred for 10-15 minutes, after which time ethylsulfonyl chloride was added. The reaction was concentrated and the residue is dissolved in a mixture of DMSO, MeOH and water (1.5 mL total) and purified by Gilson preparative HPLC system. HPLC conditions: YMC Pro C18 column, 20 mm×50 mm ID, 5 uM; 2 mL injection; Solvent A: Water (0.05% NH$_4$OH buffer); Solvent B: acetonitrile (0.05% NH$_4$OH buffer); Gradient: Time 0: 5% B; 2 min: 5% B; 12 min: 95% b, Hold 95% B 3 min; Flow rate 22.5 mL/min; Detection: 254 nm DAD. [M+H] 469, retention time 2.7 min.

EXAMPLES 432-434

Preparation of (2-[2-(1-adamantyl)-5-phenyl-1H-pyrrol-1-yl]-N-{(1Z)-amino[(alkyl-sulfonyl)amino]methylene}acetamide) Derivatives Using essentially the same procedure described in Example 431 and employing the appropriate alkylsulfonyl chloride, R'SO$_2$Cl, the compounds shown in Table XXI are prepared and identified by HPLC and mass spectral analyses. HPLC Conditions: HP 1100 HPLC system; Waters Xterra MS C$_{18}$ column, 2 mm (i.d.)×50 mm×2 mm, 3.5μ particle size, set at 50° C.; flow rate 1.0 mL/min; Solvent A: 0.05% NH$_4$OH in water; Solvent B: 0.05% NH$_4$OH in ACN; Gradient: Time 0: 10% B; 2.5 min: 90% B; 3 min: 90% B; Sample concentration: ~2.0 mM; Injection volume: 5 μL; Detection: 254 nm DAD, API-ES Scanning Mode Negative 150-700; Fragmentor 70 mV.

TABLE XXI

| Ex. No. | R' | Observed Ion [M + H] | HPLC (min) |
|---|---|---|---|
| 432 | 3-Cl-propylsulfonyl | 517 | 2.78 |
| 433 | butylsulfonyl | 497 | 2.83 |
| 434 | propylsulfonyl | 483 | 2.77 |

EXAMPLE 435

Preparation of (N''-({2-[5-(hydroxymethyl)-1-naph-thyl]-5-phenyl-1H-pyrrol-1-yl}acetyl)guanidine)

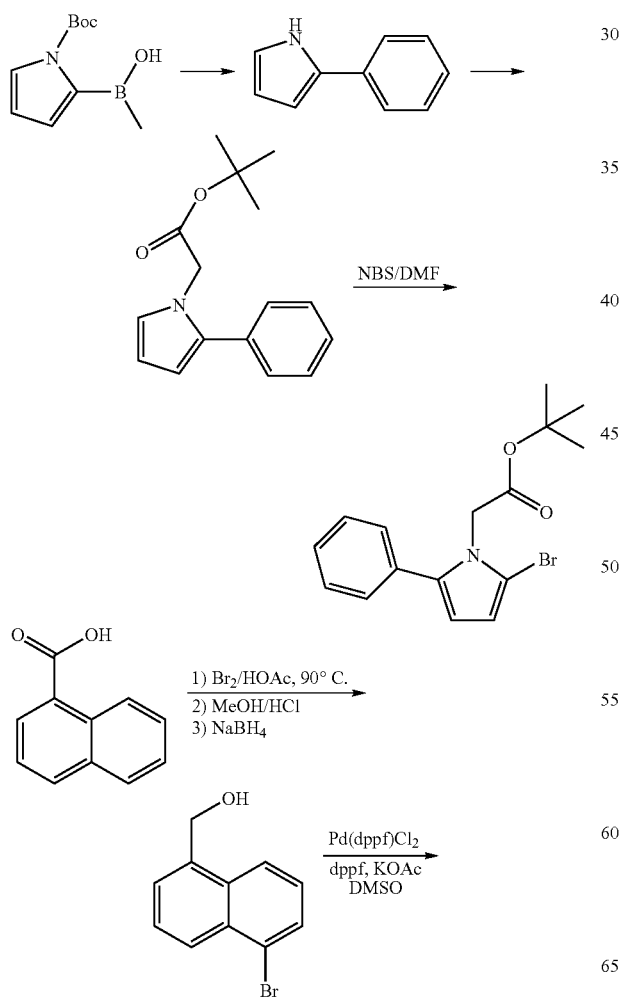

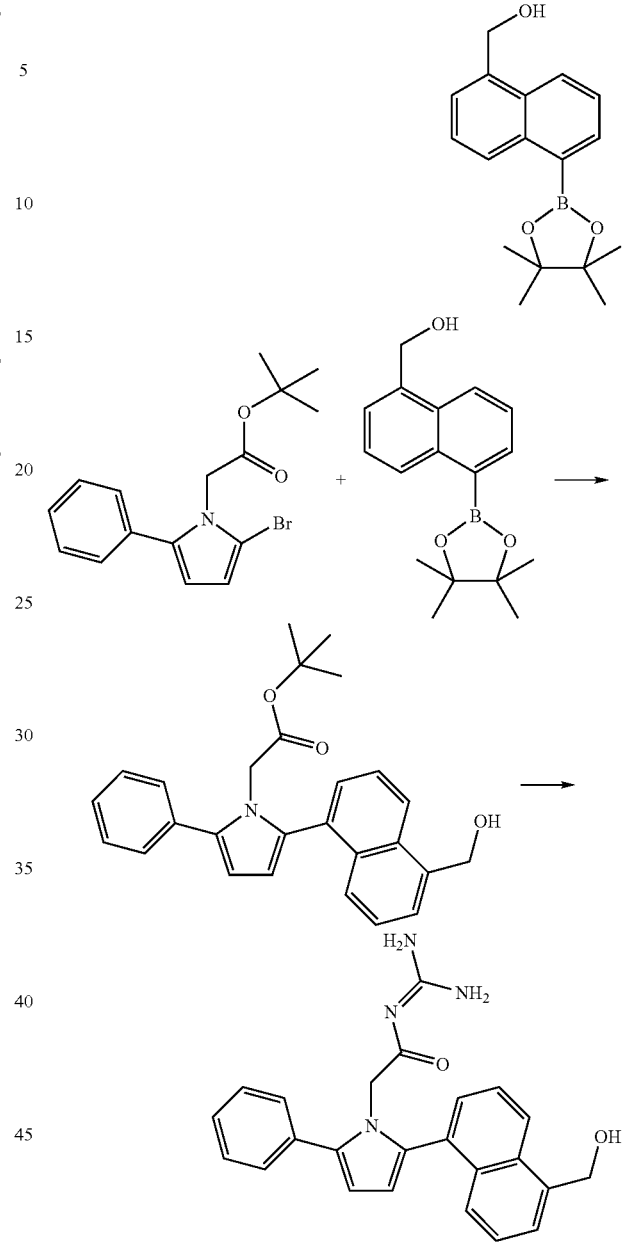

Step 1: 1-(t-butoxycarbonyl)pyrrole-2-boronic acid (Frontier Scientific, 15.2731 g, 72.38 mmol) was combined with $K_3PO_4$ (18.4967 g, 87.13 mmol), bromobenzene (9 mL, 85.6 mmol), DMF (570 mL) and ~10 mL MeOH. This heterogeneous mixture was freeze-thaw degassed 3 times and tetrakis(triphenylphosphine)palladium (0) (941.0 mg, 0.812 mmol) was added. The resultant heterogeneous mixture was heated at 60° C. for 3 d, then combined with EtOAc (800 mL) and washed with water (500 mL) followed by brine (2×500 mL). The organic extracts were dried ($Na_2SO_4$), concentrated, and purified (15% EtOAc/Hex) to give product as a white solid (60%, 6.2175 g, 43.42 mmol).

Step 2: 2-Phenyl-1H-pyrrole (1.9071 g, 9.036 mmol) was dissolved in DMF (20 mL). This solution was added dropwise to a cooled (ice/$H_2O$) stirring slurry of NaH (810.1 mg, 20.3 mmol) in DMF (15 mL). After the bubbling had subsided, tert-butyl bromoacetate (8 mL, 54.2 mmol) in DMF (10 mL) was added to the stirring solution dropwise. After 30 m, a pink heterogeneous mixture was quenched with sat. NaHCO₃ (aq), dumped into EtOAc (250 mL), and washed with brine (3×250 mL). The combined organic extracts were dried (Na₂SO₄), then purified (5% EtOAc/Hex, silica gel) to give product as a yellow oil (75%, 2.5730 g, 10.00 mmol).

Step 3: To a dry flask was added N-(t-butoxycarbonyl) methyl-2-phenylpyrrole (131 mg) and anhydrous DMF (2.5 mL). The flask was cooled with an ice bath before the slow addition of a solution of NBS (1.0 equiv.) in DMF (1.0 mL). After 5 min, the reaction was completed and the product was extracted with ethyl acetate. The crude product was purified by flash chromatography (eluted with hexane). The purified product (142 mg) was kept as a solution in toluene.

Step 4: To a dry three-neck round-bottomed flask was added with 1-naphthoic acid (17.22 g, 0.1 mol) and acetic acid (40 mL). The solution was heated to 90° C. and then bromine (5.3 mL0 was added dropwise in a period of 30 min. The reaction mixture was stirred at 90° C. for 90 min and heating was turned off. The mixture was then stirred at rt overnight before work-up.

Step 5: To a dry flask was added with anhydrous methanol (100 mL). The flask was cooled with a ice-bath, acetyl chloride (10 mL) was added slowly to the flask. After stirred for 15 min, the above bromination product (7.50 g, 30 mmol) was added. The mixture was refluxed for 5 h and the solvent was removed by rotary evaporation and the crude was dissolved into ethyl acetate (200 mL). The solution was washed with saturated aqueous sodium carbonate solution four times, followed with brine. After dried with anhydrous sodium sulfate, the solution was concentrated to give methyl 5-bromo-1-naphthate (7.90 g).

Step 6: The product obtained above (6.84 g) was dissolved into THF-Methanol (3:1) (50 mL). Cooled with a water bath, the solution was added with sodium borohydride (excess) and the reaction mixture was stirred at rt overnight. The reaction was diluted with ethyl acetate and saturated ammonium chloride aqueous solution. The two layers were separated and the aqueous layer was extracted with ethyl acetate twice. The combined organic layers were dried over anhydrous sodium sulfate and concentrated over vacuum. Purification with flash chromatography gave 5-bromo-1-hydroxymethylnaphthalene (5.10 g) as the product.

Step 7: To a round-bottomed flask was added with 5-bromo-1-hydroxymethylnaphthalene (1.02 g, 4.3 mmol), bispinacollatoboron (1.1 equiv.), Pd(dppf)Cl2 (0.03 equiv.), dppf (0.03 equiv.), potassium acetate (3.0 equiv.) and DMSO (6 mL). The mixture was de-gassed and heated to 80° C. under argon. The reaction was allowed to proceed at 80° C. under argon overnight and then diluted with with ethyl acetate and water. The two layers were separated and the aqueous layer was extracted with ethyl acetate twice. The combined organic layers were dried over anhydrous sodium sulfate and concentrated over vacuum. Purification with flash chromatography gave the boronic ester product (0.53 g).

Step 8. To a solution of the pyrrole bromide (0.3 mmol) in toluene (2 mL), MeOH (0.5 mL) and 2 M NaHCO3 (1 mL) was added the boronic acid (0.06 g, 1.3 eq) and palladium tetrakistriphenylphosphine (0.02 g). NOTE: All solvents were individually degassed. The reaction mixture was stirred for 13 hr at 80° C., worked up with brine/EtOAc, dried (MgSO₄), filtered and concentrated. Chromatography (silica, EtOAc/hexanes) afforded the desired products (40-70%).

Step 9: To a solution of N-2-[2-(5-Hydroxymethyl-naphthalen-1-yl)-5-phenyl-pyrrol-1-yl]-acetic acid t-butyl ester (0.14 mmol) in MeOH (0.1 mL) is added activated 3 angstrom molecular sieves. This mixture was allowed to stir 15 min. A solution of guanidine HCl (3 mmol) and NaOMe (2 mmol) in MeOH (dried over molecular sieves, degassed, 2 mL) over dry sieves was prepared. 0.55 mL (~0.55 mmoL) of the solution was added and stirred at 55° C. overnight. The reaction was worked up with brine/EtOAc, dried over Na₂SO₄, filtered and concentrated. The crude product was purified by flash chromatography (ethyl acetate-5% methanol in ethyl acetate) to provide the title compound (32.5 mg, yield 29%). LC-MS MH⁺ (m/z) 399.4.

EXAMPLE 436

Preparation of (N-{[2-(6-hydroxy-1-benzofuran-3-yl)-5-phenyl-1H-pyrrol-1-yl]acetyl}-guanidine)

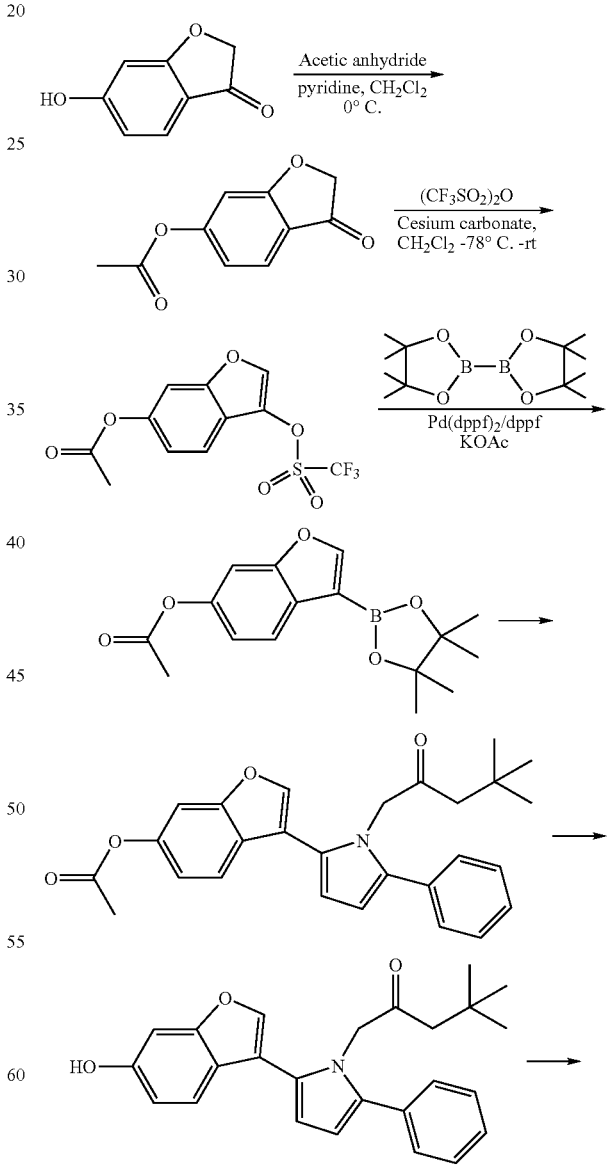

-continued

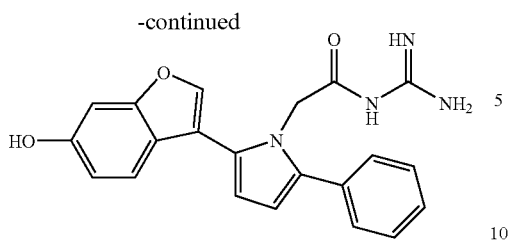

Step 1: To a dry round-bottom flask was added 6-hydroxybenzofuran-3-one (5.03 g, 33.5 mmol), dichloromethane (30 mL) and pyridine (3.2 mL, 40 mmol, 1.2 equiv.). The mixture was cooled with an ice bath and then added with acetic anhydride (3.42 g, 1.0 equiv.). The ice bath was removed and the reaction was allowed to proceed at rt overnight. The reaction mixture was then diluted with ethyl acetate (80 mL) and sat. aqueous solution of ammonium chloride (30 mL). The organic layer and aqueous layer were separated and the aqueous layer was extracted with ethyl acetate twice. The combined organic layers were washed with brine once and dried over sodium sulfate before concentrated with rotary evaporation. The crude product was purified by trituration with ether twice to give the pure product (5.18 g) with a yield of 80%.

Step 2: To a dry round-bottom flask was added 6-acetoxybenzofuran-3-one (1.91 g, 10.0 mmol), anhydrous dichloromethane (30 mL) and cesium carbonate (30 mmol). The mixture was cooled with a dry ice/acetone bath and then added with triflic anhydride (1.68 mL, 1.0 equiv.). The dry ice bath was removed and the temperature slowly reached to rt. The reaction was monitored by TLC. After stirred at rt for 2 h, the reaction was completed and the solid was removed by filtration. The filter was concentrated. Flash chromatography gave 2.35 g (72%) of pure product.

Step 3: To a round-bottom flask was added 6-acetoxy-3-hydroxy-benzofuran triflate (2.35 g, 7.25 mmol), potassium acetate (2.14 g, 21.8 mmol), bispinacollatoboron (1.1 equiv.), Pd(dppf)Cl2 (0.03 equiv.), dppf (0.03 equiv.), and dioxane (30 mL). The mixture was de-gassed and heated to 80° C. under argon. The reaction was allowed to proceed at 80° C. under argon for 20 h and then diluted with ethyl acetate (30 mL) and water (15 mL). The two layers were separated and the aqueous layer was extracted with ethyl acetate twice. The combined organic layers were dried over anhydrous sodium sulfate and concentrated over vacuum. Flash chromatography gave the boronic ester product (1.51 g, yield 69%).

Step 4: To a round-bottom flask was added 6-acetoxybenzofuran-3-yl pinacollatoboronate (780 mg, 2.58 mmol), toluene (3.0 mL), 2.0 M aqueous solution of cesium carbonate (4.0 mL), Methanol (2 ml) and Pd(PPh3)4 (0.077 mmol). A solution of t-butyl 2-bromo-5-phenylpyrrolyl-N-acetate in toluene (2.58 mmol, 1.0 equiv.) was then added and the mixture was de-gassed by vacuum and heated to 80° C. under argon. The reaction was allowed to proceed at 80° C. under argon for overnight and then diluted with ethyl acetate (20 mL) and water (5 mL). The two layers were separated and the aqueous layer was extracted with ethyl acetate twice. The combined organic layers were dried over anhydrous sodium sulfate and concentrated over vacuum. Flash chromatography gave the coupled product N-{2-[2-(6-hydroxybenzofuran-3-yl)-5-phenylpyrrol-1-yl]-acetic acid t-butyl ester (150 mg, yield 15%).

Step 5: N-{2-[2-(6-Hydroxy-benzofuran-3-yl)-5-phenylpyrrol-1-yl]-acetyl}-guanidine was prepared by the standard guanidinolysis procedure using N-{2-[2-(6-Hydroxybenzofuran-3-yl)-5-phenylpyrrol-1-yl]-acetic acid t-butyl ester. The crude was purified by HPLC to provide the desired product (15 mg, yield 35%). LC-MS M–H⁻ (m/z) 373.4.

EXAMPLES 437-454

Preparation of 2-Aryl-5-phenylpyrrole Acylguanidine Derivatives

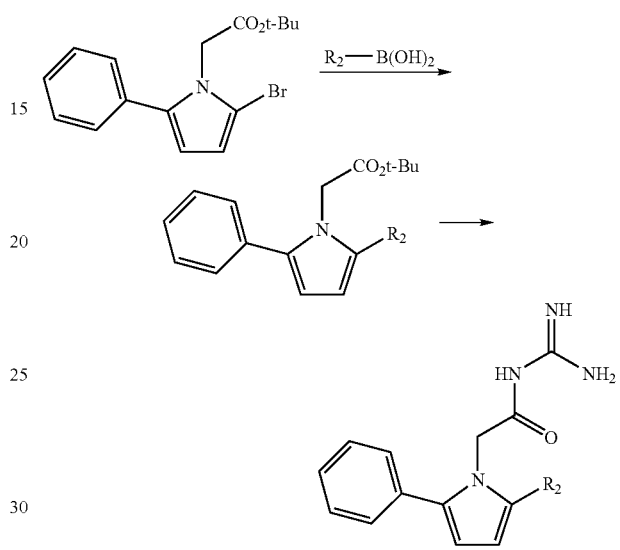

Using essentially the same procedures described in Examples 435 and 436 hereinabove, and employing the appropriate boronic acid, R₂—B(OH)₂, the compounds shown on Table XXII were prepared and identified by HNMR and mass spectral analyses.

TABLE XXII

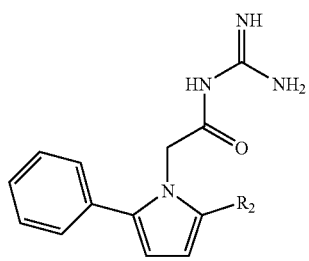

| Ex. No. | R2 | LC-MS (m/z) |
|---|---|---|
| 437 | 2-methoxyphenyl | 349.4 |
| 438 | 2-cyanophenyl | 344.3 |
| 439 | 3-fluoro-2-methoxyphenyl | 367.3 |
| 440 | 2-(hydroxymethyl)phenyl | 349.3 |
| 441 | 4-amino-2-methylphenyl | 348.2 |
| 442 | 3-(hydroxymethyl)phenyl | 349.4 |
| 443 | 3-acetylphenyl | 361.3 |
| 444 | 4-benzamido | 362.3 |
| 445 | 1-acetyl-2,3-dihydro-1H-indol-5-yl | 402.5 |
| 446 | 3-hydroxyphenyl | 335.4 |
| 447 | 4-(1-propionyl)phenyl | — |
| 448 | 3,5-dimethylphenyl | — |
| 449 | 4-n-butylphenyl | 375.4 |
| 450 | 2,5-dimethylphenyl | 347.3 |
| 451 | 4-(cyanomethyl)phenyl | 358.3 |
| 452 | 2-(trifluoromethyl)phenyl | 387.3 |

TABLE XXII-continued

| Ex. No. | R2 | LC-MS (m/z) |
|---|---|---|
| 453 | 3-(cyanomethyl)phenyl | 358.3 |
| 454 | 4-(2-cyanoethyl)phenyl | 372.5 |

EXAMPLE 455

Preparation of (N''-[(2-benzoyl-5-phenyl-1H-pyrrol-1-yl)acetyl]guanidine)

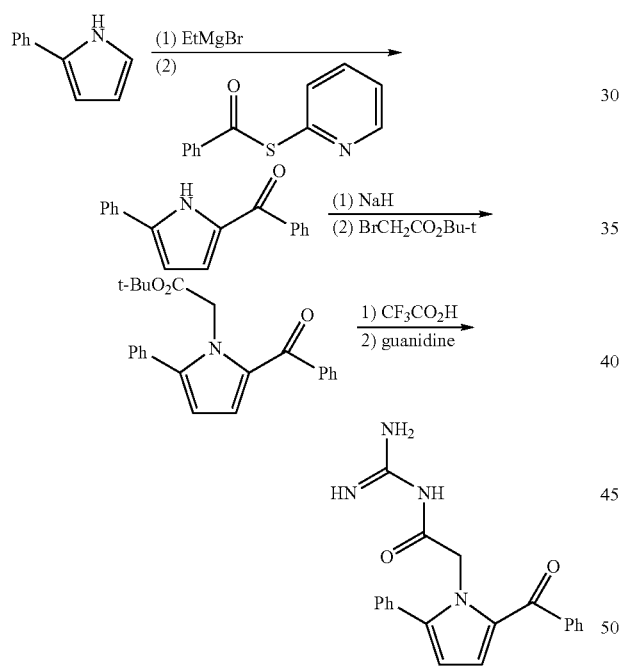

Step 1. Phenyl-(5-phenyl-1H-pyrrol-2-yl)methanone

To a stirred solution of 2-phenyl-1H-pyrrole (354 mg, 2.48 mmol) was added a solution of EtMgBr (0.81 ml, 2.43 mmol, 3.0M in $Et_2O$) in THF (4 ml) at room temperature. After stirring for 10 minutes, the reaction mixture was cooled to −78° C. and treated with a solution of S-pyridin-2-yl benzenecarbothioate (533 mg, 2.48 mmol) in THF (5 ml). After stirring for 10 minutes at −78° C., the reaction mixture was warmed up to room temperature and stirred over night. The reaction was quenched with saturated $NH_4Cl$ and acidified with aqueous 2N HCl (2.5 ml). The two layers were separated and the organic layer was washed with aqueous 2N HCl, dried ($MgSO_4$), filtered and concentrated. The crude material was purified by chromatography (silica gel, EtOAc/hexane: 5/50) to afford the titled compound (290 mg, 48%) as a solid: mp, 159-162° C.; MS (+) ES, 248 (M+H)$^+$.

Step 2. tert-butyl(2-benzoyl-5-phenyl-1H-pyrrol-1-yl)acetate

To a stirred solution of phenyl(5-phenyl-1H-pyrrol-2-yl)methanone (399 mg, 1.62 mmol) in THF (10 ml) was added NaH (78 mg, 1.95 mmol, 60% in mineral oil) at room temperature. After stirring for 30 minutes, the reaction mixture was treated with tetra-butyl bromoacetate (0.52 ml, 3.23 mmol). The reaction was stirred for 48 h at room temperature and quenched with ice water (25 ml). The two layers were separated and the aqueous layer was extracted with EtOAc (2×50 ml). The combined organic extracts were washed with $H_2O$ (50 ml), brine (50 ml), dried ($MgSO_4$), filtered and concentrated. The crude material was purified by chromatography (silica gel, EtOAc/hexane: 3/50) to produce the titled compound (333 mg, 57%) as a white solid: mp 85-87° C.; MS (+) EI, 362 (M+H)$^+$.

Step 3. N-[amino(imino)methyl]-2-(2-benzoyl-5-phenyl-1H-pyrrol-1-yl)acetamide

A solution of tert-butyl(2-benzoyl-5-phenyl-1H-pyrrol-1-yl)acetate (148 mg, 0.41 mmol) in trifluoroacetic acid was stirred for 2 h at room temperature. After removal of trifluoroacetic acid, the residue was treated with $CH_2Cl_2$ (10 ml), MeOH (1 ml) and $H_2O$ (10 ml). The two layers were separated and the aqueous was extracted with $CH_2Cl_2$ (3×10 ml). The combined organic extracts were washed with $H_2O$ (10 ml), brine (10 ml), dried ($Na_2SO_4$) filtered and concentrated. The crude material was purified by chromatography (silica gel, EtOAc/hexane/$HCO_2H$: 10/40/0.1) to afford (2-benzoyl-5-phenyl-1H-pyrrol-1-yl)acetic acid (125 mg, 100%) as an oil. To a stirred solution of (2-benzoyl-5-phenyl-1H-pyrrol-1-yl)acetic acid (260 mg, 0.85 mmol) in DMF (2.0 ml) was added 1,1'-carbonyldiimidazole (166 mg, 1.02 mmol) at room temperature. After stirring for 1 h, the reaction mixture was treated with a solution of guanidine hydrochloride (244 mg, 2.55 mmol) in DMF (2.5 ml) and triethylamine (0.54 ml, 2.55 mmol). After stirring over night, the reaction mixture was quenched with $H_2O$ (30 ml). The aqueous was extracted with $Et_2O$ (3×30 ml), EtOAc (10 ml). The combined organic extracts were dried ($Na_2SO_4$), filtered and concentrated. The crude material was purified by chromatography (silica gel; EtOAc/hexane/2M $NH_3$ in MeOH: 65/35/1) to give the titled compound (169 mg, 58%) as a white solid: mp 201-203° C.; MS (−) ES, 345 (M−H)$^−$.

EXAMPLES 456 AND 457

Preparation of (N''-[(2-Heteroaroyl-5-phenyl-1H-pyrrol-1-yl)acetyl]guanidine) Derivatives

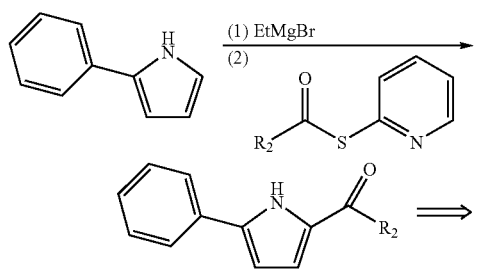

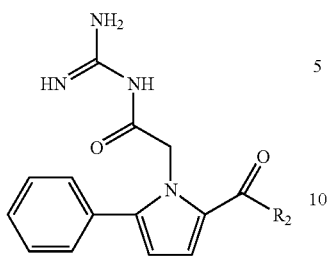

Using essentially the same procedure described in Example 455 hereinabove and employing the appropriate S-pyridin-2-yl heteroarylcarbothioate, the compounds shown on Table XXIII were prepared and identified by HNMR and mass spectral analyses.

TABLE XXIII

| Ex. No. | R2 | mp ° C. | MS |
|---|---|---|---|
| 456 | 2-furyl | 175-177 | 335 (M − H)⁻ |
| 457 | 2-thienyl | 147-149 | 254 (M + H)⁺ |

EXAMPLE 458

Preparation of N-[(2-benzyl-5-phenyl-1H-pyrrol-1-yl)acetyl]guanidine)

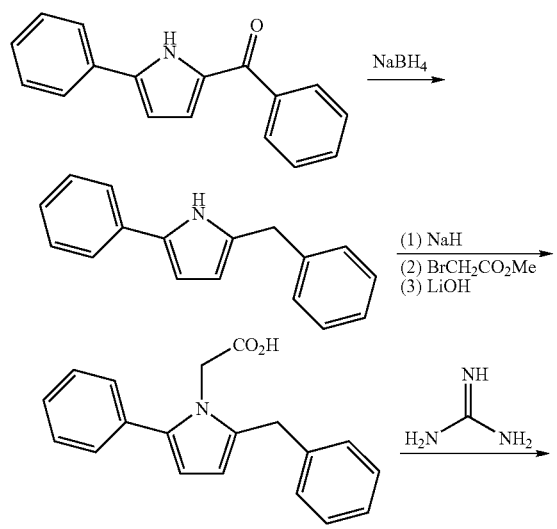

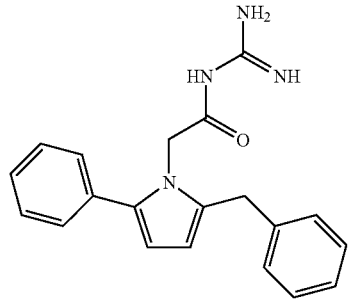

Step 1. 2-benzyl-5-phenyl-1H-pyrrole

To a solution of phenyl(5-phenyl-1H-pyrrol-2-yl)methanone (670 mg, 2.7 mmol) in iPrOH (50 ml) was added NaBH₄ (1.08 g, 27.0 mmol) at room temperature. After refluxing for 18 h, the reaction mixture was cooled and poured to cooled water (100 ml). The aqueous was extracted with CH₂Cl₂ (2×100 ml). The combined organic extracts were washed with H₂O (80 ml), brine (80 ml), dried (MgSO₄), filtered and concentrated. The crude material was purified by chromatography (EtOAc/hexane: 5/95) to give the titled compound (561 mg, 81%) as a solid: mp 82-84° C.; MS (+) ES, 233 (M+H)⁺

Step 2. methyl(2-benzyl-5-phenyl-1H-pyrrol-1-yl)acetate

To a solution of 2-benzyl-5-phenyl-1H-pyrrole (467 mg, 2.0 mmo) in DMF (5 ml) was added NaH (60% in mineral oil, 240 mg, 6.0 mmol) at room temperature in one portion. After stirring for 30 min at room temperature, the reaction mixture was heated to 60° C. and methyl bromoacetate (0.57 ml, 6.0 mmol) was added. After 1 h stirring at 60° C., the reaction was cooled and quenched with aqueous 1N HCl (30 ml). The aqueous was extracted with EtOAc (3×30 ml). The combined organic extracts were washed with aqueous 1N HCl (30 ml), H₂O (30 ml), brine (30 ml), dried (MgSO₄) and concentrated. The crude material was purified by chromatography (EtOAc/hexane: 3/97) to afford the titled compound (240 mg, 39%) as an oil: MS (+) ES, 306 (M+H)⁺.

Step 3. (2-benzyl-5-phenyl-1H-pyrrol-1-yl)acetic acid

To a solution of methyl(2-benzyl-5-phenyl-1H-pyrrol-1-yl)acetate (203 mg, 0.66 mmol) in THF (1 ml) was added aqueous 1N LiOH (1 ml) at room temperature. After 3 h stirring at room temperature, the reaction was quenched with H₂O (10 ml). The aqueous was extracted with Et₂O (2×10 ml). The aqueous was acidified with 1N HCl to pH~3, extracted with EtOAc (3×15 ml). The combined organic extracts were washed with H₂O (15 ml), brine (15 ml), dried (Na₂SO₄) and concentrated. The crude material was purified by chromatography (EtOAc/MeOH: 95/5) to provid the titled compound (185 mg, 96%) as a solid: mp 137-139° C.; MS (+) ES, 292 (M+H)⁺.

Step 4. N-[amino(imino)methyl]-2-(2-benzyl-5-phenyl-1H-pyrrol-1-yl)acetamide

To a stirred solution of (2-benzyl-5-phenyl-1H-pyrrol-1-yl)acetic acid (155 mg, 0.53 mmol) in DMF (1.0 ml) was added 1,1'-carbonyldiimidazole (172 mg, 1.06 mmol) at room temperature. After 1 h stirring, the reaction mixture was treated with a solution of guanidine carbonate (286 mg, 1.59 mmol) in DMF (2.0 ml) and triethylamine (0.22 ml, 1.59 mmol). After stirring for 18 h, the reaction mixture was quenched with H₂O (10 ml). The aqueous was extracted with EtOAc (3×30 ml). The combined organic extracts were washed with H₂O (2×30 ml), brine (30 ml), dried (Na₂SO₄), filtered and concentrated. The crude material was purified by chromatography (silica gel; EtOAc/2M NH₃ in MeOH: 97/3) to give the titled compound (130 mg, 74%) as a solid: mp 155-158° C.; MS (+) ES, 333 (M+H)⁺.

EXAMPLE 459

Preparation of N-[amino(imino)methyl]-2-[2-(2-furylmethyl)-5-phenyl-1H-pyrrol-1-yl]acetamide

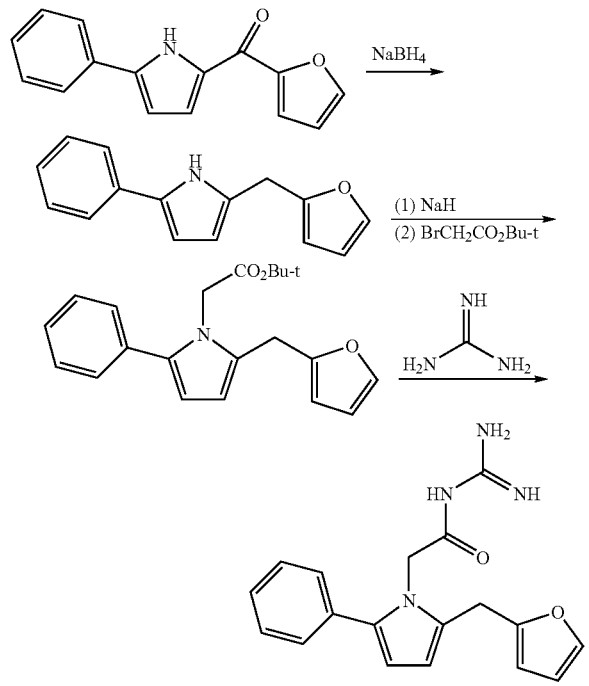

Step 1. 2-(2-furylmethyl)-5-phenyl-1H-pyrrole 2-(2-furylmethyl)-5-phenyl-1H-pyrrole was prepared by using essentially the same procedure as Example 458, step 1, as a solid (91%): mp 79-80° C.; MS (+) ES, 224 (M+H)⁺.

Step 2. tert-butyl[2-(2-furylmethyl)-5-phenyl-1H-pyrrol-1-yl]acetate tert-Butyl[2-(2-furylmethyl)-5-phenyl-1H-pyrrol-1-yl]acetate was prepared by using essentially the same procedure as Example 458, step 2, as a white solid (76%): mp 59-60° C.; MS (+) ES, 338 (M+H)⁺.

Step 3. N-[amino(imino)methyl]-2-[2-(2-furylmethyl)-5-phenyl-1H-pyrrol-1-yl]acetamide To a solution of guanidine hydrochloride in anhydrous MeOH (1.5 ml) was added powder NaOEt (80 mg. 1.17 mmol). After 10 min stirring at room temperature, the reaction mixture was treated with tert-butyl [2-(2-furylmethyl)-5-phenyl-1H-pyrrol-1-yl]acetate. After 5 h stirring at 55° C., the reaction mixture was cooled and quenched with H₂O (5 ml), diluted with EtOAc (15 ml). The organic layer was separated and the aqueous was extracted with EtOAc (2×15 ml). The combined organic extracts were washed with H₂O (15 ml), brine (15 ml), dried (Na₂SO₄) and concentrated. The crude material was purified by chromatography (silica gel; EtOAc/2M NH₃ in MeOH: 97/3) to give the titled compound (73 mg, 57%) as a solid: mp 80-82° C.; MS (−) ES, 321 (M−H)⁻.

EXAMPLE 460

Preparation of N-[amino(imino)methyl]-2-[2-phenyl-5-(thien-2-ylmethyl)-1H-pyrrol-1-yl]acetamide

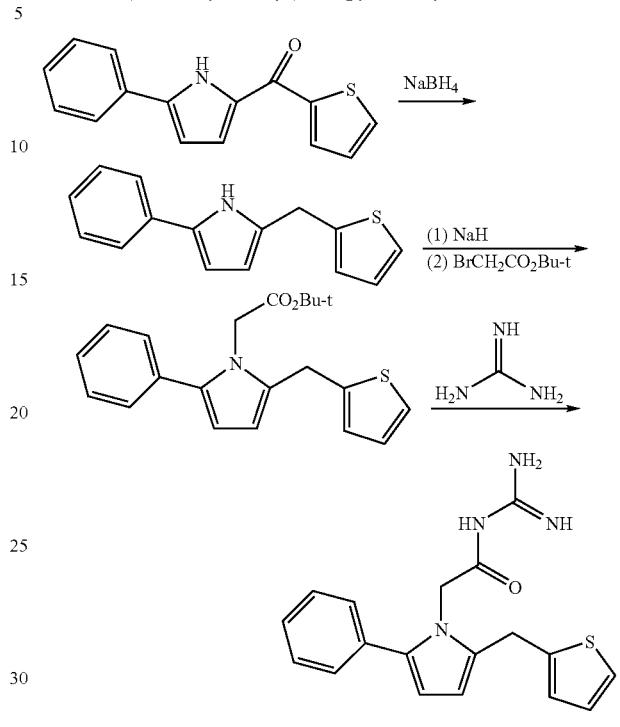

Step 1. 2-Phenyl-5-(thien-2-ylmethyl)-1H-pyrrole

2-Phenyl-5-(thien-2-ylmethyl)-1H-pyrrole was prepared by using essentially the same procedure as Example 458, step 1, as a solid (83%): compound identified by ¹HNMR.

Step 2. tert-Butyl[2-phenyl-5-(thien-2-ylmethyl)-1H-Pyrrol-1-yl]acetate tert-Butyl[2-phenyl-5-(thien-2-ylmethyl)-1H-pyrrol-1-yl]acetate was prepared by using essentially the same procedure as Example 458, step 2, as an oil (83%): compound identified by ¹HNMR.

Step 3. N-[Amino(imino)methyl]-2-[2-phenyl-5-(thien-2-ylmethyl)-1H-Pyrrol-1-yl]acetamide N-[Amino(imino)methyl]-2-[2-phenyl-5-(thien-2-ylmethyl)-1H-pyrrol-1-yl]acetamide was prepared by using essentially the same procedure as Example 459, step 3, as a solid (28%): mp 99-120° C.; MS (+) El, 339 (M+H)⁺.

EXAMPLE 461

Preparation of (N-Ethyl-4-(1-{2-[N'-(3-hydroxypropyl)-guanidino]-2-oxo-ethyl}-5-phenyl-1H-pyrrol-2-yl)-benzamide)

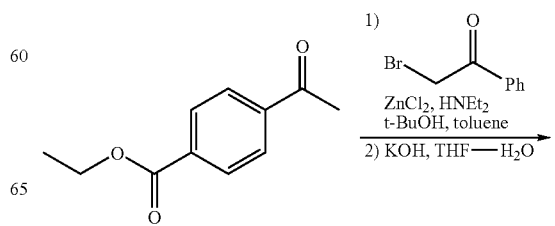

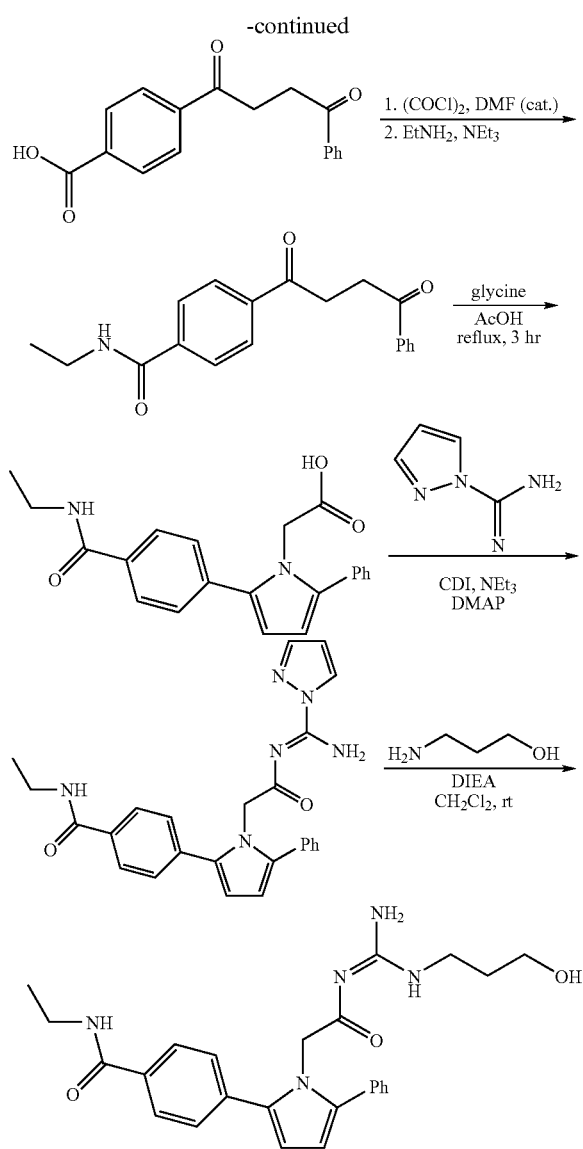

Step 1: A mixture of 5.0 g (36.6 mmol) anhydrous zinc (II) chloride, 2.8 mL (27 mmol) diethylamine, and 2.0 g t-butyl alcohol was treated with 10 mL anhydrous benzene and was stirred for 1.5 hours, treated with 5.26 g (27 mmol) ethyl (4-acetyl) benzoyl acetate and 3.58 g (18 mmol) bromoacetophenone and stirred at room temperature for 72 h. The reaction was poured into 125 mL 5% aqueous $H_2SO_4$ and extracted 2× with ethyl acetate. The organic extracts were washed with 1N HCl, dried over $MgSO_4$, and evaporated to afford a tan solid. $^1H$ NMR indicated that the crude product was a mixture in near equal proportions of the desired 4-(4-oxo-4-phenyl-butyryl)-benzoic acid ethyl ester and returned starting material ethyl (4-acetyl) benzoyl acetate. The crude product was taken on to the next step without purification.

Step 2: To a solution of 6.17 g 4-(4-oxo-4-phenyl-butyryl)-benzoic acid ethyl ester from Step 1 in 100 mL THF was added a solution of 3.86 g (69 mmol) potassium hydroxide in 110 mL water. The reaction was heated to reflux for 4.5 hr and allowed to cool. The reaction was transferred to an Ehrlenmeyer flask and cooled to 0° C. in an ice bath. Concentrated hydrochloric acid was added dropwise until a solid precipitated. The solid was collected by filtration and dried to afford 2.59 g (9.1 mmol) 4-(4-oxo-4-phenyl-butyryl)-benzoic acid.

Step 3: To a stirred slurry of 1.93 g (8 mmol) 4-(4-oxo-4-phenyl-butyryl)-benzoic acid in 22 mL $CH_2Cl_2$ was added 8 ml 2.0 M solution of oxalyl chloride in $CH_2Cl_2$, followed by 3 drops of dimethylformamide (DMF). The reaction was stirred at room temperature for 3 hr, after which time addition of additional drops of DMF showed no further evolution of gas. The reaction was concentrated and the crude acid chloride (a tan solid) was taken up in benzene and concentrated two times. A 20 mL glass scintillation vial was charged with ethyl amine (1.0 mmol, obtained as a 2.0 M solution in THF) and 0.18 mL (1.3 mmol) triethylamine. The crude acid chloride was dissolved in 32 ml $CH_2Cl_2$ and 4 mL (1.0 mmol) was added dropwise to the amine, immediately forming a precipitate. Additional 2 mL $CH_2Cl_2$ was added to slurry the precipitate and the reaction was mixed at room temperature over 3 nights. The reaction was quenched with 5 mL 0.5 M aqueous hydrochloric acid. The resulting solid was collected by filtration and dried to afford 0.159 g crude N-ethyl-4-(4-oxo-4-phenyl-butyryl)-benzamide, m/z 310 (M+H).

Step 4: To a slurry of ~1.0 mmol ethyl benzamide from Step 3 in 3 mL acetic acid was added 0.15 g (2.0 mmol) glycine. The reaction was mixed at 90-102° C. for 5.5 hr and allowed to cool. The solution was concentrated and and the residue was purified by $^6$Gilson preparative HPLC to afford 120 mg of [2-(4-ethylcarbamoyl-phenyl)-5-phenyl-pyrrol-1-yl]-acetic acid [$^5$LC-MS data molecular ion and retention time): m/z 349 (M+H); 2.36 min] as a brown solid.

Step 5: To 120 mg pyrrolyl acetic acid from Step 4 was added 97 mg (0.6 mmol, 5 equiv.) of carbonyldiimidazole and 2 mL $CH_2Cl_2$. The reaction was mixed at room temperature for one hour, upon which time was added 88 mg (5 equiv.) 1H-pyrazole-1-carboxamidine hydrochloride, 0.16 mL (10 equiv.) triethylamine, and a catalytic amount of 4-dimethylaminopyridine. The reaction was mixed at room temperature for one hour, filtered to remove any precipitates formed, and washed with water. The organic phase was separated from the aqueous phase and concentrated to afford 59 mg crude N-ethyl-4-(1-{[(imino-pyrazol-1-yl-methyl)-carbamoyl]-methyl}-5-phenyl-1H-pyrrol-2-yl)-benzamide, which was used in the next step without purification.

Step 6: To a slurry of ~0.12 mmol ethyl benzamide from Step 5 in 2 mL $CH_2Cl_2$ was added 27 mg (0.36 mmol, 3 equiv.) 3-aminopropanol and 62 μL (0.36 mmol) diisopropylethylamine and the reaction was mixed overnight at room temperature. The reaction was concentrated and the residue was purified by preparative $^6$HPLC to afford 15.8 mg of the title compound [$^5$LC-MS data (molecular ion and retention time): m/z 448 (M+H); 1.90 min] as an oil.

EXAMPLES 462-472

Preparation of (N-Alkyl-4-(1-{2-[N'-(3-hydroxypropyl)-guanidino]-2-oxo-ethyl}-5-phenyl-1H-pyrrol-2-yl)-benzamide) Derivatives

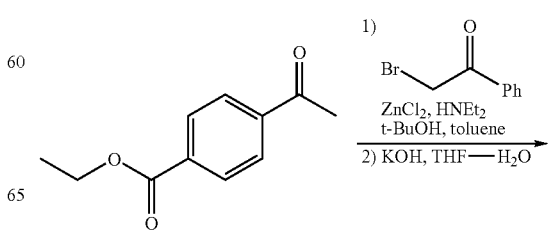

-continued

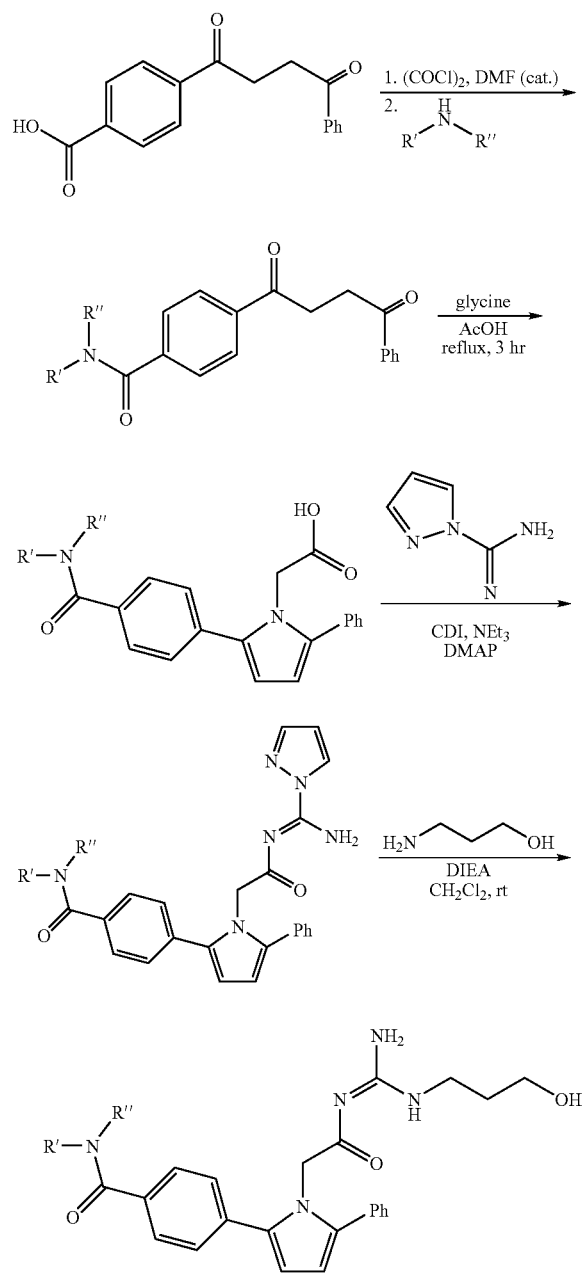

Using essentially the same procedure described in Example 461 and employing the appropriate amine HNR'R" in step 3, the compounds shown in Table XXIV were prepared and identified by HPLC and mass spectral analyses. HPLC Conditions: HP 1100 HPLC system; Waters Xterra MS C$_{18}$ column, 2 mm (i.d.)×50 mm×2 mm, 3.5μ particle size, set at 50° C.; flow rate 1.0 mL/min; Solvent A: 0.05% NH$_4$OH in water; Solvent B: 0.05% NH$_4$OH in ACN; Gradient: Time 0: 10% B; 2.5 min: 90% B; 3 min: 90% B; Sample concentration: ~2.0 mM; Injection volume: 5 μL; Detection: 254 nm DAD, API-ES Scanning Mode Negative 150-700; Fragmentor 70 mV.

TABLE XXIV

| Ex. No. | NR'R" | Observed Ion [M + H] | HPLC (min) |
|---|---|---|---|
| 462 | cyclopropylamino | 460 | 2.4 |
| 463 | allylamino | 460 | 2.4 |
| 464 | 2-hydroxyethylamino | 464 | 2.38 |
| 465 | 2-cyanoethylamino | 471 | 2.4 |
| 466 | (S)-(1-carbamoyl)ethylamino | 491 | 2.31 |
| 467 | propylamino | 462 | 2.21 |
| 468 | 2-methoxyethylamino | 478 | 2.11 |
| 469 | (rac)(1-methyl) propylamino | 476 | 2.32 |
| 470 | N-allyl-N-methylamino | 474 | 2.32 |
| 471 | N-[1,3]dioxolan-2-ylmethyl-N-methylamino | 520 | 2.25 |
| 472 | 2,2,3,3,3-pentafluoropropylamino | 552 | 2.44 |

EXAMPLE 473

Preparation of N-{(1E)-amino[(3-cyanopropyl)amino]methylene}-2-[2-phenyl-5-(trans-4-propylcyclohexyl)-1H-pyrrol-1-yl]acetamide

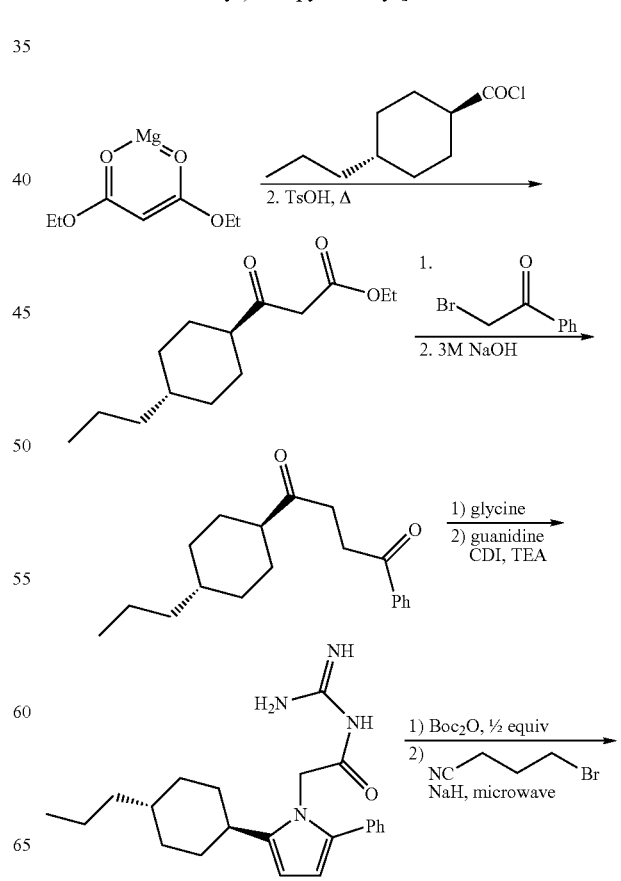

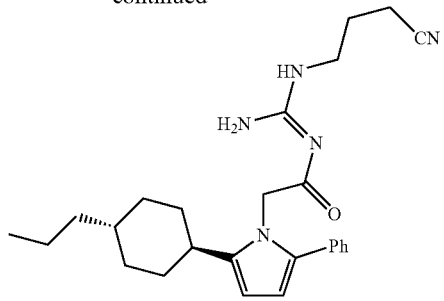

Step 1: To 2.5 mL of anhydrous EtOH and 0.25 mL carbon tetrachloride was added 1.2 g (50 mmol) magnesium turnings. 8.0 g (50 mmol) diethyl malonate was dissolved in a mixture of 5 mL anhydrous EtOH and 20 mL anhydrous toluene and added in small portions to the magnesium turnings over the course of 1.5 hr so as to maintain a gentle reflux. The reaction was stirred at room temperature for 1 hr, and then cooled to 0° C. in ice. 4-Propyl-cyclohexanecarbonyl chloride (50 mmol) was added dropwise and the reaction was allowed to warm to room temperature over night. The reaction was then heated to 55° C. for 4 hr with stirring, allowed to cool to ambient temperature, and was poured into a slurry of crushed ice and 10% $H_2SO_4$. The solution was diluted with brine and extracted with ethyl acetate. The organic layer was separated, dried over $MgSO_4$, and concentrated to afford 10.71 g (34.28 mmol) 2-(4-propyl-cyclohexanecarbonyl)-malonic acid diethyl ester as a clear, near colorless oil.

Step 2: A solution of 3.0 g (9.6 mmol) 2-(4-propyl-cyclohexanecarbonyl)-malonic acid diethyl ester and 0.3 g p-toluenesulfonic acid in 30 mL water was heated to reflux for 3 hr and allowed to stand at room temperature over 3 nights. The reaction was diluted with brine, extracted with ethyl acetate, dried over $MgSO_4$, and concentrated to afford 1.92 g (7.98 mmol) 3-oxo-3-(4-propyl-cyclohexyl)-propionic acid ethyl ester as a clear oil.

Step 3: To a stirred slurry of 0.92 g (23 mmol) NaH, 60% dispersion in mineral oil, in 30 mL anhydrous THF, cooled 0° C. in ice, 5.12 g (21.3 mmol) 3-oxo-3-(4-propyl-cyclohexyl)-propionic acid ethyl ester from Step 2 was added dropwise over the course of 60 min. The reaction was stirred at 0° C. for 1 hr. 2-bromoacetophenone (5.57 g, 28 mmol) in 12 mL anhydrous THF was then added dropwise at 0° C. and the reaction was allowed to stir at room temperature over 5 days. The reaction was poured into brine, extracted with ethyl acetate, dried over $MgSO_4$, and concentrated to afford 8.85 g (24.6 mmol, 115% yield) 4-oxo-4-phenyl-2-(4-propyl-cyclohexanecarbonyl)-butyric acid ethyl ester as an oil. The product was used in the next step without further purification.

Step 4: To a solution of 7.63 g (21.3 mmol) 4-oxo-4-phenyl-2-(4-propyl-cyclohexanecarbonyl)-butyric acid ethyl ester in 66 mL toluene was added 36 mL 3M aqueous sodium hydroxide and 0.32 g (0.96 mmol) tetra-n-butylammonium hydrogen sulfate. The reaction was heated to reflux over 16 hr, allowed to cool and poured into brine. The solution was extracted two times with ether and concentrated to give an oil. The crude product was chromatographed on silica to give 1.44 g 1-phenyl-4-(4-propyl-cyclohexyl)-butane-1,4-dione as a red solid.

Step 5: A solution of 1.43 g (5 mmol) 1-phenyl-4-(4-propyl-cyclohexyl)-butane-1,4-dione and 0.75 g (10 mmol) glycine 16 mL of acetic acid was heated to reflux for 100 min. The solution was concentrated and redissolved in 5% aqueous $H_2SO_4$. The solution was extracted with ethyl acetate. The organic phase was dried over $MgSO_4$ and concentrated to afford 0.91 g [2-phenyl-5-(4-propyl-cyclohexyl)-pyrrol-1-yl]-acetic acid as a tan solid which was carried on to the next step without purification.

Step 6: To a solution of 0.91 g (2.8 mmol) [2-phenyl-5-(4-propyl-cyclohexyl)-pyrrol-1-yl]-acetic acid in 28 mL anhydrous DMF was added 2.27 g (14 mmol) carbonyldiimidazole. The reaction was stirred at room temperature for 50 min, upon which time was added 2.52 g (14 mmol) guanidine carbonate, 0.17 g (1.4 mmol) 4-dimethylaminopyridine, and 2.83 g (28 mmol) triethylamine. The reaction was stirred at room temperature over 16 hr. The solution was filtered to remove the precipitate that formed, was diluted with ethyl acetate, and was washed three times with brine. Drying over $MgSO_4$ and concentration afforded 1.49 g of N-{2-[2-phenyl-5-(4-propyl-cyclohexyl)-pyrrol-1-yl]-acetyl}-guanidine as a yellow-brown oil. The product was observed to contain DMF by $^1$H NMR. However, it was used in the next step without further purification.

Step 7: A solution of 1.34 g (3.6 mmol) N-{2-[2-phenyl-5-(4-propyl-cyclohexyl)-pyrrol-1-yl]-acetyl}-guanidine from Step 6 in 36 mL anhydrous THF was cooled to 0° C. in ice. 1.62 mL (1.62 mmol) di-tert-butyl dicarbonate (1.0M solution in THF) was added dropwise and the reaction was stirred at 0° C. for 30 minutes. 25 mL water was added and the reaction mixture was poured into brine and extracted twice with ethyl acetate. The organic phase was concentrated and the residue was purified by Gilson preparative [4]HPLC to afford 0.23 g of the recovered guanidine and 0.133 g (0.28 mmol) of N-Boc-N'-{2-[2-phenyl-5-(4-propyl-cyclohexyl)-pyrrol-1-yl]-acetyl}-guanidine [[2]LC-MS data; molecular ion and retention time): m/z 466.7 (M+H); 3.91 min] as an oil.

Step 8: In a 10 mL glass microwave reaction vessel under nitrogen, 17 mg (0.425 mmol) sodium hydride (obtained as a 60% dispersion in mineral oil) was slurried with a solution of 0.133 g (0.28 mmol) N-Boc-N'-{2-[2-phenyl-5-(4-propyl-cyclohexyl)-pyrrol-1-yl]-acetyl}-guanidine from Step 8 in 4 ml anhydrous DMF, and 41 mg (0.28 mmol) 3-bromopropionitrile. The reaction vessel was capped and microwave at 150° C. for 460 sec in a microwave reactor. (Emrys™ Microwave Synthesizer, Personal Chemistry Inc., Foxboro, Mass.) The reaction was concentrated and redissolved in 2 mL $CH_2Cl_2$. 0.66 mL trifluoroacetic acid was added and the reactions were shaken for 1 hr. The reactions were then concentrated, redissolved in DMSO:MeCN (4:1) and purified by Gilson preparative [4]HPLC to afford 34.5 mg of the title compound [[2]LC-MS data; molecular ion and retention time): m/z 434 (M+H); 2.77 min] as an oil.

EXAMPLE 474

Preparation of (N-(3-Cyano-propyl)-N'-[2-(2-cyclohexyl-5-phenyl-pyrrol-1-yl)-acetyl]-guanidine

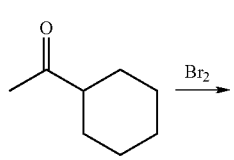

-continued

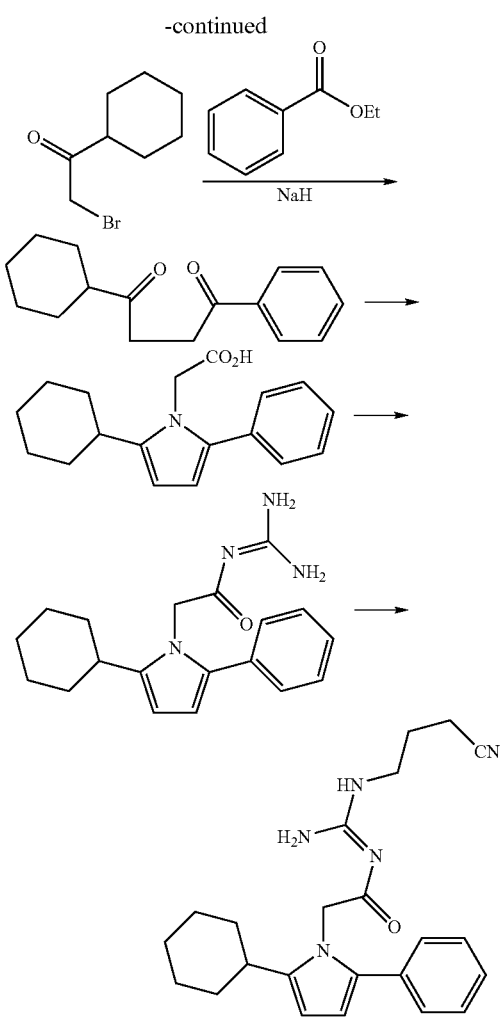

Step 1: A solution of 5.67 g (45 mmol) cyclohexyl methyl ketone in 27 mL anhydrous methanol was cooled to +10° C. in an ice bath and 9.58 g (60 mmol) bromine was added all at once. The reaction was stirred at +10° C. for 45 minutes, upon which time 7.5 mL of water was added. The reaction was stirred at room temperature for a further 2.5 hr and concentrated. The crude product was taken up in ether and washed with brine. The organic phase was dried over $MgSO_4$ and concentrated to afford crude 2-bromo-1-cyclohexyl-ethanone. The product was used immediately in the next step without further purification.

Step 2: To a stirred slurry of 1.44 g (36 mmol) sodium hydride, obtained as a 60% dispersion in mineral oil, in 45 mL anhydrous THF, at 0° C., was added dropwise 6.48 g (33.75 mmol) ethyl benzoyl acetate. The resulting slurry was stirred at 0° C. for 0.5 hr, upon which time was added dropwise the entire sample of 2-bromo-1-cyclohexyl-ethanone obtained in Step 1. The reaction was stirred at room temperature for 24 hr and poured into 0.4 L brine. The brine was shaken with ethyl acetate twice and the combined organic extracts were dried over $MgSO_4$ and concentrated to afford 14.37 g (45.4 mmol, >100% yield) of 2-benzoyl-4-cyclohexyl-4-oxo-butyric acid ethyl ester. The product was used in the next step without further purification.

Steps 3 and 4: 2-Benzoyl-4-cyclohexyl-4-oxo-butyric acid ethyl ester was converted to N''-[(2-cyclohexyl-5-phenyl-1H-pyrrol-1-yl)acetyl]guanidine following the procedure given in Example 473, Steps 5 and 6 [LC/MS data; molecular ion and retention time): m/z 325 (M+H); 2.43 min] as a white solid.

Step 5: N''-[(2-Cyclohexyl-5-phenyl-1H-pyrrol-1-yl) acetyl]guanidine was converted to N-(3-cyano-propyl)-N'-[2-(2-cyclohexyl-5-phenyl-pyrrol-1-yl)-acetyl]-guanidine following the procedure given in Example 473, Steps 7 and 8 [LC/MS data; molecular ion and retention time): m/z 392 (M+H); 2.47 min] as an oil.

EXAMPLE 475

Evaluation of BACE-1 Binding Affinity of Test Compounds

1. Fluorescent Kinetic Assays

Final Assay Conditions: 10 nM human BACE1 (or 10 nM Murine BACE1, 1.5 nM human BACE2), 25 µM substrate (WABC-6, MW 1549.6, from AnaSpec), Buffer: 50 mM Na-Acetate, pH 4.5, 0.05% CHAPS, 25% PBS, room temperature. Na-Acetate was from Aldrich, Cat.# 24, 124-5, CHAPS was from Research Organics, Cat. # 1304C 1×, PBS was from Mediatech (Cellgro), Cat# 21-031-CV, peptide substrate AbzSEVNLDAEFRDpa was from AnaSpec, Peptide Name: WABC-6

Determination of stock substrate (AbzSEVNLDAE-FRDpa) concentration: ~25 mM stock solution is made in DMSO using the peptide weight and MW, and diluted to ~25 µM (1:1000) in 1×PBS. Concentration is determined by absorbance at 354 nm using an extinction coefficient $\epsilon$ of 18172 $M^{-1}cm^{-1}$, the concentration of stock substrate is corrected, and the substrate stock stored in small aliquots in −80° C.

$$[\text{Substrate Stock}] = ABS^{354\,nm} * 10^6 / 18172 \text{ (in mM)}$$

The extinction coefficient $\epsilon^{354\,nm}$ was adapted from TACE peptide substrate, which had the same quencher-fluorophore pair.

Determination of Stock Enzyme Concentration: the stock concentration of each enzyme is determined by absorbance at 280 nm using $\epsilon$ of 64150 $M^{-1}cm^{-1}$ for hBACE1 and MuBACE1, 62870 $M^{-1}cm^{-1}$ for hBACE2 in 6 M Guanidinium Hydrochloride (from Research Organics, Cat. # 5134G-2), pH ~6. The extinction coefficient $\epsilon^{280\,nm}$ for each enzyme was calculated based on known amino acid composition and published extinction coefficients for Trp (5.69 $M^{-1}$ $cm^{-1}$) and Tyr (1.28 $M^{-1}$ $cm^{-1}$) residues (Anal. Biochem. 182, 319-326).

Dilution and mixing steps: total reaction volume: 100 µL
2× inhibitor dilutions in buffer A(66.7 mM Na-Acetate, pH 4.5, 0.0667% CHAPS) were prepared,
4× enzyme dilution in buffer A(66.7 mM Na-Acetate, pH 4.5, 0.0667% CHAPS) were prepared,
100 µM substrate dilution in 1×PBS was prepared, and
50 µL 2× Inhibitor, 25 µL 100 µM substrate are added to each well of 96-well plate (from DYNEX Technologies, VWR #: 11311-046), immediately followed by 25 µL 4× enzyme (added to the inhibitor and substrate mix), and the fluorescence readings are initiated.

Fluorescence Readings: Readings at $\lambda_{ex}$ 320 nm and $\lambda_{em}$ 420 nm are taken every 40 sec for 30 min at room temperature and the linear slope for substrate cleavage rate ($v_i$) determined.

Calculation of % Inhibition:

$$\% \text{ Inhibition} = 100 * (1 - v_i/v_0)$$

$v_i$: substrate cleavage rate in the presence of inhibitor
$v_0$: substrate cleavage rate in the absence of inhibitor $IC_{50}$ Determination:

$$\% \text{ Inhibition} = ((B * IC_{50}^n) + (100 * I_0^n))/(IC_{50}^n + I_0^n)$$

(Model # 39 from LSW Tool Bar in Excel where B is the % inhibition from the enzyme control, which should be close to 0.) % Inhibition is plotted vs. Inhibitor Concentration ($I_0$) and the data fit to the above equation to obtain $IC_{50}$ value and Hill number (n) for each compound. Testing at least 10 different inhibitor concentrations is preferred. The data obtained are shown below in Table XXV.

TABLE XXV

| Ex. No. | $IC_{50}$ (µM) BACE 1 |
|---|---|
| 1 | C |
| 11 | C |
| 15 | C |
| 16 | C |
| 19 | C |
| 21 | B |
| 30 | C |
| 32 | B |
| 35 | C |
| 36 | C |
| 44 | C |
| 46 | C |
| 56 | C |
| 57 | C |
| 68 | C |
| 70 | C |
| 87 | C |
| 91 | C |
| 94 | C |
| 96 | C |
| 110 | C |
| 133 | C |
| 135 | B |
| 147 | C |
| 162 | C |
| 169 | C |
| 170 | C |
| 185 | C |
| 231 | C |
| 233 | C |
| 235 | C |
| 236 | C |
| 242 | C |
| 244 | B |
| 258 | C |
| 267 | C |
| 271 | C |
| 273 | C |
| 274 | C |
| 277 | C |
| 280 | C |
| 282 | B |
| 283 | C |
| 309 | B |
| 310 | B |
| 311 | C |
| 312 | B |
| 313 | B |
| 314 | A |
| 315 | B |
| 316 | B |
| 317 | B |
| 318 | C |
| 319 | B |
| 320 | B |
| 321 | B |
| 322 | B |
| 323 | B |
| 324 | B |
| 325 | B |
| 326 | B |
| 327 | B |
| 328 | B |
| 329 | B |
| 330 | C |
| 331 | C |
| 332 | B |
| 333 | B |
| 334 | B |
| 335 | C |
| 336 | B |
| 337 | B |
| 338 | C |
| 389 | B |
| 390 | B |
| 391 | B |
| 392 | C |
| 393 | B |
| 394 | B |
| 395 | B |
| 396 | B |
| 397 | B |
| 398 | B |
| 400 | B |
| 401 | C |
| 402 | B |
| 404 | B |
| 405 | B |
| 406 | B |
| 407 | C |
| 408 | B |
| 409 | C |
| 410 | B |
| 411 | B |
| 412 | B |
| 413 | C |
| 414 | B |
| 415 | B |
| 416 | B |
| 417 | B |
| 418 | B |
| 419 | B |
| 420 | B |
| 421 | B |
| 422 | B |
| 423 | B |
| 424 | B |
| 425 | B |
| 426 | B |
| 431 | B |
| 447 | C |
| 449 | B |
| 450 | B |
| 451 | C |
| 452 | C |
| 453 | C |
| 454 | C |
| 461 | B |
| 462 | B |
| 463 | B |
| 464 | B |
| 465 | B |
| 467 | B |
| 468 | B |
| 469 | B |
| 470 | B |
| 472 | C |
| 473 | C |
| 474 | C |

For Table XXV
A = 0.01 µM–0.10 µM
B = 0.11 µM–1.00 µM
C = 1.10 µM–5.0 µM
D = >5.0 µM

What is claimed is:

1. A compound having the structure

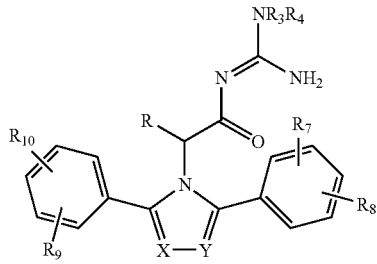

wherein
X is CH;
Y is CH;
R is H or alkyl;
$R_3$ and $R_4$ are each independently H, alkyl, alkoxy, alkanoyl, alkenyl, cycloalkyl, or aryl;
$R_7$, $R_8$, $R_9$ and $R_{10}$ are each independently H, halogen, alkyl, haloalkyl, cycloalkyl, aryl, $OR_{11}$, $COR_{11}$, $CONR_{12}R_{13}$, $NR_{12}R_{13}$, $NR_{14}COR_{15}$, $NR_{14}SO_2R_{15}$ or $NR_{14}CONR_{16}R_{17}$;
$R_{11}$ is H, alkyl, haloalkyl, alkenyl, alkynyl, cycloalkyl, or aryl;
$R_{12}$, $R_{13}$, $R_{16}$ and $R_{17}$ are each independently H, alkyl, alkoxy, alkenyl, cycloalkyl, or aryl;
$R_{14}$ is H, alkyl or cycloalkyl; and
$R_{15}$ is alkyl, haloalkyl, alkenyl, alkynyl, cycloalkyl, or, aryl; or a tautomer thereof, a stereoisomer thereof or a pharmaceutically acceptable salt thereof.

2. The compound according to claim 1 wherein R is H.

3. The compound according to claim 1 $R_7$ and $R_9$ are H.

4. The compound according to claim 3 wherein $R_8$ and $R_{10}$ are each independently H, halogen or $OR_{11}$.

5. The compound according to claim 1 selected from the group consisting of:

N-[amino(imino)methyl]-2-[2-(4-phenoxyphenyl)-5-phenyl-1H-pyrrol-1-yl]acetamide;
2-{2-[4-(4-acetylphenoxy)phenyl]-5-phenyl-1H-pyrrol-1-yl}-N-[amino(imino)methyl]acetamide;
N-[amino(imino)methyl]-2-[2-(2-chlorophenyl)-5-(4-phenoxyphenyl)-1H-pyrrol-1-yl]acetamide;
2-[2-[4-(4-acetylphenoxy)phenyl]-5-(2-chlorophenyl)-1H-pyrrol-1-yl]-N-[amino(imino)methyl]acetamide;
N-[amino(imino)methyl]-2-[2-(3-chlorophenyl)-5-(4-phenoxyphenyl)-1H-pyrrol-1-yl]acetamide;
N-[amino(imino)methyl]-2-[2-(3-fluorophenyl)-5-(4-phenoxyphenyl)-1H-pyrrol-1-yl]acetamide;
2-[2-[4-(4-acetylphenoxy)phenyl]-5-(3-fluorophenyl)-1H-pyrrol-1-yl]-N-[amino(imino)methyl]acetamide;
N-[amino(imino)methyl]-2-[2-(2-methoxyphenyl)-5-(4-phenoxyphenyl)-1H-pyrrol-1-yl]acetamide;
2-[2-[4-(4-acetylphenoxy)phenyl]-5-(2-methoxyphenyl)-1H-pyrrol-1-yl]-N-[amino(imino)methyl]acetamide;
N-[amino(imino)methyl]-2-[2-(3-methoxyphenyl)-5-(4-phenoxyphenyl)-1H-pyrrol-1-yl]acetamide;
2-[2-[4-(4-acetylphenoxy)phenyl]-5-(3-methoxyphenyl)-1H-pyrrol-1-yl]-N-[amino(imino)methyl]acetamide;
N-[amino(imino)methyl]-2-[2-(4-fluorophenyl)-5-(4-phenoxyphenyl)-1H-pyrrol-1-yl]acetamide;
2-[2-[4-(4-acetylphenoxy)phenyl]-5-(4-fluorophenyl)-1H-pyrrol-1-yl]-N-[amino(imino)methyl]acetamide;
N-[amino(imino)methyl]-2-[2-(2,5-dimethoxyphenyl)-5-(4-phenoxyphenyl)-1H-pyrrol-1-yl]acetamide;
2-[2-[4-(4-acetylphenoxy)phenyl]-5-(2,5-dimethoxyphenyl)-1H-pyrrol-1-yl]-N-[amino(imino)methyl]acetamide;
N-{4-[1-(2-{[amino(imino)methyl]amino}-2-oxoethyl)-5-phenyl-1H-pyrrol-2-yl]phenyl}-2,4-dichlorobenzamide;
N-{4-[1-(2-{[amino(imino)methyl]amino}-2-oxoethyl)-5-phenyl-1H-pyrrol-2-yl]phenyl}-4-bromobenzamide;
N-{4-[1-(2-{[amino(imino)methyl]amino}-2-oxoethyl)-5-phenyl-1H-pyrrol-2-yl]phenyl}-3-methoxybenzamide;
N-{4-[1-(2-{[amino(imino)methyl]amino}-2-oxoethyl)-5-phenyl-1H-pyrrol-2-yl]phenyl}-3-methylbenzamide;
N-{4-[1-(2-{[amino(imino)methyl]amino}-2-oxoethyl)-5-phenyl-1H-pyrrol-2-yl]phenyl}-2-phenoxyacetamide;
N-{4-[1-(2-{[amino(imino)methyl]amino}-2-oxoethyl)-5-phenyl-1H-pyrrol-2-yl]phenyl}-3-bromobenzamide;
2-{2-[4-(allyloxy)phenyl]-5-phenyl-1H-pyrrol-1-yl}-N-[amino(imino)methyl]acetamide;
N-[amino(imino)methyl]-2-(2-{4-[(2-methylprop-2-enyl)oxy]phenyl}-5-phenyl-1H-pyrrol-1-yl)acetamide;
N-[amino(imino)methyl]-2-{2-[4-(but-3-enyloxy)phenyl]-5-phenyl-1H-pyrrol-1-yl}acetamide;
N-[amino(imino)methyl]-2-(2-{4-[(4-cyanobenzyl)oxy]phenyl}-5-phenyl-1H-pyrrol-1-yl)acetamide;
N-[amino(imino)methyl]-2-[2-(4-ethoxyphenyl)-5-phenyl-1H-pyrrol-1-yl]acetamide;
N-[amino(imino)methyl]-2-[2-(4-butoxyphenyl)-5-phenyl-1H-pyrrol-1-yl]acetamide;
N-[amino(imino)methyl]-2-{2-[4-(3-cyanopropoxy)phenyl]-5-phenyl-1H-pyrrol-1-yl}acetamide;
N-[amino(imino)methyl]-2-[2-(4-{[(2S)-2-methylbutyl]oxy}phenyl)-5-phenyl-1H-pyrrol-1-yl]acetamide;
N-{(1E)-amino[(3-cyanopropyl)amino]methylene}-2-[2-(2-chlorophenyl)-5-(4-phenoxyphenyl)-1H-pyrrol-1-yl]acetamide;
N-{(1E)-amino[(3-hydroxypropyl)amino]methylene}-2-[2-(2-chlorophenyl)-5-(4-phenoxyphenyl)-1H-pyrrol-1-yl]acetamide;
methyl (2R)-3-{[(Z)-amino({[2-(2-chlorophenyl)-5-(4-phenoxyphenyl)-1H-pyrrol-1-yl]acetyl}imino)methyl]amino}-2-methylpropanoate;
2-{[(Z)-amino({[2-(2-chlorophenyl)-5-(4-phenoxyphenyl)-1H-pyrrol-1-yl]acetyl}imino)methyl]amino}ethyl acetate;
2-{2-(2-chlorophenyl)-5-[4-(pent-4-enyloxy)phenyl]-1H-pyrrol-1-yl}-N-[[(3-hydroxypropyl)amino](imino)methyl]acetamide;
2-{2-(2-chlorophenyl)-5-[4-(4-cyanobutoxy)phenyl]-1H-pyrrol-1-yl}-N-[[(3-hydroxypropyl)amino](imino)methyl]acetamide;
2-{2-(2-chlorophenyl)-5-[4-(hex-5-enyloxy)phenyl]-1H-pyrrol-1-yl}-N-[[(3-hydroxypropyl)amino](imino)methyl]acetamide;
2-{2-(2-chlorophenyl)-5-[4-(pentyloxy)phenyl]-1H-pyrrol-1-yl}-N-[[(3-hydroxypropyl)amino](imino)methyl]acetamide;
2-[2-(4-cyanophenyl)-5-phenyl-1H-pyrrol-1-yl]-N-[[(3-hydroxypropyl)amino](imino)methyl]acetamide;
N-[[(3-hydroxypropyl)amino](imino)methyl]-2-[2-(4-isopropylphenyl)-5-phenyl-1H-pyrrol-1-yl]acetamide;
N-[[(3-hydroxypropyl)amino](imino)methyl]-2-[2-phenyl-5-(4-propylphenyl)-1H-pyrrol-1-yl]acetamide;

2-[2-(4-butylphenyl)-5-phenyl-1H-pyrrol-1-yl]-N-[[(3-hydroxypropyl)amino](imino)methyl]acetamide;
N-[[(3-hydroxypropyl)amino](imino)methyl]-2-[2-(4-isobutylphenyl)-5-phenyl-1H-pyrrol-1-yl]acetamide;
N-[[(3-hydroxypropyl)amino](imino)methyl]-2-[2-(4-pentylphenyl)-5-phenyl-1H-pyrrol-1-yl]acetamide;
2-[2-(4-butoxyphenyl)-5-phenyl-1H-pyrrol-1-yl]-N-[[(3-hydroxypropyl)amino](imino)methyl]acetamide;
2-[2-(1,1'-biphenyl-4-yl)-5-phenyl-1H-pyrrol-1-yl]-N-[[(3-hydroxypropyl)amino](imino)methyl]acetamide;
2-[2-(4-bromophenyl)-5-phenyl-1H-pyrrol-1-yl]-N-[[(3-hydroxypropyl)amino](imino)methyl]acetamide;
2-[2-(4-cyclohexylphenyl)-5-phenyl-1H-pyrrol-1-yl]-N-[[(3-hydroxypropyl)amino](imino)methyl]acetamide;
N-[[(3-hydroxypropyl)amino](imino)methyl]-2-[2-(4-phenoxyphenyl)-5-phenyl-1H-pyrrol-1-yl]acetamide;
2-{2-[4-(4-acetylphenoxy)phenyl]-5-phenyl-1H-pyrrol-1-yl}-N-[[(3-hydroxypropyl)amino](imino)methyl]acetamide;
2-[2-(4-cyanophenyl)-5-phenyl-1H-pyrrol-1-yl]-N-{imino[(2,3,4-trifluorobenzyl)amino]methyl}acetamide;
N-{imino[(2,3,4-trifluorobenzyl)amino]methyl}-2-[2-phenyl-5-(4-propylphenyl)-1H-pyrrol-1-yl]acetamide;
2-[2-(4-butylphenyl)-5-phenyl-1H-pyrrol-1-yl]-N-{imino[(2,3,4-trifluorobenzyl)amino]methyl}acetamide;
2-[2-(4-butoxyphenyl)-5-phenyl-1H-pyrrol-1-yl]-N-{imino[(2,3,4-trifluorobenzyl)amino]methyl}acetamide;
2-[2-(4-cyclohexylphenyl)-5-phenyl-1H-pyrrol-1-yl]-N-{imino[(2,3,4-trifluorobenzyl)amino]Methyl}acetamide;
N-{imino[(2,3,4-trifluorobenzyl)amino]methyl}-2-[2-(4-phenoxyphenyl)-5-phenyl-1H-pyrrol-1-yl]acetamide;
2-{2-[4-(4-acetylphenoxy)phenyl]-5-phenyl-1H-pyrrol-1-yl}-N-{imino[(2,3,4-trifluorobenzyl)amino]methyl}acetamide;
N-allyl-4-{1-[2-({(1E)-amino[(3-aminobenzyl)amino]methylene}amino)-2-oxoethyl]-5-phenyl-1H-pyrrol-2-yl}benzamide;
N"-{[2-(4-butylphenyl)-5-phenyl-1H-pyrrol-1-yl]acetyl}guanidine;
N"-{[2-(2,5-dimethylphenyl)-5-phenyl-1H-pyrrol-1-yl]acetyl}guanidine;
N"-({2-[3-(cyanomethyl)phenyl]-5-phenyl-1H-pyrrol-1-yl}acetyl)guanidine;
N"-({2-[4-(2-cyanoethyl)phenyl]-5-phenyl-1H-pyrrol-1-yl}acetyl)guanidine;
4-{1-[2-({(1E)-amino[(3-hydroxypropyl)amino]methylene}amino)-2-oxoethyl]-5-phenyl-1H-pyrrol-2-yl}-N-ethylbenzamide;
4-{1-[2-({(1E)-amino[(3-hydroxypropyl)amino]methylene}amino)-2-oxoethyl]-5-phenyl-1H-pyrrol-2-yl}-N-cyclopropylbenzamide;
N-allyl-4-{1-[2-({(1E)-amino[(3-hydroxypropyl)amino]methylene}amino)-2-oxoethyl]-5-phenyl-1H-pyrrol-2-yl}benzamide;
4-{1-[2-({(1E)-amino[(3-hydroxypropyl)amino]methylene}amino)-2-oxoethyl]-5-phenyl-1H-pyrrol-2-yl}-N-(2-hydroxyethyl)benzamide;
4-{1-[2-({(1E)-amino[(3-hydroxypropyl)amino]methylene}amino)-2-oxoethyl]-5-phenyl-1H-pyrrol-2-yl}-N-(2-cyanoethyl)benzamide;
4-{1-[2-({(1E)-amino[(3-hydroxypropyl)amino]methylene}amino)-2-oxoethyl]-5-phenyl-1H-pyrrol-2-yl}-N-propylbenzamide;
4-{1-[2-({(1E)-amino[(3-hydroxypropyl)amino]methylene)amino)-2-oxoethyl]-5-phenyl-1H-pyrrol-2-yl}-N-(2-methoxyethyl)benzamide;
4-{1-[2-({(1E)-amino[(3-hydroxypropyl)amino]methylene}amino)-2-oxoethyl]-5-phenyl-1H-pyrrol-2-yl}-N-(sec-butyl)benzamide;
N-allyl-4-{1-[2-({(1E)-amino[(3-hydroxypropyl)amino]methylene}amino)-2-oxoethyl]-5-phenyl-1H-pyrrol-2-yl}-N-methylbenzamide;
4-{1-[2-({(1E)-amino[(3-hydroxypropyl)amino]methylene}amino)-2-oxoethyl]-5-phenyl-1H-pyrrol-2-yl]-N-(2,2,3,3,3-pentafluoropropyl)benzamide;
a tautomer thereof;
a stereoisomer thereof; and
a pharmaceutically acceptable salt thereof.

6. A method for inhibiting the activity of BACE in vitro comprising contacting a receptor thereof with an effective amount of a compound of claim 1.

7. A pharmaceutical composition which comprises a pharmaceutically acceptable carrier and an effective amount of a compound of claim 1.

8. The composition according to claim 7 having a formula I compound selected from the group consisting of:
N-[amino(imino)methyl]-2-[2-(4-phenoxyphenyl)-5-phenyl-1H-pyrrol-1-yl]acetamide;
2-{2-[4-(4-acetylphenoxy)phenyl]-5-phenyl-1H-pyrrol-1-yl}-N-[amino(imino)methyl]acetamide;
N-[amino(imino)methyl]-2-[2-(2-chlorophenyl)-5-(4-phenoxyphenyl)-1H-pyrrol-1-yl]acetamide;
2-[2-[4-(4-acetylphenoxy)phenyl]-5-(2-chlorophenyl)-1H-pyrrol-1-yl]-N-[amino(imino)methyl]acetamide;
N-[amino(imino)methyl]-2-[2-(3-chlorophenyl)-5-(4-phenoxyphenyl)-1H-pyrrol-1-yl]acetamide;
N-[amino(imino)methyl]-2-[2-(3-fluorophenyl)-5-(4-phenoxyphenyl)-1H-pyrrol-1-yl]acetamide;
2-[2-[4-(4-acetylphenoxy)phenyl]-5-(3-fluorophenyl)-1H-pyrrol-1-yl]-N-[amino(imino)methyl]acetamide;
N-[amino(imino)methyl]-2-[2-(2-methoxyphenyl)-5-(4-phenoxyphenyl)-1H-pyrrol-1-yl]acetamide;
2-[2-[4-(4-acetylphenoxy)phenyl]-5-(2-methoxyphenyl)-1H-pyrrol-1-yl]-N-[amino(imino)methyl]acetamide;
N-[amino(imino)methyl]-2-[2-(3-methoxyphenyl)-5-(4-phenoxyphenyl)-1H-pyrrol-1-yl]acetamide;
2-[2-[4-(4-acetylphenoxy)phenyl]-5-(3-methoxyphenyl)-1H-pyrrol-1-yl]-N-[amino(imino)methyl]acetamide;
N-[amino(imino)methyl]-2-[2-(4-fluorophenyl)-5-(4-phenoxyphenyl)-1H-pyrrol-1-yl]acetamide;
2-[2-[4-(4-acetylphenoxy)phenyl]-5-(4-fluorophenyl)-1H-pyrrol-1-yl]-N-[amino(imino)methyl]acetamide;
N-[amino(imino)methyl]-2-[2-(2,5-dimethoxyphenyl)-5-(4-phenoxyphenyl)-1H-pyrrol-1-yl]acetamide;
2-[2-[4-(4-acetylphenoxy)phenyl]-5-(2,5-dimethoxyphenyl)-1H-pyrrol-1-yl]-N-[amino(imino)methyl]acetamide;
N-{4-[1-(2-{[amino(imino)methyl]amino}-2-oxoethyl)-5-phenyl-1H-pyrrol-2-yl]phenyl}-2,4-dichlorobenzamide;
N-{4-[1-(2-{[amino(imino)methyl]amino}-2-oxoethyl)-5-phenyl-1H-pyrrol-2-yl]phenyl}-4-bromobenzamide;
N-{4-[1-(2-{[amino(imino)methyl]amino}-2-oxoethyl)-5-phenyl-1H-pyrrol-2-yl]phenyl}-3-methoxybenzamide;
N-{4-[1-(2-{[amino(imino)methyl]amino}-2-oxoethyl)-5-phenyl-1H-pyrrol-2-yl]phenyl}-3-methylbenzamide;
N-{4-[1-(2-{[amino(imino)methyl]amino}-2-oxoethyl)-5-phenyl-1H-pyrrol-2-yl]phenyl}-2-phenoxyacetamide;

N-{4-[1-(2-{[amino(imino)methyl]amino}-2-oxoethyl)-5-phenyl-1H-pyrrol-2-yl]phenyl}-3-bromobenzamide;
2-{2-[4-(allyloxy)phenyl]-5-phenyl-1H-pyrrol-1-yl}-N-[amino(imino)methyl]acetamide;
N-[amino(imino)methyl]-2-(2-{4-[(2-methylprop-2-enyl)oxy]phenyl}-5-phenyl-1H-pyrrol-1-yl)acetamide;
N-[amino(imino)methyl]-2-{2-[4-(but-3-enyloxy)phenyl]-5-phenyl-1H-pyrrol-1-yl}acetamide;
N-[amino(imino)methyl]-2-(2-{4-[(4-cyanobenzyl)oxy]phenyl}-5-phenyl-1H-pyrrol-1-yl)acetamide;
N-[amino(imino)methyl]-2-[2-(4-ethoxyphenyl)-5-phenyl-1H-pyrrol-1-yl]acetamide;
N-[amino(imino)methyl]-2-[2-(4-butoxyphenyl)-5-phenyl-1H-pyrrol-1-yl]acetamide;
N-[amino(imino)methyl]-2-{2-[4-(3-cyanopropoxy)phenyl]-5-phenyl-1H-pyrrol-1-yl}acetamide;
N-[amino(imino)methyl]-2-[2-(4-{[(2S)-2-methylbutyl]oxy}phenyl)-5-phenyl-1H-pyrrol-1-yl]acetamide;
N-{(1E)-amino[(3-cyanopropyl)amino]methylene}-2-[2-(2-chlorophenyl)-5-(4-phenoxyphenyl)-1H-pyrrol-1-yl]acetamide;
N-{(1E)-amino[(3-hydroxypropyl)amino]methylene}-2-[2-(2-chlorophenyl)-5-(4-phenoxyphenyl)-1H-pyrrol-1-yl]acetamide;
methyl (2R)-3-{[(Z)-amino({[2-(2-chlorophenyl)-5-(4-phenoxyphenyl)-1H-pyrrol-1-yl]acetyl}imino)methyl]amino}-2-methylpropanoate;
2-{[(Z)-amino({[2-(2-chlorophenyl)-5-(4-phenoxyphenyl)-1H-pyrrol-1-yl]acetyl}imino)methyl]amino}ethyl acetate;
2-{2-(2-chlorophenyl)-5-[4-(pent-4-enyloxy)phenyl]-1H-pyrrol-1-yl}-N-[[(3-hydroxypropyl)amino](imino)methyl]acetamide;
2-{2-(2-chlorophenyl)-5-[4-(4-cyanobutoxy)phenyl]-1H-pyrrol-1-yl}-N-[[(3-hydroxypropyl)amino](imino)methyl]acetamide;
2-{2-(2-chlorophenyl)-5-[4-(hex-5-enyloxy)phenyl]-1H-pyrrol-1-yl}-N-[[(3-hydroxypropyl)amino](imino)methyl]acetamide;
2-{2-(2-chlorophenyl)-5-[4-(pentyloxy)phenyl]-1H-pyrrol-1-yl}-N-[[(3-hydroxypropyl)amino](imino)methyl]acetamide;
2-[2-(4-cyanophenyl)-5-phenyl-1H-pyrrol-1-yl]-N-[[(3-hydroxypropyl)amino](imino)methyl]acetamide;
N-[[(3-hydroxypropyl)amino](imino)methyl]-2-[2-(4-isopropylphenyl)-5-phenyl-1H-pyrrol-1-yl]acetamide;
N-[[(3-hydroxypropyl)amino](imino)methyl]-2-[2-phenyl-5-(4-propylphenyl)-1H-pyrrol-1-yl]acetamide;
2-[2-(4-butylphenyl)-5-phenyl-1H-pyrrol-1-yl]-N-[[(3-hydroxypropyl)amino](imino)methyl]acetamide;
N-[[(3-hydroxypropyl)amino](imino)methyl]-2-[2-(4-isobutylphenyl)-5-phenyl-1H-pyrrol-1-yl]acetamide;
N-[[(3-hydroxypropyl)amino](imino)methyl]-2-[2-(4-pentylphenyl)-5-phenyl-1H-pyrrol-1-yl]acetamide;
2-[2-(4-butoxyphenyl)-5-phenyl-1H-pyrrol-1-yl]-N-[[(3-hydroxypropyl)amino](imino)methyl]acetamide;
2-[2-(1,1'-biphenyl-4-yl)-5-phenyl-1H-pyrrol-1-yl]-N-[[(3-hydroxypropyl)amino](imino)methyl]acetamide;
2-[2-(4-bromophenyl)-5-phenyl-1H-pyrrol-1-yl]-N-[[(3-hydroxypropyl)amino](imino)methyl]acetamide;
2-[2-(4-cyclohexylphenyl)-5-phenyl-1H-pyrrol-1-yl]-N-[[(3-hydroxypropyl)amino](imino)methyl]acetamide;
N-[[(3-hydroxypropyl)amino](imino)methyl]-2-[2-(4-phenoxyphenyl)-5-phenyl-1H-pyrrol-1-yl]acetamide;
2-{2-[4-(4-acetylphenoxy)phenyl]-5-phenyl-1H-pyrrol-1-yl}-N-[[(3-hydroxypropyl)amino](imino)methyl]acetamide;
2-[2-(4-cyanophenyl)-5-phenyl-1H-pyrrol-1-yl]-N-{imino[(2,3,4-trifluorobenzyl)amino]methyl}acetamide;
N-{imino[(2,3,4-trifluorobenzyl)amino]methyl}-2-[2-phenyl-5-(4-propylphenyl)-1H-pyrrol-1-yl]acetamide;
2-[2-(4-butylphenyl)-5-phenyl-1H-pyrrol-1-yl]-N-{imino[(2,3,4-trifluorobenzyl)amino]methyl}acetamide;
2-[2-(4-butoxyphenyl)-5-phenyl-1H-pyrrol-1-yl]-N-{imino[(2,3,4-trifluorobenzyl)amino]methyl}acetamide;
2-[2-(4-cyclohexylphenyl)-5-phenyl-1H-pyrrol-1-yl]-N-{imino[(2,3,4-trifluorobenzyl)amino]Methyl}acetamide;
N-{imino[(2,3,4-trifluorobenzyl)amino]methyl}-2-[2-(4-phenoxyphenyl)-5-phenyl-1H-pyrrol-1-yl]acetamide;
2-{2-[4-(4-acetylphenoxy)phenyl]-5-phenyl-1H-pyrrol-1-yl}-N-{imino[(2,3,4-trifluorobenzyl)amino]methyl}acetamide;
N''-{[2-(4-butylphenyl)-5-phenyl-1H-pyrrol-1-yl]acetyl}guanidine;
N''-{[2-(2,5-dimethylphenyl)-5-phenyl-1H-pyrrol-1-yl]acetyl}guanidine;
N''-({2-[3-(cyanomethyl)phenyl]-5-phenyl-1H-pyrrol-1-yl}acetyl)guanidine;
N''-({2-[4-(2-cyanoethyl)phenyl]-5-phenyl-1H-pyrrol-1-yl}acetyl)guanidine;
4-{1-[2-({(1E)-amino[(3-hydroxypropyl)amino]methylene}amino)-2-oxoethyl]-5-phenyl-1H-pyrrol-2-yl}-N-ethylbenzamide;
4-{1-[2-({(1E)-amino[(3-hydroxypropyl)amino]methylene}amino)-2-oxoethyl]-5-phenyl-1H-pyrrol-2-yl}-N-cyclopropylbenzamide;
N-allyl-4-{1-[2-({(1E)-amino[(3-hydroxypropyl)amino]methylene}amino)-2-oxoethyl]-5-phenyl-1H-pyrrol-2-yl}benzamide;
4-{1-[2-({(1E)-amino[(3-hydroxypropyl)amino]methylene}amino)-2-oxoethyl]-5-phenyl-1H-pyrrol-2-yl}-N-(2-hydroxyethyl)benzamide;
4-{1-[2-({(1E)-amino[(3-hydroxypropyl)amino]methylene}amino)-2-oxoethyl]-5-phenyl-1H-pyrrol-2-yl}-N-(2-cyanoethyl)benzamide;
4-{1-[2-({(1E)-amino[(3-hydroxypropyl)amino]methylene}amino)-2-oxoethyl]-5-phenyl-1H-pyrrol-2-yl}-N-propylbenzamide;
4-{1-[2-({(1E)-amino[(3-hydroxypropyl)amino]methylene}amino)-2-oxoethyl]-5-phenyl-1H-pyrrol-2-yl}-N-(2-methoxyethyl)benzamide;
4-{1-[2-({(1E)-amino[(3-hydroxypropyl)amino]methylene}amino)-2-oxoethyl]-5-phenyl-1H-pyrrol-2-yl}-N-(sec-butyl)benzamide;
N-allyl-4-{1-[2-({(1E)-amino[(3-hydroxypropyl)amino]methylene}amino)-2-oxoethyl]-5-phenyl-1H-pyrrol-2-yl}-N-methylbenzamide;
4-{1-[2-({(1E)-amino[(3-hydroxypropyl)amino]methylene}amino)-2-oxoethyl]-5-phenyl-1H-pyrrol-2-yl}-N-(2,2,3,3,3-pentafluoropropyl)benzamide;
a tautomer thereof;
a stereoisomer thereof; and
a pharmaceutically acceptable salt thereof.

* * * * *